United States Patent
Langlade-Demoyen et al.

(10) Patent No.: US 9,624,479 B2
(45) Date of Patent: *Apr. 18, 2017

(54) POLYNUCLEOTIDES ENCODING MHC CLASS I-RESTRICTED HTERT EPITOPES, ANALOGUES THEREOF OR POLYEPITOPES

(71) Applicants: INSTITUT PASTEUR, Paris (FR); INSERM (INSTITUT NATIONAL DE LA SANTE ET DE LA RECHERCHE MEDICALE), Paris (FR)

(72) Inventors: Pierre Langlade-Demoyen, Paris (FR); Fransisco Garcia Pons, Maurepas (FR); Olivier Adotevi, Nogent sur Marne (FR); Sylvain Cardinaud, Carrleves sur Seine (FR); Christine Neuveut, Arcuell (FR)

(73) Assignees: INSTITUT PASTEUR, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 777 days.

This patent is subject to a terminal disclaimer.

(21) Appl. No.: 13/975,404

(22) Filed: Aug. 26, 2013

(65) Prior Publication Data
US 2014/0056932 A1    Feb. 27, 2014

Related U.S. Application Data

(63) Continuation of application No. 11/795,027, filed as application No. PCT/EP2006/007571 on Jul. 31, 2006, now Pat. No. 8,858,931.

(30) Foreign Application Priority Data

Jul. 29, 2005  (FR) .................................. 05 291627

(51) Int. Cl.
| | |
|---|---|
| *A01N 63/00* | (2006.01) |
| *C12N 15/00* | (2006.01) |
| *A61K 48/00* | (2006.01) |
| *C07H 21/00* | (2006.01) |
| *C12N 9/12* | (2006.01) |
| *C12N 5/00* | (2006.01) |

(52) U.S. Cl.
CPC ......... *C12N 9/1276* (2013.01); *C12N 9/1241* (2013.01)

(58) Field of Classification Search
None
See application file for complete search history.

(56) References Cited

U.S. PATENT DOCUMENTS 8,003,773 B2    8/2011  Langlade-Demoyen et al.
8,858,931 B2 *  10/2014 Langlade-Demoyen  C12N 9/1276
                                              424/93.7

FOREIGN PATENT DOCUMENTS

WO         0002581     1/2000
WO      2005051420 A1  6/2005

OTHER PUBLICATIONS

Jakob Dupont et al., Cancer Res 2005;65:5417-5427.
Maria Frolkis et al., Cancer Gene Therapy 2003;10:239-249.
Jun Lu et al., Cancer Res 2000;60:5223-5227.
Trends in Immunology 2001:vol. 22, 516-523.
Vanda Turcanova et al., Journal of Medical Virology 2004;72:635-645 (2004).
Robert H Vonderheide et al., Oncogene 2002;21:674-679.
Robert H. Vonderheide et al., Clin Cancer Res 2004;10:828-839.
Su Zhen et al., J Immunol 2005; 174:3798-3807.
Reply to Office Action filed Jul. 11, 2014, in U.S. Appl. No. 11/795,027.

\* cited by examiner

*Primary Examiner* — Michael Szperka
*Assistant Examiner* — Marianne DiBrino
(74) *Attorney, Agent, or Firm* — Arrigo, Lee & Guttman LLP

(57) ABSTRACT

This invention relates to the field of anticancer therapy, and to the identification of immunogenic peptides derived from the human telomerase reverse transcriptase (hTERT). The present invention relates to polynucleotides encoding hTERT epitopes restricted to MHC class I molecule, analogs thereof and polyepitopes containing such epitopes and/or analogs. Are also included in the present invention, vector and cell comprising such polynucleotides. The present invention also concerns composition comprising hTERT polypeptides, corresponding polynucleotides, vectors and cells, for use in the treatment and/or prevention of cancer.

20 Claims, 24 Drawing Sheets

Figure 2:
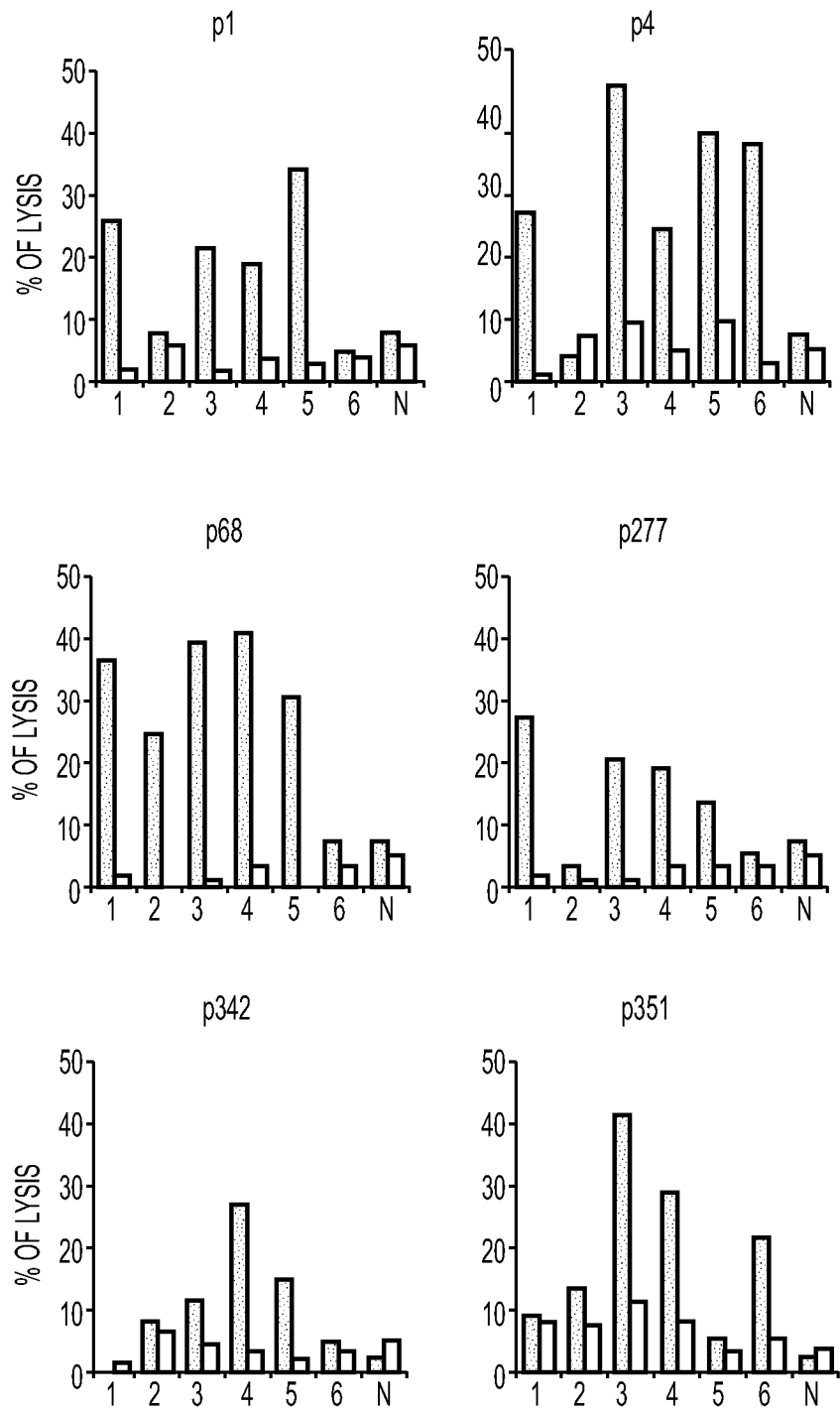

```
gcagcgctgc gtcctgctgc gcacgtggga agccctggcc ccggcacccc ccgcg atg    58
                                                              met ccg cgc gct ccc cgc tgc cga gcc gtg cgc tcc ctg ctg cgc agc cac    106
Pro Arg Ala Pro Arg Cys Arg Ala Val Arg Ser Leu Leu Arg Ser His
         5                   10                  15
tac cgc gag gtg ctg ccg ctg gcc acg ttc gtg cgg cgc ctg ggg ccc    154
Tyr Arg Glu Val Leu Pro Leu Ala Thr Phe Val Arg Arg Leu Gly Pro
             20                  25                  30
cag ggc tgg cgg ctg gtg cag cgc ggg gac ccg gcg gct ttc cgc gcg    202
Gln Gly Trp Arg Leu Val Gln Arg Gly Asp Pro Ala Ala Phe Arg Ala
         35                  40                  45
ctg gtg gcc cag tgc ctg gtg tgc gtg ccc tgg gac gca cgg ccg ccc    250
Leu Val Ala Gln Cys Leu Val Cys Val Pro Trp Asp Ala Arg Pro Pro
 50                  55                  60                  65
ccc gcc gcc ccc tcc ttc cgc cag gtg tcc tgc ctg aag gag ctg gtg    298
Pro Ala Ala Pro Ser Phe Arg Gln Val Ser Cys Leu Lys Glu Leu Val
                 70                  75                  80
gcc cga gtg ctg cag agg ctg tgc gag cgc ggc gcg aag aac gtg ctg    346
Ala Arg Val Leu Gln Arg Leu Cys Glu Arg Gly Ala Lys Asn Val Leu
             85                  90                  95
gcc ttc ggc ttc gcg ctg ctg gac ggg gcc cgc ggg ggc ccc ccc gag    394
Ala Phe Gly Phe Ala Leu Leu Asp Gly Ala Arg Gly Gly Pro Pro Glu
         100                 105                 110
gcc tcc acc acc agc gtg cgc agc tac ctg ccc aac acg gtg acc gac    442
Ala Phe Thr Thr Ser Val Arg Ser Tyr Leu Pro Asn Thr Val Thr Asp
 115                 120                 125
gca ctg cgg ggg agc ggg gcg tgg ggg ctg ctg ctg cgc cgc gtg ggc    490
Ala Leu Arg Gly Ser Gly Ala Trp Gly Leu Leu Leu Arg Arg Val Gly
130                 135                 140                 145
gac gac gtg ctg gtt cac ctg ctg gca cgc tgc gcg ctc ttt gtg ctg    538
Asp Asp Val Leu Val His Leu Leu Ala Arg Cys Ala Leu Phe Val Leu
                 150                 155                 160
gtg gct ccc agc tgc gcc tac cag gtg tgc ggg ccg ccg ctg tac cag    586
Val Ala Pro Ser Cys Ala Tyr Gln Val Cys Gly Pro Pro Leu Tyr Gln
             165                 170                 175
ctc ggc gct gcc act cag gcc cgg ccc ccg cca cac gct agt gga ccc    634
Leu Gly Ala Ala Thr Gln Ala Arg Pro Pro Pro His Ala Ser Gly Pro
         180                 185                 190
cga agg cgt ctg gga tgc gaa cgg gcc tgg aac cat agc gtc agg gag    682
Arg Arg Arg Leu Gly Cys Glu Arg Ala Trp Asn His Ser Val Arg Glu
 195                 200                 205
```

*FIG.1A*

```
gcc ggg gtc ccc ctg ggc ctg cca gcc ccg ggt gcg agg agg cgc ggg    730
Ala Gly Val Pro Leu Gly Leu Pro Ala Pro Gly Ala Arg Arg Arg Gly
210             215                 220                 225
ggc agt gcc agc cga agt ctg ccg ttg ccc aag agg ccc agg cgt ggc    778
Gly Ser Ala Ser Arg Ser Leu Pro Leu Pro Lys Arg Pro Arg Arg Gly
                230                 235                 240
gct gcc cct gag ccg gag cgg acg ccc gtt ggg cag ggg tcc tgg gcc    826
Ala Ala Pro Glu Pro Glu Arg Thr Pro Val Gly Gln Gly Ser Trp Ala
            245                 250                 255
cac ccg ggc agg acg cgt gga ccg agt gac cgt ggt ttc tgt gtg gtg    874
His Pro Gly Arg thr Arg Gly Pro Ser Asp Arg Gly Phe Cys Val Val
            260                 265                 270
tca cct gcc aga ccc gcc gaa gaa gcc acc tct ttg gag ggt gcg ctc    922
Ser Pro Ala Arg Pro Ala Glu Glu Ala Thr Ser Leu Glu Gly Ala Leu
        275                 280                 285
tct ggc acg cgc cac tcc cac cca tcc gtg ggc cgc cag cac cac gcg    970
Ser Gly Thr Arg His Ser His Pro Ser Val Gly Arg Gln His His Ala
290             295                 300                 305
ggc ccc cca tcc aca tcg cgg cca cca cgt ccc tgg gac acg cct tgt   1018
Gly Pro Pro Ser Thr Ser Arg Pro Pro Arg Pro Trp Asp Thr Pro Cys
                310                 315                 320
ccc ccg gtg tac gcc gag acc aag cac ttc ctc tac tcc tca ggc gac   1066
Pro Pro Val Tyr Ala Glu Thr Lys His Phe Leu Tyr Ser Ser Gly Asp
            325                 330                 335
aag gag cag ctg cgg ccc tcc ttc cta ctc agc tct ctg agg ccc agc   1114
Lys Glu Gln Leu Arg Pro Ser Phe Leu Leu Ser Ser Leu Arg Pro Ser
            340                 345                 350
ctg act ggc gct cgg agg ctc gtg gag acc atc ttt ctg ggt tcc agg   1162
Leu Thr Gly Ala Arg Arg Leu Val Glu Thr Ile Phe Leu Gly Ser Arg
        355                 360                 365
ccc tgg atg cca ggg act ccc cgc agg ttg ccc cgc ctg ccc cag cgc   1210
Pro Trp Met Pro Gly Thr Pro Arg Arg Leu Pro Arg Leu Pro Gln Arg
370             375                 380                 385
tac tgg caa atg cgg ccc ctg ttt ctg gag ctg ctt ggg aac cac gcg   1258
Tyr Trp Gln Met Arg Pro Leu Phe Leu Glu Leu Leu Gly Asn His Ala
                390                 395                 400
cag tgc ccc tac ggg gtg ctc ctc aag acg cac tgc ccg ctg cga gct   1306
Gln Cys Pro Tyr Gly Val Leu Leu Lys Thr His Cys Pro Leu Arg Ala
            405                 410                 415
gcg gtc acc cca gca gcc ggt gtc tgt gcc cgg gag aag ccc cag ggc   1354
Ala Val Thr Pro Ala Ala Gly Val Cys Ala Arg Glu Lys Pro Gln Gly
            420                 425                 430
```

*FIG. 1B*

```
tct gtg gcg gcc ccc gag gag gag gac aca gac ccc cgt cgc ctg gtg    1402
Ser Val Ala Ala Pro Glu Glu Glu Asp Thr Asp Pro Arg Arg Leu Val
        435                 440                 445
cag ctg ctc cgc cag cac agc agc ccc tgg cag gtg tac ggc ttc gtg    1450
Gln Leu Leu Arg Gln His Ser Ser Pro Trp Gln Val Tyr Gly Phe Val
450                 455                 460                 465
cgg gcc tgc ctg cgc cgg ctg gtg ccc cca ggc ctc tgg ggc tcc agg    1498
Arg Ala Cys Leu Arg Arg Leu Val Pro Pro Gly Leu Trp Gly Ser Arg
            470                 475                 480
cac aac gaa cgc cgc ttc ctc agg aac acc aag aag ttc atc tcc ctg    1546
His Asn Glu Arg Arg Phe Leu Arg Asn Thr Lys Lys Phe Ile Ser Leu
                485                 490                 495
ggg aag cat gcc aag ctc tcg ctg cag gag ctg acg tgg aag atg agc    1594
Gly Lys His Ala Lys Leu Ser Leu Gln Glu Leu Thr Trp Lys met Ser
            500                 505                 510
gtg cgg gac tgc gct tgg ctg cgc agg agc cca ggg gtt ggc tgt gtt    1642
Val Arg Asp Cys Ala Trp Leu Arg Arg ser Pro Gly Val Gly Cys Val
        515                 520                 525
ccg gcc gca gag cac cgt ctg cgt gag gag atc ctg gcc aag ttc ctg    1960
Pro Ala Ala Glu his Arg Leu Arg Glu Glu Ile Leu Ala Lys Phe Leu
530                 535                 540                 545
cac tgg ctg atg agt gtg tac gtc gtc gag ctg ctc agg tct ttc ttt    1738
His Trp Leu Met Ser Val Tyr Val Val Glu Leu Leu Arg Ser Phe Phe
                550                 555                 560
tat gtc acg gag acc acg ttt caa aag aac agg ctc ttt ttc tac cgg    1786
Tyr Val Thr Glu Thr Thr Phe Gln Lys Asn Arg Leu Phe Phe Tyr Arg
                565                 570                 575
aag agt gtc tgg agc aag ttg caa agc att gga atc aga cag cac ttg    1834
Lys Ser Val Trp Ser Lys Leu Gln Ser Ile Gly Ile Arg Gln His Leu
            580                 585                 590
aag agg gtg cag ctg cgg gag ctg tcg gaa gca gag gtc agg cag cat    1882
Lys Arg Val Gln Leu Arg Glu Leu Ser Glu Ala Glu Val Arg Gln His
        595                 600                 605
cgg gaa gcc agg ccc gcc ctg ctg acg tcc aga ctc cgc ttc atc ccc    1930
Arg Glu Ala Arg Pro Ala Leu Leu Thr Ser Arg Leu Arg Phe Ile Pro
610                 615                 620                 625
aag cct gac ggg ctg cgg ccg att gtg aac atg gac tac gtc gtg gga    1978
Lys Pro Asp Gly Leu Arg Pro Ile Val Asn Met Asp Tyr Val Val Gly
                630                 635                 640
gcc aga acg ttc cgc aga gaa aag agg gcc gag cgt ctc acc tcg agg    2026
Ala Arg Thr Phe Arg Arg Glu Lys Arg Ala Glu Arg Leu Thr Ser Arg
                645                 650                 655
```

FIG. 1C

```
gtg aag gca ctg ttc agc gtg ctc aac tac gag cgg gcg cgg cgc ccc    2074
Val Lys Ala Leu Phe Ser Val Leu Asn Tyr Glu Arg Ala Arg Arg Pro
        660                 665                 670
ggc ctc ctg ggc gcc tct gtg ctg ggc ctg gac gat atc cac agg gcc    2122
Gly Leu Leu Gly Ala Ser Val Leu Gly Leu Asp Asp Ile His Arg Ala
    675                 680                 685
tgg cgc acc ttc gtg ctg cgt gtg cgg gcc cag gac ccg ccg cct gag    2170
Trp Arg Thr Phe Val Leu Arg Val Arg Ala Gln Asp Pro Pro Pro Glu
690                 695                 700                 705
ctg tac ttt gtc aag gtg gat gtg acg ggc gcg tac gac acc atc ccc    2218
Leu Tyr Phe Val Lys Val Asp Val Thr Gly Ala Tyr Asp Thr Ile Pro
                710                 715                 720
cag gac agg ctc acg gag gtc atc gcc agc atc atc aaa ccc cag aac    2266
Gln Asp Arg Leu Thr Glu Val Ile Ala Ser Ile Ile Lys Pro Gln Asn
            725                 730                 735
acg tac tgc gtg cgt cgg tat gcc gtg gtc cag aag gcc gcc cat ggg    2314
Thr Tyr Cys Val Arg Arg Tyr Ala Val Val Gln Lys Ala Ala His Gly
        470                 745                 750
cac gtc cgc aag gcc ttc aag agc cac gtc tct acc ttg aca gac ctc    2362
His Val Arg Lys Ala Phe Lys Ser His Val Ser Thr Leu Thr Asp Leu
    755                 760                 765
cag ccg tac atg cga cag ttc gtg gct cac ctg cag gag acc agc ccg    2410
Gln Pro Tyr met Arg Gln Phe Val Ala His Leu Gln Glu Thr Ser Pro
770                 775                 780                 785
ctg agg gat gcc gtc gtc atc gag cag agc tcc tcc ctg aat gag gcc    2458
Leu Arg Asp Ala Val Val Ile Glu Gln Ser Ser Ser Leu Asn Glu Ala
                790                 795                 800
agc agt ggc ctc ttc gac gtc ttc cta cgc ttc atg tgc cac cac gcc    2506
Ser Ser Gly Leu Phe Asp Val Phe Leu Arg Phe Met Cys His His Ala
            805                 810                 815
gtg cgc atc agg ggc aag tcc tac gtc cag tgc cag ggg atc ccg cag    2554
Val Arg Ile Arg Gly Lys Ser Tyr Val Gln Cys Gln Gly Ile Pro Gln
        820                 825                 830
ggc tcc atc ctc tcc acg ctg ctc tgc agc ctg tgc tac ggc gac atg    2602
Gly Ser Ile Leu Ser Thr Leu Leu Cys Ser Leu Cys Tyr Gly Asp met
    835                 840                 845
gag aac aag ctg ttt gcg ggg att cgg cgg gac ggg ctg ctc ctg cgt    2650
Glu Asn Lys Leu Phe Ala Gly Ile Arg Arg Asp Gly Leu Leu Leu Arg
850                 855                 860                 865
ttg gtg gat gat ttc ttg ttg gtg aca cct cac ctc acc cac gcg aaa    2698
Leu Val Asp Asp Phe Leu Leu Val Thr Pro His Leu Thr His Ala Lys
                870                 875                 880
```

FIG. 1D

```
acc ttc ctc agg acc ctg gtc cga ggt gtc cct gag tat ggc tgc gtg    2746
Thr Phe Leu Arg Thr Leu Val Arg Gly Val Pro Glu Tyr Gly Cys Val
            885                 890                 895
gtg aac ttg cgg aag aca gtg gtg aac ttc cct gta gaa gac gag gcc    2794
Val Asn Leu Arg Lys Thr Val Val Asn Phe Pro Val Glu Asp Glu Ala
        900                 905                 910
ctg ggt ggc acg gct ttt gtt cag atg ccg gcc cac ggc cta ttc ccc    2842
Leu Gly Gly Thr Ala Phe Val Gln met Pro Ala His Gly Leu Phe Pro
    915                 920                 925
tgg tgc ggc ctg ctg ctg gat acc cgg acc ctg gag gtg cag agc gac    2890
Trp Cys Gly Leu Leu Leu Asp Thr Arg Thr Leu Glu Val Gln Ser Asp
930                 935                 940                 945
tac tcc agc tat gcc cgg acc tcc atc aga gcc agt ctc acc ttc aac    2938
Tyr Ser Ser Tyr Ala arg Thr Ser Ile Arg Ala Ser Leu Thr Phe Asn
                950                 955                 960
cgc ggc ttc aag gct ggg agg aac atg cgt cgc aaa ctc ttt ggg gtc    2986
Arg Gly Phe Lys Ala Gly Arg Asn Met Arg Arg Lys Leu Phe Gly Val
            965                 970                 975
ttg cgg ctg aag tgt cac agc ctg ttt ctg gat ttg cag gtg aac agc    3034
Leu Arg Leu Lys Cys His Ser Leu Phe Leu Asp Leu Gln Val Asn Ser
        980                 985                 990
ctc cag acg gtg tgc acc aac atc tac aag atc ctc ctg ctg cag gcg    3082
Leu Gln Thr Val Cys Thr Asn Ile Tyr Lys Ile Leu Leu Leu Gln Ala
    995                 1000                1005
tac agg ttt cac gca tgt gtg ctg cag ctc cca ttt cat cag caa gtt    3130
Tyr Arg Phe His Ala Cys Val Leu Gln Leu Pro Phe His Gln Gln Val
1010                1015                1020                1025
tgg aag aac ccc aca ttt ttc ctg cgc gtc atc tct gac acg gcc tcc    3178

Leu Cys Tyr Ser Ile Leu Lys Ala Lys Asn Ala Gly Met Ser Leu Gly
                1045                1050                1055
gcc aag ggc gcc gcc ggc cct ctg ccc tcc gag gcc gtg cag tgg ctg    3274
Ala Lys Gly Ala Ala Gly Pro Leu Pro Ser Glu Ala Val Gln Trp Leu
        1060                1065                1070
tgc cac caa gca ttc ctg ctc aag ctg act cga cac cgt gtc acc tac    3322
Cys His Gln Ala Phe Leu Leu Lys Leu Thr Arg His Arg Val Thr Tyr
    1075                1080                1085
gtg cca ctc ctg ggg tca ctc agg aca gcc cag acg cag ctg agt cgg    3370
Val Pro Leu Leu Gly Ser Leu Arg Thr Ala Gln Thr Gln Leu Ser Arg
1090                1095                1100                1105
```

FIG. 1E

```
aag ctc ccg ggg acg acg ctg act gcc ctg gag gcc gca gcc aac ccg    3418
Lys Leu Pro Gly Thr Thr Leu Thr Ala Leu Glu Ala Ala Ala Asn Pro
            1110             1115                1120
gca ctg ccc tca gac ttc aag acc atc ctg gac tga tggccacccg          3464
Ala Leu Pro Ser Asp Phe Lys Thr Ile Leu Asp
        1125                 1130 cccacagcca ggccgagagc agacaccagc agccctgtca cgccgggctc tacgtcccag   3524
ggagggaggg gcggcccaca cccaggcccg caccgctggg agtctgaggc ctgagtgagt   3584
gtttggccga ggcctgcatg tccggctgaa ggctgagtgt ccggctgagg cctgagcgag   3644
tgtccagcca agggctgagt gtccagcaca cctgccgtct tcacttcccc acaggctggc   3704
gctcggctcc accccagggc cagcttttcc tcaccaggag cccggcttcc actccccaca   3764
taggaatagt ccatccccag attcgccatt gttcacccct cgccctgccc tcctttgcct   3824
tccaccccca ccatccaggt ggagaccctg agaaggaccc tgggagctct gggaatttgg   3884
agtgaccaaa ggtgtgccct gtacacaggc gaggaccctg cacctggatg ggggtccctg   3944
tgggtcaaat tgggggggagg tgctgtggga gtaaaatact gaatatatga gttttcagt   4004
tttgaaaaaa a                                                        4015
```

FIG. 1F

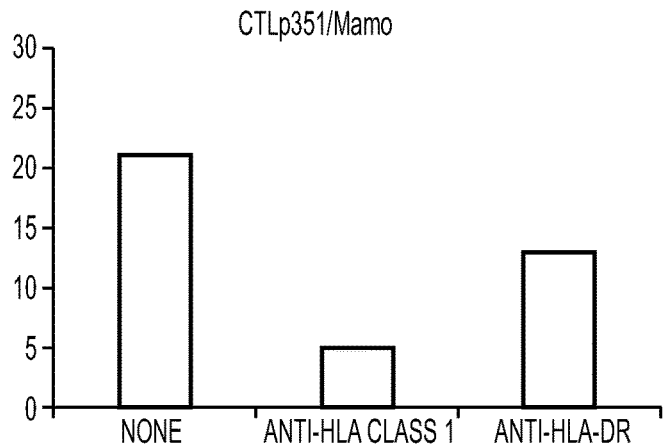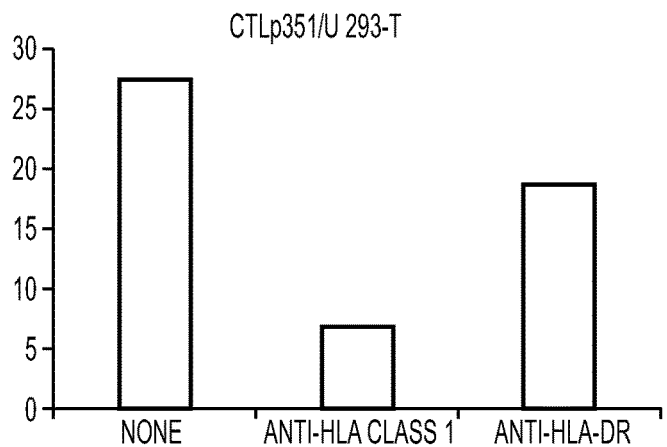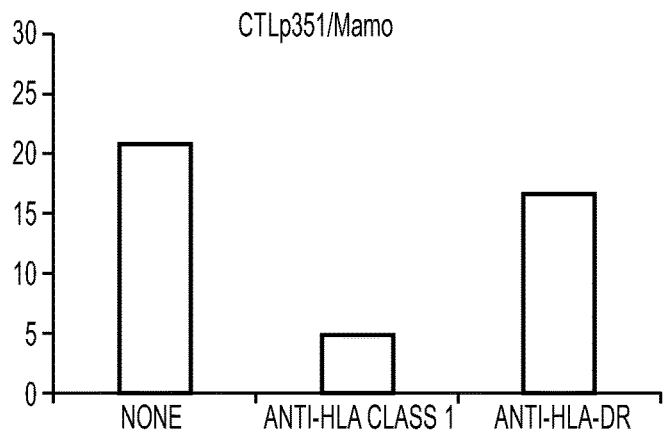
FIG. 4

```
caggcagcgc tgcgtcctgc tgcgcacgtg ggaagccctg gccccggcca ccccgcg          58 atg ccg cgc gct ccc cgc tgc cga gcc gtg cgc tcc ctg ctg cgc agc         106
Met Pro Arg Ala Pro Arg Cys Arg Ala Val Arg Ser Leu Leu Arg Ser
1               5                   10                  15 cac tac cgc gag gtg ctg ccg ctg gcc acg ttc gtg cgg cgc ctg ggg         154
His Tyr Arg Glu Val Leu Pro Leu Ala Thr Phe Val Arg Arg Leu Gly
                20                  25                  30 ccc cag ggc tgg cgg ctg gtg cag cgc ggg gac ccg gcg gct ttc cgc         202
Pro Gln Gly Trp Arg Leu Val Gln Arg Gly Asp Pro Ala Ala Phe Arg
            35                  40                  45 gcg ctg gtg gcc cag tgc ctg gtg tgc gtg ccc tgg gac gca cgg ccg         250
Ala Leu Val Ala Gln Cys Leu Val Cys Val Pro Trp Asp Ala Arg Pro
        50                  55                  60 ccc ccc gcc gcc ccc tcc ttc cgc cag gtg tcc tgc ctg aag gag ctg         298
Pro Pro Ala Ala Pro Ser Phe Arg Gln Val Ser Cys Leu Lys Glu Leu
65                  70                  75                  80 gtg gcc cga gtg ctg cag agg ctg tgc gag cgc ggc gcg aag aac gtg         346
Val Ala Arg Val Leu Gln Arg Leu Cys Glu Arg Gly Ala Lys Asn Val
                85                  90                  95 ctg gcc ttc ggc ttc gcg ctg ctg gac ggg gcc cgc ggg ggc ccc ccc         394
Leu Ala Phe Gly Phe Ala Leu Leu Asp Gly Ala Arg Gly Gly Pro Pro
            100                 105                 110 gag gcc ttc acc acc agc gtg cgc agc tac ctg ccc aac acg gtg acc         442
Glu Ala Phe Thr Thr Ser Val Arg Ser Tyr Leu Pro Asn Thr Val Thr
        115                 120                 125 gac gca ctg cgg ggg agc ggg gcg tgg ggg ctg ctg cgc cgc gtg              490
Asp Ala Leu Arg Gly Ser Gly Ala Trp Gly Leu Leu Arg Arg Val
    130                 135                 140 ggc gac gac gtg ctg gtt cac ctg ctg gca cgc tgc gcg ctc ttt gtg         538
Gly Asp Asp Val Leu Val His Leu Leu Ala Arg Cys Ala Leu Phe Val
145                 150                 155                 160 ctg gtg gct ccc agc tgc gcc tac cag gtg tgc ggg ccg ccg ctg tac         586
Leu Val Ala Pro Ser Cys Ala Tyr Gln Val Cys Gly Pro Pro Leu Tyr
                165                 170                 175 cag ctc ggc gct gcc act cag gcc cgg ccc ccg cca cac gct agt gga         634
Gln Leu Gly Ala Ala Thr Gln Ala Arg Pro Pro Pro His Ala Ser Gly
            180                 185                 190 ccc cga agg cgt ctg gga tgc gaa cgg gcc tgg aac cat agc gtc agg         682
Pro Arg Arg Arg Leu Gly Cys Glu Arg Ala Trp Asn His Ser Val Arg
        195                 200                 205 gag gcc ggg gtc ccc ctg ggc ctg cca gcc ccg ggt gcg agg agg cgc         730
Glu Ala Gly Val Pro Leu Gly Leu Pro Ala Pro Gly Ala Arg Arg Arg
    210                 215                 220
```

FIG. 9A

```
ggg ggc agt gcc agc cga agt ctg ccg ttg ccc aag agg ccc agg cgt    778
Gly Gly Ser Ala Ser Arg Ser Leu Pro Leu Pro Lys Arg Pro Arg Arg
225             230                 235                 240
ggc gct gcc cct gag ccg gag cgg acg ccc gtt ggg cag ggg tcc tgg    826
Gly Ala Ala Pro Glu Pro Glu Arg Thr Pro Val Gly Gln Gly Ser Trp
                245                 250                 255
gcc cac ccg ggc agg acg cgt gga ccg agt gac cgt ggt ttc tgt gtg    874
Ala His Pro Gly Arg Thr Arg Gly Pro Ser Asp Arg Gly Phe Cys Val
            260                 265                 270
gtg tca cct gcc aga ccc gcc gaa gaa gcc acc tct ttg gag ggt gcg    922
Val Ser Pro Ala Arg Pro Ala Glu Glu Ala Thr Ser Leu Glu Gly Ala
        275                 280                 285
ctc tct ggc acg cgc cac tcc cac cca tcc gtg ggc cgc cag cac cac    970
Leu Ser Gly Thr Arg His Ser His Pro Ser Val Gly Arg Gln His His
    290                 295                 300
gcg ggc ccc cca tcc aca tcg cgg cca cca cgt ccc tgg gac acg cct   1018
Ala Gly Pro Pro Ser Thr Ser Arg Pro Pro Arg Pro Trp Asp Thr Pro
305                 310                 315                 320
tgt ccc ccg gtg tac gcc gag acc aag cac ttc ctc tac tcc tca ggc   1066
Cys Pro Pro Val Tyr Ala Glu Thr Lys His Phe Leu Tyr Ser Ser Gly
                325                 330                 335
gac aag gag cag ctg cgg ccc tcc ttc cta ctc agc tct ctg agg ccc   1114
Asp Lys Glu Gln Leu Arg Pro Ser Phe Leu Leu Ser Ser Leu Arg Pro
            340                 345                 350
agc ctg act ggc gct cgg agg ctc gtg gag acc atc ttt ctg ggt tcc   1162
Ser Leu Thr Gly Ala Arg Arg Leu Val Glu Thr Ile Phe Leu Gly Ser
        355                 360                 365
agg ccc tgg atg cca ggg act ccc cgc agg ttg ccc cgc ctg ccc cag   1210
Arg Pro Trp Met Pro Gly Thr Pro Arg Arg Leu Pro Arg Leu Pro Gln
    370                 375                 380
cgc tac tgg caa atg cgg ccc ctg ttt ctg gag ctg ctt ggg aac cac   1258
Arg Tyr Trp Gln Met Arg Pro Leu Phe Leu Glu Leu Leu Gly Asn His
385                 390                 395                 400
gcg cag tgc ccc tac ggg gtg ctc ctc aag acg cac tgc ccg ctg cga   1306
Ala Gln Cys Pro Tyr Gly Val Leu Leu Lys Thr His Cys Pro Leu Arg
                405                 410                 415
gct gcg gtc acc cca gca gcc ggt gtc tgt gcc cgg gag aag ccc cag   1354
Ala Ala Val Thr Pro Ala Ala Gly Val Cys Ala Arg Glu Lys Pro Gln
            420                 425                 430
ggc tct gtg gcg gcc ccc gag gag gag gac aca gac ccc cgt cgc ctg   1402
Gly Ser Val Ala Ala Pro Glu Glu Glu Asp Thr Asp Pro Arg Arg Leu
        435                 440                 445
```

*FIG. 9B*

```
gtg cag ctg ctc cgc cag cac agc agc ccc tgg cag gtg tac ggc ttc    1450
Val Gln Leu Leu Arg Gln His Ser Ser Pro Trp Gln Val Tyr Gly Phe
    450                 455                 460 gtg cgg gcc tgc ctg cgc cgg ctg gtg ccc cca ggc ctc tgg ggc tcc    1498
Val Arg Ala Cys Leu Arg Arg Leu Val Pro Pro Gly Leu Trp Gly Ser
465                 470                 475                 480 agg cac aac gaa cgc cgc ttc ctc agg aac acc aag aag ttc atc tcc    1546
Arg His Asn Glu Arg Arg Phe Leu Arg Asn Thr Lys Lys Phe Ile Ser
                485                 490                 495 ctg ggg aag cat gcc aag ctc tcg ctg cag gag ctg acg tgg aag atg    1594
Leu Gly Lys His Ala Lys Leu Ser Leu Gln Glu Leu Thr Trp Lys Met
            500                 505                 510 agc gtg cgg gac tgc gct tgg ctg cgc agg agc cca ggg gtt ggc tgt    1642
Ser Val Arg Asp Cys Ala Trp Leu Arg Arg Ser Pro Gly Val Gly Cys
        515                 520                 525 gtt ccg gcc gca gag cac cgt ctg cgt gag gag atc ctg gcc aag ttc    1690
Val Pro Ala Ala Glu His Arg Leu Arg Glu Glu Ile Leu Ala Lys Phe
    530                 535                 540 ctg cac tgg ctg atg agt gtg tac gtc gtc gag ctg ctc agg tct ttc    1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac    1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac    1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag    1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc    1930
His Arg Glu Ala Arg Pro Ala Leu Leu Thr Ser Arg Leu Arg Phe Ile
    610                 615                 620 ccc aag cct gac ggg ctg cgg ccg att gtg aac atg gac tac gtc gtg    1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg    2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc    2074
Arg Val Lys Ala Leu Phe Ser Val Leu Asn Tyr Glu Arg Ala Arg Arg
            660                 665                 670
```

*FIG. 9C*

```
ccc ggc ctc ctg ggc gcc tct gtg ctg ggc ctg gac gat atc cac agg      2122
Pro Gly Leu Leu Gly Ala Ser Val Leu Gly Leu Asp Asp Ile His Arg
        675                 680                 685
gcc tgg cgc acc ttc gtg ctg cgt gtg cgg gcc cag gac ccg ccg cct      2170
Ala Trp Arg Thr Phe Val Leu Arg Val Arg Ala Gln Asp Pro Pro Pro
        690                 695                 700
gag ctg tac ttt gtc aag gtg gat gtg acg ggc gcg tac gac acc atc      2218
Glu Leu Tyr Phe Val Lys Val Asp Val Thr Gly Ala Tyr Asp Thr Ile
705                 710                 715                 720
ccc cag gac agg ctc acg gag gtc atc gcc agc atc atc aaa ccc cag      2266
Pro Gln Asp Arg Leu Thr Glu Val Ile Ala Ser Ile Ile Lys Pro Gln
                725                 730                 735
aac acg tac tgc gtg cgt cgg tat gcc gtg gtc cag aag gcc gcc cat      2314
Asn Thr Tyr Cys Val Arg Arg Tyr Ala Val Val Gln Lys Ala Ala His
                740                 745                 750
ggg cac gtc cgc aag gcc ttc aag agc cac gtc tct acc ttg aca gac      2362
Gly His Val Arg Lys Ala Phe Lys Ser His Val Ser Thr Leu Thr Asp
            755                 760                 765
ctc cag ccg tac atg cga cag ttc gtg gct cac ctg cag gag acc agc      2410
Leu Gln Pro Tyr Met Arg Gln Phe Val Ala His Leu Gln Glu Thr Ser
        770                 775                 780
ccg ctg agg gat gcc gtc gtc atc gag cag agc tcc tcc ctg aat gag      2458
Pro Leu Arg Asp Ala Val Val Ile Glu Gln Ser Ser Ser Leu Asn Glu
785                 790                 795                 800
gcc agc agt ggc ctc ttc gac gtc ttc cta cgc ttc atg tgc cac cac      2506
Ala Ser Ser Gly Leu Phe Asp Val Phe Leu Arg Phe Met Cys His His
                805                 810                 815
gcc gtg cgc atc agg ggc aag tcc tac gtc cag tgc cag ggg atc ccg      2554
Ala Val Arg Ile Arg Gly Lys Ser Tyr Val Gln Cys Gln Gly Ile Pro
                820                 825                 830
cag ggc tcc atc ctc tcc acg ctg ctc tgc agc ctg tgc tac ggc gac      2602
Gln Gly Ser Ile Leu Ser Thr Leu Leu Cys Ser Leu Cys Tyr Gly Asp
            835                 840                 845
atg gag aac aag ctg ttt gcg ggg att cgg cgg gac ggg ctg ctc ctg      2650
Met Glu Asn Lys Leu Phe Ala Gly Ile Arg Arg Asp Gly Leu Leu Leu
        850                 855                 860
cgt ttg ttc ttg ttg gtg aca cct cac ctc acc cac gcg aaa acc ttc      2698
Arg Leu Phe Leu Leu Val Thr Pro His Leu Thr His Ala Lys Thr Phe
865                 870                 875                 880
ctc agg acc ctg gtc cga ggt gtc cct gag tat ggc tgc gtg gtg aac      2746
Leu Arg Thr Leu Val Arg Gly Val Pro Glu Tyr Gly Cys Val Val Asn
                885                 890                 895
```

FIG. 9D

```
ttg cgg aag aca gtg gtg aac ttc cct gta gaa gac gag gcc ctg ggt    2794
Leu Arg Lys Thr Val Val Asn Phe Pro Val Glu Asp Glu Ala Leu Gly
            900             905                 910
ggc acg gct ttt gtt cag atg ccg gcc cac ggc cta ttc ccc tgg tgc    2842
Gly Thr Ala Phe Val Gln Met Pro Ala His Gly Leu Phe Pro Trp Cys
            915             920                 925
ggc ctg ctg ctg gat acc cgg acc ctg gag gtg cag agc gac tac tcc    2890
Gly Leu Leu Leu Asp Thr Arg Thr Leu Glu Val Gln Ser Asp Tyr Ser
            930             935                 940
agc tat gcc cgg acc tcc atc aga gcc agt ctc acc ttc aac cgc ggc    2938
Ser Tyr Ala Arg Thr Ser Ile Arg Ala Ser Leu Thr Phe Asn Arg Gly
945             950             955                 960
ttc aag gct ggg agg agc atg cgt cgc aaa ctc ttt ggg gtc ttg cgg    2986
Phe Lys Ala Gly Arg Asn Met Arg Arg Lys Leu Phe Gly Val Leu Arg
                965             970                 975
ctg aag tgt cac agc ctg ttt ctg gat ttg cag gtg aac agc ctc cag    3034
Leu Lys Cys His Ser Leu Phe Leu Asp Leu Gln Val Asn Ser Leu Gln
                980             985                 990
acg gtg tgc acc aac atc tac aag  atc ctc ctg ctg cag  gcg tac agg  3082
Thr Val Cys Thr Asn Ile Tyr Lys  Ile Leu Leu Leu Gln  Ala Tyr Arg
                995              1000                1005
ttt cac  gca tgt gtg ctg cag  ctc cca ttt cat cag  caa gtt tgg     3127
Phe His  Ala Cys Val Leu Gln  Leu Pro Phe His Gln  Gln Val Trp
 1010                1015                 1020
aag aac  ccc aca ttt ttc ctg  cgc gtc atc tct gac  acg gcc tcc     3172
Lys Asn  Pro Thr Phe Phe Leu  Arg Val Ile Ser Asp  Thr Ala Ser
 1025                1030                 1035
ctc tgc  tac tcc atc ctg aaa  gcc aag aac gca ggg  atg tcg ctg     3217
Leu Cys  Tyr Ser Ile Leu Lys  Ala Lys Asn Ala Gly  Met Ser Leu
 1040                1045                 1050
ggg gcc  aag ggc gcc gcc ggc  cct ctg ccc tcc gag  gcc gtg cag     3262
Gly Ala  Lys Gly Ala Ala Gly  Pro Leu Pro Ser Glu  Ala Val Gln
 1055                1060                 1065
tgg ctg  tgc cac caa gca ttc  ctg ctc aag ctg act  cga cac cgt     3307
Trp Leu  Cys His Gln Ala Phe  Leu Leu Lys Leu Thr  Arg His Arg
 1070                1075                 1080
gtc acc  tac gtg cca ctc ctg  ggg tca ctc agg aca  gcc cag acg     3352
Val Thr  Tyr Val Pro Leu Leu  Gly Ser Leu Arg Thr  Ala Gln Thr
 1085                1090                 1095
cag ctg  agt cgg aag ctc ccg  ggg acg acg ctg act  gcc ctg gag     3397
Gln Leu  Ser Arg Lys Leu Pro  Gly Thr Thr Leu Thr  Ala Leu Glu
 1100                1105                 1110
```

*FIG. 9E*

| | | | | | | | | | | | | |
|---|---|---|---|---|---|---|---|---|---|---|---|---|
| gcc | gca | gcc | aac | ccg | gca | ctg | ccc | tca | gac | ttc | aag | acc atc ctg | 3442 |
| Ala | Ala | Ala | Asn | Pro | Ala | Leu | Pro | Ser | Asp | Phe | Lys | Thr Ile Leu |
| | 1115 | | | | 1120 | | | | | 1125 | | | gac tga tggccacccg cccacagcca ggccgagagc agacaccagc agccctgtca 3498
Asp cgccgggctc tacgtcccag ggagggaggg gcggcccaca cccaggcccg caccgctggg 3558
agtctgaggc ctgagtgagt gtttggccga ggcctgcatg tccggctgaa ggctgagtgt 3618
ccggctgagg cctgagcgag tgtccagcca agggctgagt gtccagcaca cctgccgtct 3678
tcacttcccc acaggctggc gctcggctcc accccagggc cagcttttcc tcaccaggag 3738
cccggcttcc actccccaca taggaatagt ccatccccag attcgccatt gttcacccct 3798
cgccctgccc tcctttgcct tccaccccca ccatccaggt ggagaccctg agaaggaccc 3858
tgggagctct gggaatttgg agtgaccaaa ggtgtgccct gtacacaggc gaggaccctg 3918
cacctggatg ggggtccctg tgggtcaaat tgggggggagg tgctgtggga gtaaaatact 3978
gaatatatga gtttttcagt tttgaaaaaa a 4009

FIG. 9F

```
        caggcagcgc tgcgtcctgc tgcgcacgtg ggaagccctg gccccggcca ccccgcg      58 atg ccg cgc gct ccc cgc tgc cga gcc gtg cgc tcc ctg ctg cgc agc             106
Met Pro Arg Ala Pro Arg Cys Arg Ala Val Arg Ser Leu Leu Arg Ser
1               5                   10                  15 cac tac cgc gag gtg ctg ccg ctg gcc acg ttc gtg cgg cgc ctg ggg             154
His Tyr Arg Glu Val Leu Pro Leu Ala Thr Phe Val Arg Arg Leu Gly
                20                  25                  30 ccc cag ggc tgg cgg ctg gtg cag cgc ggg gac ccg gcg gct ttc cgc             202
Pro Gln Gly Trp Arg Leu Val Gln Arg Gly Asp Pro Ala Ala Phe Arg
            35                  40                  45 gcg ctg gtg gcc cag tgc ctg gtg tgc gtg ccc tgg gac gca cgg ccg             250
Ala Leu Val Ala Gln Cys Leu Val Cys Val Pro Trp Asp Ala Arg Pro
        50                  55                  60 ccc ccc gcc gcc ccc tcc ttc cgc cag gtg tcc tgc ctg aag gag ctg             298
Pro Pro Ala Ala Pro Ser Phe Arg Gln Val Ser Cys Leu Lys Glu Leu
65                  70                  75                  80 gtg gcc cga gtg ctg cag agg ctg tgc gag cgc ggc gcg aag aac gtg             346
Val Ala Arg Val Leu Gln Arg Leu Cys Glu Arg Gly Ala Lys Asn Val
                85                  90                  95 ctg gcc ttc ggc ttc gcg ctg ctg gac ggg gcc cgc ggg ggc ccc ccc             394
Leu Ala Phe Gly Phe Ala Leu Leu Asp Gly Ala Arg Gly Gly Pro Pro
                100                 105                 110 gag gcc tcc acc acc agc gtg cgc agc tac ctg ccc aac acg gtg acc             442
Glu Ala Ser Thr Thr Ser Val Arg Ser Tyr Leu Pro Asn Thr Val Thr
            115                 120                 125 gac gca ctg cgg ggg agc ggg gcg tgg ggg ctg ctg ctg cgc cgc gtg             490
Asp Ala Leu Arg Gly Ser Gly Ala Trp Gly Leu Leu Leu Arg Arg Val
        130                 135                 140 ggc gac gac gtg ctg gtt cac ctg ctg gca cgc tgc gcg ctc ttt gtg             538
Gly Asp Asp Val Leu Val His Leu Leu Ala Arg Cys Ala Leu Phe Val
145                 150                 155                 160 ctg gtg gct ccc agc tgc gcc tac cag gtg tgc ggg ccg ccg ctg tac             586
Leu Val Ala Pro Ser Cys Ala Tyr Gln Val Cys Gly Pro Pro Leu Tyr
                165                 170                 175 cag ctc ggc gct gcc act cag gcc cgg ccc ccg cca cac gct agt gga             634
Gln Leu Gly Ala Ala Thr Gln Ala Arg Pro Pro Pro His Ala Ser Gly
                180                 185                 190 ccc cga agg cgt ctg gga tgc gaa cgg gcc tgg acc cat agc gtc agg             682
Pro Arg Arg Arg Leu Gly Cys Glu Arg Ala Trp Asn His Ser Val Arg
            195                 200                 205
```

*FIG. 10A*

```
gag gcc ggg gtc ccc ctg ggc ctg cca gcc ccg ggt gcg agg agg cgc    730
Glu Ala Gly Val Pro Leu Gly Leu Pro Ala Pro Gly Ala Arg Arg Arg
    210                 215                 220
ggg ggc agt gcc agc cga agt ctg ccg ttg ccc aag agg ccc agg cgt    778
Gly Gly Ser Ala Ser Arg Ser Leu Pro Leu Pro Lys Arg Pro Arg Arg
225                 230                 235                 240
ggc gct gcc cct gag ccg gag cgg acg ccc gtt ggg cag ggg tcc tgg    826
Gly Ala Ala Pro Glu Pro Glu Arg Thr Pro Val Gly Gln Gly Ser Trp
                245                 250                 255
gcc cac ccg ggc agg acg cgt gga ccg agt gac cgt ggt ttc tgt gtg    874
Ala His Pro Gly Arg Thr Arg Gly Pro Ser Asp Arg Gly Phe Cys Val
            260                 265                 270
gtg tca cct gcc aga ccc gcc gaa gaa gcc acc tct ttg gag ggt gcg    922
Val Ser Pro Ala Arg Pro Ala Glu Glu Ala Thr Ser Leu Glu Gly Ala
        275                 280                 285
ctc tct ggc acg cgc cac tcc cac cca tcc gtg ggc cgc cag cac cac    970
Leu Ser Gly Thr Arg His Ser His Pro Ser Val Gly Arg Gln His His
    290                 295                 300
gcg ggc ccc cca tcc aca tcg cgg cca cca cgt ccc tgg gac acg cct    1018
Ala Gly Pro Pro Ser Thr Ser Arg Pro Pro Arg Pro Trp Asp Thr Pro
305                 310                 315                 320
tgt ccc ccg gtg tac gcc gag acc aag cac ttc ctc tac tcc tca ggc    1066
Cys Pro Pro Val Tyr Ala Glu Thr Lys His Phe Leu Tyr Ser Ser Gly
                325                 330                 335
gac aag gag cag ctg cgg ccc tcc ttc cta ctc agc tct ctg agg ccc    1114
Asp Lys Glu Gln Leu Arg Pro Ser Phe Leu Leu Ser Ser Leu Arg Pro
            340                 345                 350
agc ctg act ggc gct cgg agg ctc gtg gag acc atc ttt ctg ggt tcc    1162
Ser Leu Thr Gly Ala Arg Arg Leu Val Glu Thr Ile Phe Leu Gly Ser
        355                 360                 365
agg ccc tgg atg cca ggg act ccc cgc agg ttg ccc cgc ctg ccc cag    1210
Arg Pro Trp Met Pro Gly Thr Pro Arg Arg Leu Pro Arg Leu Pro Gln
    370                 375                 380
cgc tac tgg caa atg cgg ccc ctg ttt ctg gag ctg ctt ggg aac cac    1258
Arg Tyr Trp Gln Met Arg Pro Leu Phe Leu Glu Leu Leu Gly Asn His
385                 390                 395                 400
gcg cag tgc ccc tac ggg gtg ctc ctc aag acg cac tgc ccg ctg cga    1306
Ala Gln Cys Pro Tyr Gly Val Leu Leu Lys Thr His Cys Pro Leu Arg
                405                 410                 415
gct gcg gtc acc cca gca gcc ggt gtc tgt gcc cgg gag aag ccc cag    1354
Ala Ala Val Thr Pro Ala Ala Gly Val Cys Ala Arg Glu Lys Pro Gln
            420                 425                 430
```

FIG. 10B

```
ggc tct gtg gcg gcc ccc gag gag gag gac aca gac ccc cgt cgc ctg   1402
Gly Ser Val Ala Ala Pro Glu Glu Glu Asp Thr Asp Pro Arg Arg Leu
        435                 440                 445
gtg cag ctg ctc cgc cag cac agc agc ccc tgg cag gtg tac ggc ttc   1450
Val Gln Leu Leu Arg Gln His Ser Ser Pro Trp Gln Val Tyr Gly Phe
    450                 455                 460
gtg cgg gcc tgc ctg cgc cgg ctg gtg ccc cca ggc ctc tgg ggc tcc   1498
Val Arg Ala Cys Leu Arg Arg Leu Val Pro Pro Gly Leu Trp Gly Ser
465                 470                 475                 480
agg cac aac gaa cgc cgc ttc ctc agg aac acc aag aag ttc atc tcc   1546
Arg His Asn Glu Arg Arg Phe Leu Arg Asn Thr Lys Lys Phe Ile Ser
                485                 490                 495
ctg ggg aag cat gcc aag ctc tcg ctg cag gag ctg acg tgg aag atg    922
Leu Gly Lys His Ala Lys Leu Ser Leu Gln Glu Leu Thr Trp Lys Met
            500                 505                 510
agc gtg cgg gac tgc gct tgg ctg cgc agg agc cca ggg gtt ggc tgt   1642
Ser Val Arg Asp Cys Ala Trp Leu Arg Arg Ser Pro Gly Val Gly Cys
        515                 520                 525
gtt ccg gcc gca gag cac cgt ctg cgt gag gag atc ctg gcc aag ttc   1690
Val Pro Ala Ala Glu His Arg Leu Arg Glu Glu Ile Leu Ala Lys Phe
    530                 535                 540
ctg cac tgg ctg atg agt gtg tac gtc gtc gag ctg ctc agg tct ttc   1738
Leu His Trp Leu Met Ser Val Tyr Val Val Glu Leu Leu Arg Ser Phe
545                 550                 555                 560
ttt tat gtc acg gag acc acg ttt caa aag aac agg ctc ttt ttc tac   1786
Phe Tyr Val Thr Glu Thr Thr Phe Gln Lys Asn Arg Leu Phe Phe Tyr
                565                 570                 575
cgg aag agt gtc tgg agc aag ttg caa agc att gga atc aga cag cac   1834
Arg Lys Ser Val Trp Ser Lys Leu Gln Ser Ile Gly Ile Arg Gln His
            580                 585                 590
ttg aag agg gtg cag ctg cgg gag ctg tcg gaa gca gag gtc agg cag   1882
Leu Lys Arg Val Gln Leu Arg Glu Leu Ser Glu Ala Glu Val Arg Gln
        595                 600                 605
cat cgg gaa gcc agg ccc gcc ctg ctg acg tcc aga ctc cgc ttc atc   1930
His Arg Glu Ala Arg Pro Ala Leu Leu Thr Ser Arg Leu Arg Phe Ile
    610                 615                 620
ccc aag cct gac ggg ctg cgg ccg att gtg aac atg gac tac gtc gtg   1978
Pro Lys Pro Asp Gly Leu Arg Pro Ile Val Asn Met Asp Tyr Val Val
625                 630                 635                 640
gga gcc aga acg ttc cgc aga gaa aag agg gcc gag cgt ctc acc tcg   2026
Gly Ala Arg Thr Phe Arg Arg Glu Lys Arg Ala Glu Arg Leu Thr Ser
                645                 650                 655
```

*FIG. 10C*

```
agg gtg aag gca ctg ttc agc gtg ctc aac tac gag cgg gcg cgg cgc    2074
Arg Val Lys Ala Leu Phe Ser Val Leu Asn Tyr Glu Arg Ala Arg Arg
            660                 665                 670
ccc ggc ctc ctg ggc gcc tct gtg ctg ggc ctg gac gat atc cac agg    2122
Pro Gly Leu Leu Gly Ala Ser Val Leu Gly Leu Asp Asp Ile His Arg
            675                 680                 685
gcc tgg cgc acc ttc gtg ctg cgt gtg cgg gcc cag gac ccg ccg cct    2170
Ala Trp Arg Thr Phe Val Leu Arg Val Arg Ala Gln Asp Pro Pro Pro
            690                 695                 700
gag ctg tac ttt gtc aag gtg gat gtg acg ggc gcg tac gac acc atc    2218
Glu Leu Tyr Phe Val Lys Val Asp Val Thr Gly Ala Tyr Asp Thr Ile
705                 710                 715                 720
ccc cag gac agg ctc acg gag gtc atc gcc agc atc atc aaa ccc cag    2266
Pro Gln Asp Arg Leu Thr Glu Val Ile Ala Ser Ile Ile Lys Pro Gln
            725                 730                 735
aac acg tac tgc gtg cgt cgg tat gcc gtg gtc cag aag gcc gcc cat    2314
Asn Thr Tyr Cys Val Arg Arg Tyr Ala Val Val Gln Lys Ala Ala His
            740                 745                 750
ggg cac gtc cgc aag gcc ttc aag agc cac gtc tct acc ttg aca gac    2362
Gly His Val Arg Lys Ala Phe Lys Ser His Val Ser Thr Leu Thr Asp
            755                 760                 765
ctc cag ccg tac atg cga cag ttc gtg gct cac ctg cag gag acc agc    2410
Leu Gln Pro Tyr Met Arg Gln Phe Val Ala His Leu Gln Glu Thr Ser
            770                 775                 780
ccg ctg agg gat gcc gtc gtc atc gag cag agc tcc tcc ctg aat gag    2458
Pro Leu Arg Asp Ala Val Val Ile Glu Gln Ser Ser Ser Leu Asn Glu
785                 790                 795                 800
gcc agc agt ggc ctc ttc gac gtc ttc cta cgc ttc atg tgc cac cac    2506
Ala Ser Ser Gly Leu Phe Asp Val Phe Leu Arg Phe Met Cys His His
            805                 810                 815
gcc gtg cgc atc agg ggc aag tcc tac gtc cag tgc cag ggg atc ccg    2554
Ala Val Arg Ile Arg Gly Lys Ser Tyr Val Gln Cys Gln Gly Ile Pro
            820                 825                 830
cag ggc tcc atc ctc tcc acg ctg ctc tgc agc ctg tgc tac ggc gac    2602
Gln Gly Ser Ile Leu Ser Thr Leu Leu Cys Ser Leu Cys Tyr Gly Asp
            835                 840                 845
atg gag aac aag ctg ttt gcg ggg att cgg cgg gac ggg ctg ctc gtg    2650
Met Glu Asn Lys Leu Phe Ala Gly Ile Arg Arg Asp Gly Leu Leu Val
            850                 855                 860
aca cct cac ctc acc cac gcg aaa acc ttc ctc agg acc ctg gtc cga    2698
Thr Pro His Leu Thr His Ala Lys Thr Phe Leu Arg Thr Leu Val Arg
865                 870                 875                 880
```

*FIG. 10D*

```
ggt gtc cct gag tat ggc tgc gtg gtg aac ttg cgg aag aca gtg gtg    2746
Gly Val Pro Glu Tyr Gly Cys Val Val Asn Leu Arg Lys Thr Val Val
            885                 890                 895
aac ttc cct gta gaa gac gag gcc ctg ggt ggc acg gct ttt gtt cag    2794
Asn Phe Pro Val Glu Asp Glu Ala Leu Gly Gly Thr Ala Phe Val Gln
            900                 905                 910
atg ccg gcc cac ggc cta ttc ccc tgg tgc ggc ctg ctg ctg gat acc    2842
Met Pro Ala His Gly Leu Phe Pro Trp Cys Gly Leu Leu Leu Asp Thr
            915                 920                 925
cgg acc ctg gag gtg cag agc gac tac tcc agc tat gcc cgg acc tcc    2890
Arg Thr Leu Glu Val Gln Ser Asp Tyr Ser Ser Tyr Ala Arg Thr Ser
            930                 935                 940
atc aga gcc agt ctc acc ttc aac cgc ggc ttc aag gct ggg agg aac    2938
Ile Arg Ala Ser Leu Thr Phe Asn Arg Gly Phe Lys Ala Gly Arg Asn
945                 950                 955                 960
atg cgt cgc aaa ctc ttt ggg gtc ttg cgg ctg aag tgt cac agc ctg    2986
Met Arg Arg Lys Leu Phe Gly Val Leu Arg Leu Lys Cys His Ser Leu
            965                 970                 975
ttt ctg gat ttg cag gtg aac agc ctc cag acg gtg tgc acc acc atc    3034
Phe Leu Asp Leu Gln Val Asn Ser Leu Gln Thr Val Cys Thr Asn Ile
            980                 985                 990
tac aag atc ctc ctg ctg cag gcg  tac agg ttt cac gca  tgt gtg ctg  3082
Tyr Lys Ile Leu Leu Leu Gln Ala  Tyr Arg Phe His Ala  Cys Val Leu
            995                 1000                1005
cag ctc  cca ttt cat cag caa  gtt tgg aag aac ccc  aca ttt ttc     3127
Gln Leu  Pro Phe His Gln Gln  Val Trp Lys Asn Pro  Thr Phe Phe
    1010                1015                 1020
ctg cgc  gtc atc tct gac acg  gcc tcc ctc tgc tac  tcc atc ctg     3172
Leu Arg  Val Ile Ser Asp Thr  Ala Ser Leu Cys Tyr  Ser Ile Leu
    1025                1030                 1035
aaa gcc  aag aac gca ggg atg   tcg ctg ggg gcc aag   ggc gcc gcc   3217
Lys Ala  Lys Asn Ala Gly Met   Ser Leu Gly Ala Lys   Gly Ala Ala
    1040                1045                 1050
ggc cct  ctg ccc tcc gag gcc   gtg cag tgg ctg tgc  cac caa gca    3262
Gly Pro  Leu Pro Ser Glu Ala   Val Gln Trp Leu Cys  His Gln Ala
    1055                1060                 1065
ttc ctg  ctc aag ctg act cga  cac cgt gtc acc tac  gtg cca ctc     3307
Phe Leu  Leu Lys Leu Thr Arg  His Arg Val Thr Tyr  Val Pro Leu
    1070                1075                 1080
ctg ggg  tca ctc agg aca gcc  cag acg cag ctg agt  cgg aag ctc     3352
Leu Gly  Ser Leu Arg Thr Ala  Gln Thr Gln Leu Ser  Arg Lys Leu
    1085                1090                 1095
```

*FIG. 10E*

```
ccg ggg  acg acg ctg act gcc  ctg gag gcc gca gcc  aac ccg gca        3397
Pro Gly  Thr Thr Leu Thr Ala  Leu Glu Ala Ala Ala  Asn Pro Ala
    1100              1105                  1110 ctg ccc  tca gac ttc aag acc  atc ctg gac tga tggccacccg              3440
Leu Pro  Ser Asp Phe Lys Thr  Ile Leu Asp
    1115              1120 cccacagcca ggccgagagc agacaccagc agccctgtca cgccgggctc tacgtcccag     3500
ggagggaggg gcggcccaca cccaggcccg caccgctggg agtctgaggc ctgagtgagt     3560
gtttggccga ggcctgcatg tccggctgaa ggctgagtgt ccggctgagg cctgagcgag     3620
tgtccagcca agggctgagt gtccagcaca cctgccgtct tcacttcccc acaggctggc     3680
gctcggctcc accccagggc cagcttttcc tcaccaggag cccggcttcc actccccaca     3740
taggaatagt ccatccccag attcgccatt gttcacccct cgccctgccc tcctttgcct     3800
tccacccca  ccatccaggt ggagaccctg agaaggaccc tgggagctct gggaatttgg     3860
agtgaccaaa ggtgtgccct gtacacaggc gaggaccctg cacctggatg ggggtccctg     3920
tgggtcaaat tggggggagg tgctgtggga gtaaaatact gaatatatga gtttttcagt     3980
tttgaaaaaa a                                                          3991
```

FIG. 10F

POLYNUCLEOTIDES ENCODING MHC CLASS I-RESTRICTED HTERT EPITOPES, ANALOGUES THEREOF OR POLYEPITOPES

CROSS REFERENCE TO RELATED APPLICATIONS

This application is a continuation of application Ser. No. 11/795,027, filed Dec. 17, 2009, which is the national phase entry of PCT/EP2006/007571, filed Jul. 31, 2006, which claimed priority of European Patent Application No. 05291627.7 filed Jul. 29, 2005. Both of those applications are hereby incorporated herein by reference in their entirety.

This invention relates to the field of anticancer therapy, and to the identification of immunogenic peptides derived from the human telomerase reverse transcriptase (hTERT). The present invention relates to polynucleotides encoding hTERT epitopes restricted to MHC class I molecule, analogues thereof and polyepitopes containing such epitopes and/or analogues. Are also included in the present invention, vectors and cells comprising such polynucleotides. The present invention also concerns compositions comprising hTERT polypeptides, corresponding polynucleotides, vectors and cells, for use in the treatment and/or prevention of cancer.

In light of deficits in current anticancer therapeutic approaches, antitumor therapy has enjoyed renewed interest. Recent studies have enhanced our understanding of anti melanoma immune responses associated with tumor regression. Collectively these data suggest that activated tumor-specific CD8 CTL are immunological weapon of choice for potent anti-tumor therapy. The research of over-expressed proteins permitting to trigger cytotoxic T lymphocytes to tumours of different origins is also progressing.

Telomerase is a ribonucleoprotein complex, consisting of a protein component, TERT, and an RNA component (TR) containing the template for the synthesis of the repeat unit ($T_2AG_3$) added onto the ends of chromosomes, that stabilizes the chromosomes during replication and prevent end-to-end fusion. Maintenance of a constant telomere length prevents cells from aging, and confers immortality (Hahn et al. Nat Med 1999; 5: 1164-70). High hTERT activity was found in more than 85% of human cancers, whereas most normal adult human tissues show no or little telomerase activity (Counter et al. Blood 1995; 85:2315-20).

The widespread expression of telomerase in tumors indicates that peptide fragments of hTERT could serve as tumor specific antigen(s) and this has been confirmed in several reports (Vonderheide et al. immunity 1999; 10:673-9). Recent data from Phase I clinical trials demonstrate the feasibility of vaccine against hTERT in HLA-A2+ patients, opening the way for use of hTERT for therapeutic vaccination (Vonderheide et al. Clin Cancer Res 2004; 10:828-39; Parkhurst et al. Clin Cancer Res 2004; 10:4688-98). Nevertheless, the immunogenic hTERT peptides identified to date are restricted to one MHC allele HLA-A2.1, with only two initial reports on two HLA-supertypes, HLA-A3 and HLA-A24, represented respectively in 44.2% and 40% of the population.

Hence, the following publications reported the identification of hTRET peptides:

hTERT peptide ILAKFLHWL (SEQ ID NO: 1), restricted to HLA-A2 (Vonderheide et al. Immunity 1999; 10:673-9), hTERT peptides MPRAPRCRA (SEQ ID NO: 6), RPAEEATSL (SEQ ID NO: 6), RPSFLLSSL (SEQ ID NO: 10) and APRCRA VRS (SEQ ID NO: 2) identified by informatics prediction within the HLA-A context WO 00/02581). However, these peptides have never been confirmed by experimental results to be efficient epitopes, neither in a HLA-87 context nor in any HLA context.

hTERT peptide KLFGVLRLK (SEQ ID NO: 3) (K973), restricted to HLA-A3 (Vonderheide et al. Clin Cancer Res 2001; 7:3343-8), and hTERT peptides YAETKHFL (SEQ ID NO: 4) (TEL324) and VYGFVRACL (SEQ ID NO: 5) (TEL 461), restricted to HLA-A24 (Arai et al. Blood 2001; 9:2903-7).

Consequently, the hTERT peptides identified so far do not cover all the population, thus excluding a large segment of patients.

In order to overcome this failure, at least in part and to thus better cover the genetic diversity of the human population, the present invention identifies new epitopes derived from hTERT, restricted to a particular HLA which is different from HLA-A3 and HLA-A24. Among the many different alleles, the present application is interested in the HLA-B7 supertype which is expressed in about 25% of the population, and particularly to the second allele the most expressed in the human HLA-B population: the HLA-*B0702 (allele present in 15-20% of individuals in human population).

The gene of the isoform-1 of the telomerase is 4015 base pairs (bp) long (NCBI Accession number AF015950) and encodes a protein of 1132 amino acids (NCBI Accession number AAC51672.1) (FIG. 1).

The invention concerns a polynucleotide encoding a human telomerase reverse transcriptase (hTERT) peptide. In a particular embodiment of the invention, the encoded peptides are 9 amino acids in length (nonamer) or 10 amino acids in length (decamer), and the polynucleotide has hence 27 or 30 nucleotides. In general, the encoded peptide is less than 15 amino acids and the polynucleotide has less than 45 nucleotides.

The invention also concerns a polynucleotide encoding hTERT peptides that are epitopes, restricted to MHC class I molecule, especially epitopes suitable to induce an immune response restricted to HLA-87. The nucleotide sequence of the polynucleotide of the invention is, in a particular embodiment, limited to the sequence encoding the hTERT peptide. Such peptides can be chosen from the group consisting of MPRAPRCRA (SEQ ID NO: 6) (p1; amino acid residues 1 to 9), APRCRAVRSL (SEQ ID NO: 7) (p4; amino acid residues 4 to 13), APSFRQVSCL (SEQ ID NO: 8) (p68; amino acid residues 68 to 77), RPAEEATSL (SEQ ID NO: 9) (p277; amino acid residues 277 to 285), RPSFLLSSL (SEQ ID NO: 10) (p342; amino acid residues 342 to 350), RPSLTGARRL (SEQ ID NO: 11) (p351; amino acid residues 351 to 360), DPRRLVQLL (SEQ ID NO: 12) (p444, amino acid residues 444 to 452), FVRACLRRL (SEQ ID NO: 13) (p464, amino acid residues 464 to 472), AGRNMRRKL (SEQ ID NO: 14 (p966, amino acid residues 966 to 974), LPGTTLTAL (SEQ ID NO: 15) (p1107, amino acid residues 1107 to 1115) and LPSPKFTIL (SEQ ID NO: 16) (p1123, amino acid residues 1123 to 1131). All these polynucleotides may be used to induce a HLA-87-restricted immune response. In a particular embodiment, the invention especially concerns a polynucleotide encoding a HLA-87-restricted hTERT epitope, chosen from the group consisting of RPSL TGARRL (SEQ ID NO: 11) (p351), APSFRQVSCL (SEQ ID NO: 8) (p68), APRCRAVRSL (SEQ ID NO: 7) (p4), DPRRLVQLL (SEQ ID NO: 12) (p444), FVRACLRRL (SEQ ID NO: 13) (p464), AGRNMRRKL (SEQ ID NO: 14) (p966), LPGTTL TAL (SEQ ID NO: 15) (p1107) and h LPSPKFTIL (SEQ ID NO: 16) (p1123).

As defined herein, an "epitope" is an antigenic determinant, i.e. the peptide site recognized by cells of the immune system (immune cells) and especially the site necessary to elicit an immune response. The term epitope encompasses both linear epitope for which the consecutive amino acids (especially, 9 or 10) are recognized by immune cells and, conformational epitope for which immune cells recognize amino acids to the extent they adopt a proper configuration or conformation. Consequently, in some epitopes, the conformation (three dimensional structure) is as important as the amino acid sequence (primary structure).

The expression "MHC class 1-restricted" refers to the capacity for a particular peptide or epitope to have an affinity for a MHC (major histocompatibility complex) molecule of class I. Similarly, the expression "HLA-B7-restricted" refers to the capacity for a particular peptide or epitope to have an affinity for this type of HLA molecule.

Briefly, MHC genes encode cell surface polymorphic molecules that do not bind only foreign peptides but also can bind overexpressed or not self peptides or mutated self peptides, to display them on the cell surface of cell enabling their recognition by appropriate immune cells, especially T-cells. Said MHC molecules, referred to as H-2 in mice and HLA (Human Leucocyte Antigen) in humans, are classified as either class I molecules (designated HLA-A, B, or C) or class II molecules (designated DP, DQ or DR).

Accordingly, MHC class I molecules specifically bind CD8 molecules expressed on cytotoxic T lymphocytes (also named TCD8$^+$), whereas MHC class II molecules specifically bind CD4 molecules expressed on helper T lymphocytes (TCD4$^+$).

MHC class I molecules bind peptides derived from proteolytically degraded proteins especially endogenously synthesized proteins, by a cell. Small peptides obtained accordingly are transported into the endoplasmic reticulum where they associate with nascent MHC class i molecules before being routed through the Golgi apparatus and displayed on the cell surface for recognition by cytotoxic T lymphocytes.

In the present invention, the above-identified peptides have been shown on the one hand to bind either with high or medium affinity to MHC class I molecule, and on the other hand to be efficiently transported as a MHC/epitope complex to the cell surface of cells. In a preferred embodiment, the MHC class I molecule is an MHC allele of the HLA-B7 supertype family; the hTERT epitope is said HLA-B7 supertype-restricted. Said family encompasses alleles B0702, B0703, B0704, B0705, B1508, B3501, B3502, B3503, B51, B5301, B5401, B5501, B5502, B 5601, B5602, B6701 and B7801, family from which the HLA-B0702 is preferred (HLA-B0702-restricted hTERT epitope).

A MHC stabilization assay may be used to test the affinity of a peptide for a particular HLA class I molecule (relative avidity), such as the one described in Firat et al. (1999. Eur. J. of Immunol. 29: 3112-3121), incorporated herein by reference. Briefly, MHC class I molecule-transfected cells are incubated overnight at $2 \times 10^5$ cells/well in 96-well plates in serum free medium AIM-V (Invitrogen Corp., Gibco), supplemented with 100 ng/ml of human β2-microglobulin,
  in the absence of peptides (negative control),
  in the presence of a reference peptide (positive control), and
  in the presence of the peptides to be tested (hTERT peptides in the present case).
Peptides are incubated at various final concentrations ranging from 0.1 to 100 μM (with intermediate concentrations of 1 and 10 μM). The transfected cells are then labelled with a saturating concentration of an antibody recognizing the particular HLA MHC class I molecule, then washed twice and finally stained with a secondary antibody before flow cytometry. Results are expressed as values of relative avidity, that is the ratio of concentration of tested peptide necessary to reach 20% of the maximal binding by the reference to that of the reference peptide. Therefore, the lower the value, the stronger the binding. Following this method, a peptide is said to have a high relative affinity for a particular HLA class I molecule, when RA<1. In contrast, a medium relative affinity is concluded when RA is comprised between 1 and 5, and preferably between 1 and 3.

Among the hTERT nonamers and decamers, and particularly the above-identified peptides, the following MHC class I-restricted hTERT epitopes can be classified as having high relative affinity for MHC class I molecule: MPRAPRCRA (SEQ ID NO: 6) (p1), APRCRAVRSL (SEQ ID NO: 7) (p4) and APSFRQVSCL (SEQ ID NO: 8) (p68). Using the same approach, the following MHC class 1-restricted hTERT epitopes can be classified as having a medium relative affinity for MHC class I molecule: RPAEEATSL (SEQ ID NO: 9) (p277), RPSFLLSSL (SEQ ID NO: 10) (p342), DPRRL VQLL (SEQ ID NO: 12) (p444) and RPSLT-GARRL (SEQ ID NO: 11) (p351).

The present invention also relates to a polynucleotide encoding a MHC class 1-restricted epitope analogue, i.e., epitopes having at least one amino acid substitution compared to a class 1-restricted hTERT epitope as described above, especially HLA-B7-restricted epitope analogue.

The term "analogue" as defined herein relates to a peptide whose sequence is derived from a hTERT peptide as described above by at least one amino acid substitution, either conservative, semi-conservative or non-conservative. An analogue is opposed to an epitope by the fact that its nucleotide and/or amino acid sequence is not found in the reference hTERT gene or protein disclosed in FIG. 1 which are considered within the present application as the molecules of reference to define the so-called wild type peptides or polynucleotides. Such an analogue may result from the substitution in the corresponding nucleotide sequence of one or several nucleic base(s) in the codon encoding said amino acid. Therefore, a polynucleotide analogue differs from its wild type counterpart (polynucleotide encoding hTERT peptide with the reference sequence from which the peptide analogue is derived from) by at least one substitution, and preferably one, two or three substitutions in the codon(s) encoding the amino acid residue to be substituted. As an example, the APRRLVQLL (SEQ ID NO: 17) peptide (called p444*) is derived from the p444 peptide by the substitution of the first amino acid residue (D→A).

A particular analogue of a HLA-B7-restricted analogue has the same length or is shorter than the epitope from which it derives.

As a particular embodiment, the hTERT epitopes described above or the analogues always conserve in their primary structure a proline (P) in position 2, and/or one of the following amino acids in the last C-terminal position: A, L, I, M, V, F1 W or Y. Therefore, the hTERT peptides, including the analogues, have the following consensus sequence: X-P-X$_{6-7}$-[ALIMVFWY], wherein X refer to any amino acid, X$_{6-7}$ refers to the number of amino acids and [ALIMVFWY] refers to one of these amino acids.

Therefore, to provide an epitope analogue, the amino acid substitution or the corresponding codon substitution in the polynucleotide is not located in the second position (or second codon). In a preferred embodiment, no substitution is carried out in the C-terminal position, even though the last C-terminal amino acid can be replaced by an equivalent amino acid, i.e. either A, L, I, M, V, F, W or Y. Finally, in a preferred embodiment, the substitution is located in the first amino acid position, wherein any amino acid is replaced by an alanine (A).

In a further embodiment of the invention, the last C-terminal amino acid of a decamer is deleted to give a nonamer, provided that the resulting nonamer maintains or adopts the X-P-$X_{67}$-[ALIMVFWY] consensus sequence. In the same way, an amino acid selecting among A, L, I, M, V, F, W and Y is added at the C-terminal end of a nonamer to give rise to decamer, provided that the resulting decamer maintains or adopts the X-P-$X_{67}$-[ALIMVFWY] consensus sequence.

In case of substitution, deletion or addition, including especially those illustrated above, taken individually or as combinations, the tridimensional conformation of the peptide analogue must be the same or slightly modified with respect to the one of the wild type counterpart, to ensure a correct folding of the analogue and its correct binding to the MHC class I molecule. The MHC stabilization assay described above can be used to check that such constraints are fulfilled.

The resulting analogue has at least the same characteristics as its wild type counterpart, in terms of affinity for a particular MHC class I molecule, especially HLA-B7 molecule, and has essentially the same capacity to be transported as an epitope/MHC complex on the cell surface and/or has essentially the same capacity to elicit an immunogenic response when tested in the same conditions.

In a preferred embodiment, the starting peptide is a hTERT epitope having a medium affinity, and the resulting analogue has a higher affinity than its wild type counterpart. In another embodiment, the analogue has a higher immunogenicity than its wild type counterpart. As an example, the p444* peptide analogue quoted above has an increased affinity for MHC class I molecule compared to the p444 peptide from which it is derived from.

This is an object of the invention to provide hTERT epitope or analogue, able to elicit an immune response, and particularly a CTL response (Cytotoxic T Lymphocyte). However, the T lymphocytes do not recognize said analogue that is used to stimulate said lymphocytes only, via antigen presenting cells. In an embodiment of the invention, the analogue as described above keeps its immunogenic behaviour, and is able to elicit an immune response against cells overexpressing hTERT epitopes, i.e. that CTLs recognize the wild type epitope, even if stimulated with an epitope analogue. In a particular embodiment, the lymphocytes stimulated by an epitope analogue of the invention do not react against cells, which do not overexpressed hTERT epitopes. Therefore, stimulated lymphocytes do not react with cells overexpressing other epitopes (cross reaction) or with cells expressing hTERT epitope as basal level (healthy cells). In a particular embodiment, all the characteristics mentioned above are in a HLA-B7 environment, and preferably in a HLA-B0702 context.

A conventional cytotoxicity assay may be performed by using a standard 4-5 h $^{51}$Cr release assay to test the capacity of stimulated lymphocytes to react against target cells, such as in the Firat publication (1999. Eur. J. of Immunol. 29: 3112-3121) incorporated herein by reference. Briefly, cell suspension containing CTLs, are activated with peptide (hTERT peptide or analogue in the present case) plus self MHC Class I molecule in vivo. Target cells (expressing or not the corresponding HTERT epitope) previously incubated with $^{51}$Cr, are then incubated with activated lymphocytes. The recognition of target cells by activated CTL leads to the apoptosis of target cells and the release of $^{51}$Cr, wherein said release is proportional to the number of target cells killed. An incubation of target cells with a control peptide is used as a negative control to calculate the spontaneous release of $^{51}$Cr. Specific percentage of lysis is calculated by subtracting non-specific lysis observed with the control peptide to lysis obtained with the peptides to be tested. The higher the percentage, the more targets have been killed by the CTL. Specific lysis is determined at several ratios of Effector (CTL) to target cells (E:T). The specific lysis is calculated as the ratio between [experimental release−spontaneous release] and [total release−spontaneous release].

The present invention also concerns a polynucleotide encoding a polyepitope. A polyepitope is defined as a polypeptide having at least two epitopes, chosen among the MHC class 1-restricted, especially HLA-B7-restricted hTERT epitopes (p1, p4, p68, p277, p342, p351, p444, p464, p966, p1107 and p1123) and/or MHC class 1-restricted, especially HLA-B7-restricted, epitope analogues of the invention. The polynucleotide of the invention comprises or consists of at least two polynucleotide units encoding said epitopes or analogues. A polynucleotide unit is defined as the coding sequence for an epitope or analogue of the invention as disclosed herein.

The invention particularly concerns a polynucleotide encoding a polyepitope, comprising at least two epitopes chosen among (a) RPSLTGARRL (SEQ ID NO: 11) (p351), (b) APSFRQVSCL (SEQ ID NO: 8) (p68), (c) APRCRAVRSL (SEQ ID NO: 7) (p4), (d) DPRRLVQLL (SEQ ID NO: 12) (p444), (e) FVRACLRRL (SEQ ID NO: 13) (p464), (f) AGRNMRRKL (SEQ ID NO: 14) (p966), (g) LPGTTLTAL SEQ ID NO: 15) (p1107) and (h) LPSPKFTIL (SEQ ID NO: 16) (p1123), or their analogues as defined above. Another polynucleotide, encoding a polyepitope, comprises at least one polynucleotidic unit chosen in the group of either a polynucleotide encoding a HLA-B7-restricted hTERT epitope corresponding to (a) RPSLTGARRL (SEQ ID NO: 11) (p351), (b) APSFRQVSCL (SEQ ID NO: 8) (p68), (c) APRCRAVRSL (SEQ ID NO: 7) (p4), (d) DPRRLVQLL (SEQ ID NO: 12) (p444), (e) FVRACLRRL (SEQ ID NO: 13) (p464), (f) AGRNMRRKL (SEQ ID NO: 14) (p966), (g) LPGTTLTAL (SEQ ID NO: 15) (p1107) and (h) LPSPKFTIL (SEQ ID NO: 16) (p1123) and/or their analogues as defined above, and at least one polynucleotidic unit chosen in the group of the polynucleotides encoding the sequence MPRAPRCRA (SEQ ID NO: 6) (p1), RPAEEATSL (SEQ ID NO: 9) (p277) or RPSFLLSSL (SEQ 10 NO: 10) (p342), or their analogues as defined above.

None of the polyepitope-encoding polynucleotides of the invention coincides with the coding sequence of the full length hTERT.

In a particular embodiment of the invention, the number of MHC class I restricted hTERT epitopes and/or analogues in the prepared polyepitope is limited to 30. In another embodiment, the number of HLA-B7 restricted hTERT epitopes and/or analogues is limited to approximately 30, and is preferably 2, 3, 4, 5, 6, 7, 8, 9, 10, 15, 20, 25 or 30. In another embodiment, the number of HLA-B0702 restricted hTERT epitopes and/or analogues is limited to approximately 10, and is preferably 2, 3, 4, 5, 6, 7, 8, 9 or 10.

Accordingly, the polynucleotide encoding a polyepitope has 30 or less polynucleotide units, especially 2, 3, 4, 5, 6, 7, 8, 9, 10, 15, 20, 25 or 30 or any number within this range.

In a particular embodiment the polynucleotide units (and accordingly the epitopes) of the polynucleotide are consecutive.

In such a particular embodiment of the invention, the size of the nucleic sequence encoding the consecutive hTERT epitopes or analogues is less than 3000 bp, and preferably less than 2000 bp, 1000 bp, 500 bp, 400 bp, 300 bp, 200 bp or 100 bp.

In a particular embodiment, the polynucleotide encoding the multiple epitopes (polyepitope) consists of a nucleic acid molecule encoding a truncated or mutated form of the hTERT protein. In a preferred embodiment, the truncated or mutated form of the hTERT protein is deprived of its catalytic activity, i.e., is not capable to direct the synthesis of the repeat unit ($T_2AG_3$) at the ends of chromosomes, participating in the maintenance of telomere length. Such a hTERT protein deprived of its catalytic activity i.e., the retrotranscriptase activity, is said non-functional. Therefore, in another particular embodiment, the nucleic acid molecule encoding a truncated or mutated form of the hTERT protein lacks the catalytic activity domain of hTERT. In a particular embodiment, the nucleic acid molecule encoding a truncated form of the hTERT protein encodes a protein consisting of at least the 500 last C-terminal amino acids.

In a particular embodiment, the polynucleotide encodes a hTERT protein that is deleted for amino acids 867 to 869 (VDD sequence), corresponding to nucleotides 2654 to 2662 of FIG. 1 (wild-type) and providing nucleotide 2657 to be contiguous to nucleotide 2658 in FIG. 9 representing the deletion site, or alternatively for amino acids 864 to 872, corresponding to nucleotides 2645 to 2671 of FIG. 1 (wild-type) and providing nucleotide 2648 to be contiguous to nucleotide 2649 in FIG. 10 representing the deletion site. In a particular embodiment, the encoded hTERT protein has a deletion that comprises at least the amino acid residues 867 to 869 i.e., that the deletion is larger than the 3 amino acid residues (VDD sequence). As an example are the 864-872 deletion described above as well as a 22 amino acid deletion starting from amino acid residue 857 to 879 (according to FIG. 1) or a deletion comprising the 5 amino acids N-terminal and the 5 amino acids C-terminal to the VDD sequence (from amino acid 862 to amino acid 874 according to FIG. 1, corresponding to nucleotides 2639 to 2679). In a particular embodiment, the invention concerns a polynucleotide comprising or consisting of the nucleotide sequence as set forth in FIG. 9 or FIG. 10.

The polynucleotide units encoding the multiple epitopes of the invention can be arranged consecutively, i.e., the 3' end of the first polynucleotide unit is directly linked to the 5' end of the second polynucleotide unit (and so on), resulting in a polynucleotide encoding a peptidic sequence exclusively composed of consecutive epitopes. Such a polynucleotide can encode a polyepitope comprising or consisting of the p1, p4, p68, p277, p342, p351, p444, p464, p966, p1107 and p1123 peptides. In a particular embodiment, the polynucleotide encodes the following peptidic sequence MPRAPRCRAAPRCRAVRSLAPSFRQVSCLRPAEEAT-SLRPSFLLSSLRPSLTGARRL (SEQ ID NO: 20), comprising thus 6 MHC class I-restricted, particularly HLA-B7 restricted, hTERT epitopes.

The multiple epitopes of the invention can alternatively be separated by a one-amino acid spacer or a peptide spacer, i.e., meaning that the different polynucleotide units are separated by one or several codon(s) encoding respectively one or several amino acid(s). As spacers improving the processing of multiple epitopes, 4 amino acid-peptides composed of an arginine (R) in the C terminal position and hydrophilic residues (A, K, D and/or T) in other positions are preferred. Especially, 4 amino acid-peptides having a positively charged residue or an acidic residue in the C terminal position may be used, dependently or independently of hydrophilic residues (A, K, D and/or T) in other positions. In a particular embodiment, said spacers are internal processing sequences such as endosomal or lysosomal processing sequences, enabling the better processing of the multiple epitopes and avoiding the processing of new peptides resulting from overlapping cutting. Such a separation having recourse to a spacer can be used to separate all or, to the contrary, part of the polynucleotide units and accordingly, all or part of the epitopes.

The order in which the epitopes are arranged can be determined by the man skilled in the art, according to the following criteria: some orders may facilitate either the transcription and/or the translation of the polynucleotide, may facilitate the transport of the resulting expressed polyepitope in the endoplasmic reticulum (ER), especially if the tridimensional conformation impacts the properties, and may facilitate the processing of the polyepitope in several epitopes or analogues and avoid the processing of overlapping epitopes.

The polyepitope of the invention enables the elicitation of a CTL response against at least one, especially against several epitopes or analogues contained in the polyepitope, simultaneously, in a single animal or human.

In a particular embodiment, the polynucleotide encoding the polyepitope of the invention further comprises a polynucleotide encoding a target signal, operably linked to the polynucleotide unit encoding the most N-terminal epitope of the at least two epitopes. "Operably linked" as used herein means that the target signal (upstream sequence) is linked to the N-terminal epitope (downstream sequence) in a way enabling the targeted signal to be operational, i.e., enabling to target the polyepitope to the correct cellular compartment or domain. Therefore, the link between the two sequences allows each sequence to play its own function in different locations and/or different stages. In a particular embodiment, said target signal is an endoplasmic reticulum signal sequence, and allows the polyepitope to be directed to the ER, for proper processing and association with the MHC class I molecule.

In a further embodiment, a codon encoding a methionine residue is added upstream of the sequence encoding the most N-terminal epitope, to enable the correct translation of the polynucleotide, if the translational process requires an initiation codon. Such a codon is added, only when the most N-terminal epitope does not possess a methionine residue in its first position.

The present invention also relates to a polynucleotide, according to the definitions given above, comprising or consisting of at least two polynucleotide units selected from the group consisting of:

a. ATGCCGCGCGCTCCCCGCTGCCGAGCC (SEQ ID NO: 21) (n1), b. GCTCCCCGCTGCCGAGCCGTGCGCTCCCTG (SEQ ID NO: 22) (n4), c. GCCCCCTCCTTCCGCCAGGTGTCCTGCCTG (SEQ ID NO: 23) (n68), d. AGACCCGCCGAAGAAGCCACCTCTTTG (SEQ ID NO: 24) (n277), e. CGGCCCTCCTTCCTACTCAGCTCTCTG (SEQ ID NO: 25) (n342), f. AGGCCCAGCCTGACTGGCGCTCGGAGGCTC (SEQ ID NO: 26) (n351), g. GACCCCCGTCGCCTGGTGCAGCTGCTC (SEQ ID NO: 27) (n444),
h. TTCGTGCGGGCCTGCCTGCGCCGGCTG (SEQ ID NO: 28) (n464),
i. GCTGGGAGGAACATGCGTCGCAAACTC (SEQ ID NO: 29) (n966),
j. CTCCCGGGGACGACGCTGACTGCCCTG (SEQ ID NO: 30) (n1107),
k. CTGCCCTCAGACTTCAAGACCATCCTG (SEQ ID NO: 31) (n1123), and
l. GCCCCCCGTCGCCTGGTGCAGCTGCTC (SEQ ID NO: 32) (n444*).

The following polynucleotides make also part of the invention:
a polynucleotide, comprising at least one polynucleotidic unit selected from:
a. AGGCCCAGCCTGACTGGCGCTCGGAGGCTC (SEQ ID NO: 26) (n351),
b. GCCCCCTCCTTCCGCCAGGTGTCCTGCCTG (SEQ ID NO: 23) (n68),
c. GCTCCCCGCTGCCGAGCCGTGCGCTCCCTG (SEQ ID NO: 22) (n4),
d. GACCCCCGTCGCCTGGTGCAGCTGCTC (SEQ ID NO: 27) (n444),
e. TTCGTGCGGGCCTGCCTGCGCCGGCTG (SEQ ID NO: 28) (n464),
f. GCTGGGAGGAACATGCGTCGCAAACTC (SEQ ID NO: 29) (n966),
g. CTCCCGGGGACGACGCTGACTGCCCTG (SEQ ID NO: 30) (n1107),
h. CTGCCCTCAGACTTCAAGACCATCCTG (SEQ ID NO: 31) (n1123), and
i. GCCCCCCGTCGCCTGGTGCAGCTGCTC (SEQ ID NO: 32) (n444*), or their analogues as defined above, and at least one polynucleotidic unit selected from:
j. ATGCCGCGCGCTCCCCGCTGCCGAGCC (SEQ ID NO: 21) (n1),
k. AGACCCGCCGAAGAAGCCACCTCTTTG (SEQ ID NO: 24) (n277),
l. CGGCCCTCCTTCCTACTCAGCTCTCTG (SEQ ID NO: 25) (n342), or their analogues as defined above.

a polynucleotide, comprising at least one polynucleotidic unit selected from:
a. AGGCCCAGCCTGACTGGCGCTCGGAGGCTC (SEQ ID NO: 26) (n351)
b. GCCCCCTCCTTCCGCCAGGTGTCCTGCCTG (SEQ ID NO: 23) (n68),
c. GCTCCCCGCTGCCGAGCCGTGCGCTCCCTG (SEQ ID NO: 22) (n4),
d. GACCCCCGTCGCCTGGTGCAGCTGCTC (SEQ ID NO: 27) (n444),
e. TTCGTGCGGGCCTGCCTGCGCCGGCTG (SEQ ID NO: 28) (n464),
f. GCTGGGAGGAACATGCGTCGCAAACTC (SEQ ID NO: 29) (n966),
g. CTCCCGGGGACGACGCTGACTGCCCTG (SEQ ID NO: 30) (n1107),
h. CTGCCCTCAGACTTCAAGACCATCCTG (SEQ ID NO: 31) (n1123), and
i. GCCCCCCGTCGCCTGGTGCAGCTGCTC (SEQ ID NO: 32) (n444*), or their analogues as defined above.

Are also included in the present invention, polynucleotides or polynucleotide units encoding an epitope, analogue or polyepitope of the invention, taking into consideration the degeneracy of the genetic code. Therefore, each amino acid can be encoded by the codon from the hTERT nucleotide reference sequence, or by any codon encoding said amino acid.

The invention also relates to a polynucleotide comprising or consisting of any combination of at least two of these polynucleotide units or analogues thereof, selected from the above group, wherein said polynucleotide unit or analogue encodes a MHC class 1-restricted, especially a HLA-B7-restricted, hTERT epitope.

All features given above concerning epitopes, analogues, polyepitopes, combination thereof, spacers, target signal sequences . . . are applicable to any polypeptide of the invention as well as to the corresponding polynucleotide sequences.

A recombinant vector, comprising or consisting of a polynucleotide of the invention, as defined above, is also one object of the present invention. The recombinant vector can be a vector for eucaryotic or procaryotic expression, such as a plasmid, a phage for bacterium introduction, a YAC able to transform yeast, a viral vector and especially a retroviral vector, or any expression vector. An expression vector as defined herein is chosen to enable the production of an epitope or analogue or polyepitope as defined above, either in vitro or in vivo.

Therefore, besides the polynucleotide, the vector of the invention can further comprise transcription regulation regions (including promoter, enhancer, ribosome binding site (RBS), polyA signal), a termination signal, a prokaryotic or eukaryotic origin of replication and/or a selection gene. The features of the promoter can be easily determined by the man skilled in the art in view of the expression needed, i.e., constitutive, transitory or inducible, strong or weak, tissue-specific and/or developmental stage-specific promoter. Therefore, tissue-specific promoters can be chosen depending on the organ in which a composition containing this vector is administered, for example injected, and depending on the intensity of expression required. In a particular embodiment, the promoter is the CMV promoter (human cytomegalovirus). Said vector can also comprise sequence enabling conditional expression, such as sequences of the Cre/Lox system or analogue systems.

The expression vectors of the invention may be viral vectors, and particularly viral expression vector, such as retroviral-derived, especially lentiviral-derived vectors such as HIV-, FIV- or SIV-derived vectors. More particularly, the lentiviral-derived vector is a human lentiviral-derived vector such as an HIV expression vector, particularly HIV-1 or HIV-2-derived vector. A retroviral-derived vector comprises a retroviral vector genome, usually included in a DNA construct, such as a plasmid, and expressed in viral particles, wherein said retroviral vector genome comprises the elements necessary for the retrotranscription, particularly the LTRs possibly mutated including deleted in part, especially deleted in the U3 region. In no case, the retroviral-derived vector contains all the nucleotide sequences encoding the full-length retroviral proteins. Possibly, it contains part of one or several of said nucleotide sequences providing it does not encode said proteins or functional fragments thereof. Said DNA construct comprising said retroviral vector genome further comprises a DNA of interest recombined with the retroviral nucleotide sequences, said DNA of interest comprising or consisting of a polynucleotide of the invention.

In a preferred embodiment, the retroviral-derived vector genome comprises a DNA flap as described below and at least one polynucleotide of the invention. In a preferred embodiment, the retroviral-derived vector is a HIV expression vector comprising a DNA flap as described below and at least one polynucleotide of the invention. HIV vectors express therefore only the nucleic acid(s) of interest, including the polynucleotides of the invention, contained between the two HIV LTRs and can thus accommodate large sequences up to 5-6 kb. A particular embodiment of the invention is a HIV expression vector, and most particularly a HIV-1 or HIV-2 expression vector, wherein a HIV-1 LTR or respectively the HIV-2 LTR is deleted for the promoter and the enhancer of the U3 domain (ΔU3). This particular deletion has been previously shown to increase the expression of the nucleic acid(s) contained in the vector, and particularly when associated with a promoter. Another particular embodiment, the vector comprises a LTR deleted in the promoter and the enhancer of the U3 domain, a promoter such as a CMV or EF1α promoter and a polynucleotide of the invention.

In another embodiment, the polynucleotide of the invention introduced in the retroviral-derived vector is included in an expression cassette.

A DNA flap (or Triplex as disclosed in WO 99/55892, WO 01/27300 and WO 01/27304) is a nucleotide sequence of retroviral or retroviral-like origin comprising two essential regions, i.e., the cPPT (central polypurine tract) and the CTS (cis-acting termination region) regions, wherein the cPPT and CTS regions induce a three-stranded DNA structure. A DNA flap suitable for the invention may be obtained from a retrovirus or retrovirus-like organism such as retrotransposon, prepared synthetically (chemical synthesis) or by amplification of the DNA flap from any retrovirus nucleic acid such as Polymerase Chain Reaction (PCR). The retrovirus, from which the DNA flap may be obtained, is particularly a retrovirus or a lentivirus, especially a human retrovirus or lentivirus and is in particular a HIV retrovirus, the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. In a more preferred embodiment, the DNA flap is obtained from an HIV retrovirus, for example HIV-1 or HIV-2 virus or any different isolate of these two types. It is noteworthy that the DNA flap is used isolated from its natural (viral genome) nucleotide context i.e., isolated from the pol gene in which it is naturally contained in a retrovirus. Therefore, the DNA flap is used, in the present invention, deleted from the unnecessary 5' and 3' parts of the pol gene and is recombined with sequences of different origin.

The DNA flap acts as a cis-determinant of the vector nuclear import, and is of great interest for the recombination and the integration of nucleic acid(s) into both non-dividing and dividing cells. Expression retroviral-derived vector, especially HIV derived-vectors, including the DNA flap sequence (TRIP vectors) are able to transduce primary B and T cells, macrophages, dendritic cells, etc with a tenfold higher efficiency than other HIV vectors that lack the DNA flap. A transduction of 80-90% of cells can be routinely obtained.

In a preferred embodiment, a vector suitable for an in vivo expression and vaccine strategy is a retroviral and especially a lentiviral vector (see WO 99/55892, WO 01/27300 and WO 01/27304). Such vectors have been shown to be particularly efficient and secure, when their genome is modified (Firat et al. 2002, The Journal of Gene Medicine 4: 38-45). Indeed, these vectors have the ability to efficiently and stably transfer therapeutic or reporter genes, in a large variety of cells and tissues, such as hematopoietic stem cells, brain, liver and retina. Moreover, this high transduction efficiency is irrespective of the proliferative status of the target cells. In particular, these vectors have been shown to efficiently induce $CD8^+$ T cell responses both in vivo in mice and ex vivo in humans, due to their capacity to transduce antigen presenting cells such as dendritic cell (DC) with high efficiency, ex vivo as well as in vivo (Esslinger et al. Hum Gene Ther 2002; 13: 1091-100; Breckpot et al. J Gene Med 2003; 5:654-67; Esslinger et al. J Clin Invest 2003; 111: 1673-81).

Figure 7:
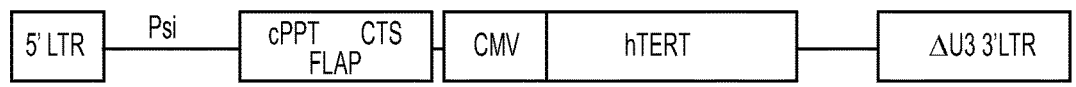

The vector, defined in FIG. 7, has been used for in vitro or in vivo expression of epitopes, analogues or polyepitopes of the invention. As examples of vectors, from which the vectors of the invention can be derived, are the following, all deposited with the CNCM (Collection Nationale de Culture de Microorganismes at Institut Pasteur, Paris, France):

| Vector name | Accession number | Date of deposition | Described in patent application |
| --- | --- | --- | --- |
| pTRIP.EGFP | I-2005 | Apr. 15, 1998 | WO 99/55892 |
| PTRIP-MEL.IRES-GFP | I-2185 | Apr. 20, 1999 | |
| PTRIP-TEL/AML-IRES-GFP | I-2326 | Oct. 11, 1999 | WO 01/27300 |
| PTRIP-TEL/ILKE-IRES-GFP | I-2327 | Oct. 11, 1999 | |
| PTRIP-DES-IRES-GFP | I-2331 | Oct. 11, 1999 | |

The vectors described in the patent application WO 01/27304, and especially TRIP ΔU3 Efα1 GFP and TRIP ΔU3 PL CMV GFP, can also be used to derive the vectors of the present invention.

A particular vector of the invention is the pTRIP-CMV-ΔhTERT vector, deposited at the CNCM (Institut Pasteur, Paris, France) under the number CNCM I-3660 on Jul. 28, 2006. A suitable growth medium for cultivating this vector is a TB medium, optionally supplemented with hygromycin. Another expression vector of the invention is the pTRIP-CMV-ΔhTERT vector deposited at the CNCM under the number CNCM I-3660 on Jul. 28, 2006, in which the deleted hTERT sequence has been substituted by any polynucleotide of the invention.

The present invention also relates to cells comprising the polynucleotides or polynucleotide units of the invention.

In one embodiment, the cell is transfected with a vector of the invention, by methods well known to the man skilled in the art, i.e. by chemical transfection (calcium phosphate, lipofectamine), lipid-based techniques (liposome), electroporation, photoporation, use of viral vectors . . . . In another embodiment, a cell is transformed or transduced with a polynucleotide of the invention, in a way enabling integration of the polynucleotide in the cell genome either by a recombination with the homologous cellular sequence or by insertion in the cellular genome. The transfection, infection or transduction can occur ex vivo, i.e. in an artificial environment outside the living organism.

Among cells particularly interesting in the vaccine strategy are cells of the immune system, and especially antigen presenting cells (APC). In a particular embodiment, these cells are APCs involved either in MHC class I recognition, like dendritic cells (DC) or in MHC class II recognition such as macrophages or lymphocytes B. Among DCs, ex vivo fully maturated DCs, i.e., DCs that have been in vitro maturated by epitopes or analogues, are preferred.

As used herein, the terms "transfected", "transformed" or "infected" refer to a cell comprising a vector of the invention (transient expression), whereas the term "genetically transformed" refers to a cell whose genome has been definitively modified by a polynucleotide of the invention (permanent expression).

Said transitory or stably transformed cells can be any prokaryotic (bacteria) or eukaryotic (yeast, animal including mammal especially human) cells. In an embodiment, cells are non-human cells. In a particular embodiment, cells of the invention are isolated human cells, "isolated" meaning outside of its natural environment.

A particular host is the *E. coli* strain deposited at the CNCM under the number CNCM 1-3660 on Jul. 28, 2006.

The invention also relates to epitopes, analogues or polyepitope as defined above when describing the polynucleotides of the invention and particularly to any polypeptide encoded by a polynucleotide or polynucleotide units of the invention. Particular polypeptides are MHC class 1-restricted, especially HLA-B7-restricted, hTERT epitope, chosen from the group consisting of:
 a. MPRAPRCRA (SEQ ID NO: 6) (p1),
 b. APRCRAVRSL (SEQ ID NO: 7) (p4),
 c. APSFRQVSCL (SEQ ID NO: 8) (p68),
 d. RPAEEATSL (SEQ ID NO: 9) (p277),
 e. RPSFLLSSL (SEQ ID NO: 10) (p342),
 f. RPSLTGARRL (SEQ ID NO: 11) (p351),
 g. DPRRLVQLL (SEQ ID NO: 12) (p444),
 h. FVRACLRRL (SEQ ID NO: 13) (p464),
 i. AGRNMRRKL (SEQ ID NO: 14) (p966),
 j. LPGTTLTAL (SEQ ID NO: 15) (p1107), and
 k. LPSPKFTIL (SEQ ID NO: 16) (p1123).

Particular HLA-B7-restricted hTERT epitopes, are chosen from the group consisting of:
 a. RPSLTGARRL (SEQ ID NO: 11) (p351),
 b. APSFRQVSCL (SEQ ID NO: 8) (p68),
 c. APRCRAVRSL (SEQ ID NO: 7) (p4),
 d. DPRRLVQLL (SEQ ID NO: 12) (p444),
 e. FVRACLRRL (SEQ ID NO: 13) (p464),
 f. AGRNMRRKL (SEQ ID NO: 14) (p966),
 g. LPGTTLTAL (SEQ ID NO: 15) (p1107),
 h. LPSPKFTIL (SEQ ID NO: 16) (p1123), and
 i. APRRLVQLL (SEQ ID NO: 17) (p444*).

A particular group consists of the following MHC class I-restricted, especially HLA-B7-restricted, hTERT epitopes:
 a. MPRAPRCRA (SEQ ID NO: 6) (p1),
 b. APRCRAVRSL (SEQ ID NO: 7) (p4),
 c. APSFRQVSCL (SEQ ID NO: 8) (p68), and
 d. RPSLTGARRL (SEQ ID NO: 11) (p351).

Another group consists of the following HLA-B7-restricted hTERT epitopes: RPAEEATSL (SEQ ID NO: 9) (p277) and RPSFLLSSL (SEQ ID NO: 10) (p342). A preferred HLA-B7 allele targeted by these epitopes is HLA-B0702.

The invention also concerns analogues of the peptides disclosed above, and having at least one amino acid substitution. Features pertaining to these analogues have especially been described in the above pages. A particular peptide analogue is p444* having the following peptide sequence APRRLVQLL (SEQ ID NO: 17).

Finally, the invention also concerns any polynucleotide encoding a hTERT epitope, analogue or polyepitope as described in the present specification.

The invention also relates to a polyepitope comprising at least two epitopes and/or analogues as described above. The polyepitopes of the invention are not the full-length hTERT protein. The size of said polyepitope can range from 15 to 1000 in particular from 50 or from 100 to 1000 amino acids, especially and particularly about 100, 200, 300, 400, 500 or 1000 amino acids. Such an epitope comprises or consists of 2 to 30 epitopes or analogues, and particularly 2 to 20 or 2 to 10 epitopes and/or analogues. A particular polyepitope comprises or consists of 6 consecutive epitopes and has the following sequence: MPRAPRCRAAPRCRAVRSLAPS-FRQVSCLRPAEEATSLRPSFLLSSLRPSLTGARRL (SEQ ID NO: 20). Another particular polyepitope comprises or consists of the p1, p4, p68, p277, p342 and p351 epitopes, the epitopes being either consecutive to each other in the polyepitope obtained or all or part of them being separated by peptide spacers.

Another polyepitope of the invention comprises at least two epitopes, at least one being chosen from the group consisting of:
 a. RPSLTGARRL (SEQ ID NO: 11) (p351),
 b. APSFRQVSCL (SEQ ID NO: 8) (p68),
 c. APRCRAVRSL (SEQ ID NO: 7) (p4),
 d. DPRRLVQLL (SEQ ID NO: 12) (p444),
 e. FVRACLRRL (SEQ ID NO: 13) (p464),
 f. AGRNMRRKL (SEQ ID NO: 14) (p966),
 g. LPGTTL TAL (SEQ ID NO: 15) (p1107),
 h. LPSPKFTIL (SEQ ID NO: 16) (p1123), and
 i. APRRLVQLL (SEQ ID NO: 17) (p444*),
or analogues thereof obtained by substitution of at least one amino acid residue, and at least one being chosen from the group consisting of
 j. MPRAPRCRA (SEQ ID NO: 6) (p1),
 k. RPAEEATSL (SEQ ID NO: 9) (p277),
 l. RPSFLLSSL (SEQ ID NO: 10) (p342),
or analogues thereof obtained by substitution of at least one amino acid residue, wherein said polyepitope is not the full length hTERT.

Polypeptides of the invention can be synthesized chemically, or produced either in vitro (cell free system) or in vivo after expression of the corresponding nucleic acid sequence in a cell system.

The full-length hTERT protein (SEQ ID NO: 37) as represented in FIG. 1 is excluded from the invention, as well as the corresponding full-length coding sequence (SEQ ID NO: 36). Also excluded from the present invention, the RPALL TSRL (SEQ ID NO: 42) peptide. These peptides are excluded particularly in the context of HLA-87 recognition.

The invention also concerns an epitope, analogue, polyepitope or polynucleotide, an expression vector or host cell as defined above, for use to elicit or participate in providing a HLA-B7-restricted immune response against hTERT.

The invention also concerns a composition comprising a polynucleotide, a vector, a host cell and/or a polypeptide of the invention. In a particular embodiment, said composition is suitable for in vivo administration, i.e., said composition is prepared for injection, or more generally for association with physiologically-acceptable liquid solutions or emulsions for administration. Said composition may be used either for systemic or local administration, especially by injection, and may further comprises a pharmaceutically suitable excipient (including water, saline, dextrose, glycerol, ethanol, and combinations thereof) or a carrier and/or a vehicle.

In a particular embodiment, said composition comprises a polynucleotide of the invention encoding an epitope, analogue or encoding a polyepitope as described above. Said composition can comprise other nucleic acid molecules encoding at least one hTERT epitope or analogue thereof or polyepitope, restricted to a different MHC class I allele from that of HLA-B7. The combination of hTERT epitopes restricted to different HLA supertypes or alleles enables covering a larger population of patients in need of treatment than a sole supertype or allele. To this end, HLA-A1, -A2, -A3 and -A24 are preferred.

In another embodiment, the composition comprises nucleic acid molecules encoding at least one hTERT epitope or analogue thereof or polyepitope, restricted to MHC class II. Said composition can comprise any combination of nucleic acid molecules as described above, with at least one HLA-B7-restricted hTERT epitope, analogue or polyepitope of the present invention. The combination, in a composition of nucleic acid molecules, of polynucleotides encoding Class I and Class II-restricted epitopes enabling the reaction of various immune cells (T lymphocytes or NK cells for class I versus helper lymphocytes for class II) and/or the elicitation of various immune responses (humoral versus cellular response) is also within the present invention.

In another embodiment, the composition comprises nucleic acid molecules comprising at least such molecules encoding one tumour-specific antigen (TSA) and/or at least one tumour-associated antigen (TAA), such as prostate specific antigen (PSA), prostate-specific membrane antigen (PSMA) or prostatic acid phosphatase (PAP) (Tartour et al. 2000 Immunol Lett September 15; 74(1): 1-3; Tartour et al. 1996 Presse Med. November 16; 25(25): 1717-22).

Several types of therapeutic compositions can be used to elicit an immune response against an epitope or analogue of the invention.

A composition comprising a polynucleotide of the invention is administered to a host, for instance injected (known as DNA vaccination) and said nucleic acid expresses in vivo a polypeptide comprising or consisting of multiple epitopes according to the invention. Such DNA vaccines usually consist of plasmid vectors as described above. The delivery of naked DNA has shown to be poorly efficient, and some carriers are needed to improve the delivery and uptake of DNA into cells. Two types of carriers have been yet developed: (1) viral carriers (adenoviruses, lentiviruses, measles virus), or (2) non-viral carriers such as polymers (and especially cationic polymers), encapsulated-DNA (liposomes, comprising cationic lipids interact spontaneously and rapidly with polyanions, such as DNA and RNA, resulting in liposome/nucleic acid complexes) or DNA linked to gold microparticles. Moreover, agents, which assist in the cellular uptake of nucleic acid, such as calcium ions, bacterial proteins (*Shigella* proteins) viral proteins and other transfection facilitating agents, may advantageously be used. Another type of composition according to the invention is a composition comprising lentiviral pseudoparticles comprising a vector or vector genome as mentioned above.

Another type of composition comprises an epitope, analogue or polyepitope of the invention. Such a composition is immunogenic, i.e., it is capable of eliciting an immune response in a host in which it is administered. However, to increase the immunogenic properties of the polypeptides of the invention, an adjuvant can be administered with the polypeptide, to elicit or improve the immune response. An adjuvant is defined as any substance that enhances the immunogenicity of an antigen mixed with said adjuvant. Some adjuvants convert soluble antigens into small particles, such as aluminium hydroxide gel, oil in water emulsion or immune stimulatory complexes (ISCOMs). Another class of adjuvants comprises sterile constituents of bacteria such as cell wall or polysaccharides, Freund adjuvant. Finally, emulsifying agents or pH buffering agents can also be used to enhance the immunogenic behaviour of the epitope or analogue.

All compositions quoted above can be injected in a host via different routes: subcutaneous (s.c), intradermal (i.d.), intramuscular (i.m.) or intravenous (i.v.) injection, oral administration and mucosal administration, especially intranasal administration or inhalation. The quantity to be administered (dosage) depends on the subject to be treated, including the condition of the patient, the state of the individual's immune system, the route of administration and the size of the host. Suitable dosages range from 200 µg to 1 mg, and can be modified by one skilled in the art, depending on circumstances.

The compositions of the invention are useful for the prophylaxis and or treatment of malignant states in patients, resulting from uncontrolled cell proliferation, including tumors, resulting from the over-expression of hTERT, as well for the treatment of detrimental consequences accompanying such malignant state, e.g., cancer. The expression "treatment" encompasses the curative effect achieved with compositions of the invention and also the beneficial effect for the patient undergoing the treatment, said effect being either obtained at cellular level or clinical level, including as a result, an improvement of the condition of the patient and/or a remission state or a recovery of a health state. In a particular embodiment, the composition of the invention further comprises additional active compounds useful for the prophylaxis or the treatment of tumors, either general compounds or compounds proved to be active in a tissue-specific cancer.

The invention also concerns a process to activate T lymphocytes against class I-restricted, particularly HLA-B7-restricted, hTERT epitopes:
a. providing T lymphocytes, and
b. in vitro cultivating said T lymphocytes with at least one epitope or epitope analogue or polyepitope of the invention, in conditions enabling the activation of said lymphocytes.

In a particular embodiment, activated T lymphocytes are cytotoxic T lymphocytes (CTL). Conventional conditions to activate T lymphocytes use interleukine (IL) 2, IL-7, IL-12 and/or IL-15, and are described in Minev et al. (2000 PNAS; 97(9): 4796-4801) incorporated herein by reference.

The invention also relates to a process to check the immunogenic behaviour of a hTERT peptide, comprising:
a. activating T lymphocytes, by in vitro cultivating said T lymphocytes with at least one epitope or epitope analogue or polyepitope of the invention, in appropriate conditions,
b. in vitro cultivating said activated lymphocytes with target cells expressing, at their cell surface, a hTERT epitope of the invention bound to a MHC-class I molecule, in suitable conditions, and
c. determining whether said activated lymphocytes react against said target cells.

In a particular process to check the immunogenic behaviour of a hTERT peptide, the epitope when used individually i.e., not under the form of a polyepitope, is chosen among (a) RPSLTGARRL (SEQ ID NO: 11) (p351), (b) APSFRQVSCL SEQ ID NO: 8) (p68), (c) APRCRAVRSL (SEQ ID NO: 7) (p4), (d) DPRRLVQLL (SEQ ID NO: 12) (p444), (e) FVRACLRRL (SEQ ID NO: 13) (p464), (f) AGRNMRRKL (SEQ ID NO: 14) (p966), (g) LPGTTL TAL (SEQ ID NO: 15) (p1107) and (h) LPSPKFTIL SEQ ID NO: 16) (p1123); an example of analogue is the p444* as defined above.

A process to check the immunogenic behaviour and HLA-87-restriction of a hTERT peptide, comprising a. activating T lymphocytes as described above, with an epitope chosen among MPRAPRCRA (SEQ ID NO: 6) (p1), APRCRAVRSL (SEQ ID NO: 7) (p4), APSFRQVSCL (SEQ ID NO: 8) (p68), RPAEEATSL (SEQ ID NO: 9) (p277), RPSFLLSSL (SEQ ID NO: 10) (p342) RPSLTGARRL (SEQ ID NO: 11) (p351), DPRRLVQLL (SEQ ID NO: 12) (p444), FVRACLRRL (SEQ ID NO: 13) (p464), AGRNMRRKL (SEQ ID NO: 14) (p966), LPGTTLTAL (SEQ ID NO: 15) (p1107) and LPSPKFTIL (SEQ ID NO: 16) (p1123) or epitope analogue such as APRRLVQLL (SEQ ID NO: 17) (p444*) or polyepitope as defined above;

b. in vitro cultivating said activated lymphocytes with target cells expressing, at their cell surface, a hTERT epitope of the invention bound to a HLA-87 molecule, in suitable conditions, and c. determining whether said activated lymphocytes react against said target cells.

The activation of lymphocytes includes the presentation of said epitopes or analogues by antigen presenting cells to naive (not activated) T lymphocytes. Once naive T lymphocytes have recognized the epitope or analogue of the invention, in the context of a particular class-I HLA molecule, they are said "activated" and ready to recognize said epitope on the cell surface of a target cell. The contact between said activated lymphocytes (effector cells) and target cells (expressing the epitope, from which the lymphocyte has been activated), leads to the secretion of molecules and killing of the target cells. If an epitope or analogue used to activate lymphocytes leads to an efficient destruction of a target cell bearing said epitope by said activated lymphocytes, said epitope can be considered as immunogenic enough to allow not only in vitro but also in vivo T cell reaction against cells expressing said epitopes. Suitable conditions for target cells/lymphocytes recognition are a 4 hour-contact at 37° C. in RPMI medium.

The invention also relates to a process to in vitro maturate cells, and especially antigen presenting cells (APC), B cells, T cells and/or dendritic cells, against MHC class I-restricted, particularly HLA-B7-restricted, hTERT epitopes. Such a process to in vitro maturate cells comprises:

a. providing cells, b. enabling the maturation of said cells with at least one MHC class 1-restricted, particularly HLA-B7-restricted, hTERT epitope or epitope analogue or polyepitope of the invention, and c. optionally, favouring the expansion of said maturated cells.

As described above, the activation of lymphocytes requires epitope presentation by maturated antigen presenting cells. In a preferred embodiment of the invention, said cells express at least one HLA-B7 allele. One of them, dendritic cells (DC), are particularly efficient in presentation of endogenous epitopes restricted to MHC class I, to T lymphocytes. One of the objectives in the maturation of said cells is their administration once maturated, to a patient in need of treatment. The administration of said maturated DCs would result in vivo in the activation of patient's lymphocytes, and rapid reaction against cell expressing the epitope (the one, the DCs have been transformed with).

In a particular embodiment, a process to in vitro maturate dendritic cells comprises:

a. providing dendritic cells, b. enabling the maturation of said dendritic cells with at least one MHC class 1-restricted hTERT epitope or epitope analogue or polyepitope of the invention, and c. optionally, favouring the expansion of said maturated dendritic cells.

In a particular embodiment, said dendritic cells are isolated from either circulating blood or bone marrow cells. In another embodiment, dendritic cells are isolated from the patient in need of treatment or from an HLA-matched donor, to avoid rejection after the administration to said patient.

The maturation of DCs can be achieved by genetic transformation of said dendritic cells with a polynucleotide of the invention, by transfection of said dendritic cells with a vector of the invention or by contacting said dendritic cells with at least one epitope, epitope analogue or polyepitope of the invention. The genetic transformation is preferred because of its efficiency and the permanent expression of the epitope, analogue or polyepitope encoded by the polynucleotide inserted in the DC genome The invention also concerns a polynucleotide encoding a HLA-87-restricted hTERT epitope for use in the prevention and/or treatment of cancer. In a particular embodiment, said polynucleotide, for use in the prevention and/or treatment of cancer encodes a HLA-87-restricted hTERT epitope or analogue thereof or a polyepitope comprising at least one HLA-87-restricted hTERT epitope or analogue thereof as described in the present application. As far as the polyepitope-encoding polynucleotide is concerned, it does not coincide with the coding sequence of the full-length hTERT. On the other hand, it can coincide with a mutated or deleted version of HTERT, said mutation or deletion suppressing the catalytic activity of the human telomerase. In a particular embodiment, said polynucleotide comprises at least one polynucleotide unit encoding a HLA-87-restricted hTERT epitope, chosen from the group consisting of:

a. MPRAPRCRA (SEQ ID NO: 6) (p1),
   b. APRCRAVRSL (SEQ ID NO: 7) (p4),
   c. APSFRQVSCL (SEQ ID NO: 8) (p68),
   d. RPAEEATSL (SEQ ID NO: 9) (p277),
   e. RPSFLLSSL (SEQ ID NO: 10) (p342),
   f. RPSLTGARRL (SEQ ID NO: 11) (p351)
   g. DPRRLVQLL (SEQ ID NO: 12) (p444),
   h. FVRACLRRL (SEQ ID NO: 13) (p464),
   i. AGRNMRRKL (SEQ ID NO: 14) (p966),
   j. LPGTTLTAL (SEQ ID NO: 15) (p1107), and
   k. LPSPKFTIL (SEQ ID NO: 16) (p1123).

or at least one analogue of said HLA-B7-restricted hTERT, such as APRRLVQLL (SEQ ID NO: 17) (p444*), or any combination forming a polynucleotide having at least two polynucleotide units encoding said HLA-B7 epitopes and/or analogues.

The invention concerns a HLA-B7 hTERT epitope, and especially a HLA-B0702 restricted epitope for use in the prevention and/or treatment of cancer. The invention relates also to a polynucleotide, a vector, a host cell or a polypeptide of the invention for use in the prevention and/or treatment of cancer.

The invention also relates to the use of a HLA-B7 hTERT epitope, (or corresponding polynucleotide) for the manufacture of a drug for the prevention and/or treatment of cancer. Particular HLA-B7 hTERT epitopes (or corresponding polynucleotides) are those described above as well as vectors, cells or compositions comprising or consisting of them. In a particular embodiment, the use of polynucleotide, vector, host cell or polypeptide comprising or consisting of a polyepitope of the invention in the manufacture of a drug for the prevention and/or treatment of cancer is intended for patients having at least one HLA-B7 allele as defined above, and particularly at least one HLA-B0702 allele.

Each definition provided in the specification applies to each and any peptide (epitope, analogue or polyepitope) as well as to each and any polynucleotide, taken individually (as such) or encompassed in a group.

FIGS. 1A to 1F: Gene encoding the hTERT protein (SEQ ID NO: 36) and corresponding amino acid sequence (SEQ ID NO: 37). The coding sequence is located between the nucleotide 56 and 3454. Initiation and termination codons are underlined. First line is the nucleotide sequence; second line is the corresponding amino acid sequence. Third line is the numerotation of the hTERT coding sequence, starting from the initiation codon as the first amino acid.

FIG. 2: hTERT derived peptides are processed in HLA-B0702 transgenic mice. HLA-B7 Tg mice and one naïve mice (N) were immunized with 100 µg DNA encoding Htert. On day 14, spleen cells from each mouse were separately in vitro stimulated with different hTERT-derived peptides. Effector cells were essayed 6 days later against RMA-B7 targets loaded with relevant (shaded) or control (unshaded) peptides as described in the material and methods. Percentage of lysis at a 60/1 ratio are shown (results from two independent experiments).

Figure 3:
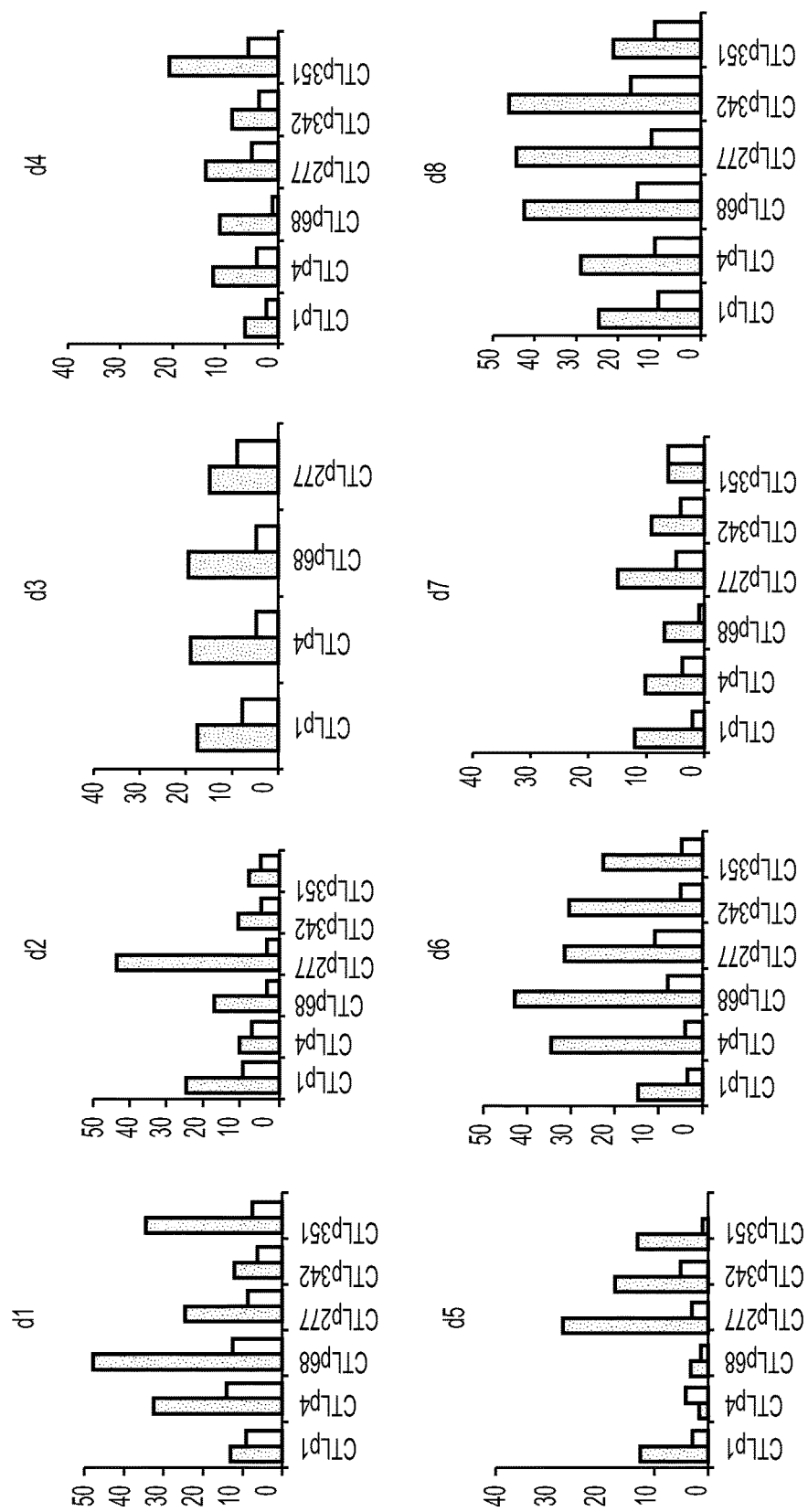

FIG. 3: Induction of CTL response against hTERT in PBMC from health blood donors. T-lymphocyte cells from HLA-*B0702+ healthy donors were activated with each of the six hTERT peptide-pulsed autologous PBMC as detailed in materials and Method. After four rounds of weekly stimulation, effector cells, pulsed with relevant (shaded) or control (unshaded) peptides, were essayed for lytic activity against $^{51}$Cr-labeled T2-B7 cells. Percentage of lysis at a 20/1 effector-target ratio is shown. Results from δ out of 10 donors are presented (d1 to d8).

FIG. 4: Effect of an anti-HLA class I mAb on cytotoxicity of CTLp351 against tumor cells. The cytotoxicity of the CTLp351 line against HLA-*B0702+ tumor cell lines Mamo and U293T pre-treated either in absence (none) or presence of HLA mAbs (anti-HLA class I mAb or an anti-class II mAb (HLA-DR)) was determined by standard $^{51}$Cr-release assay at effector-target ratio of 10/1.

Figure 5A:
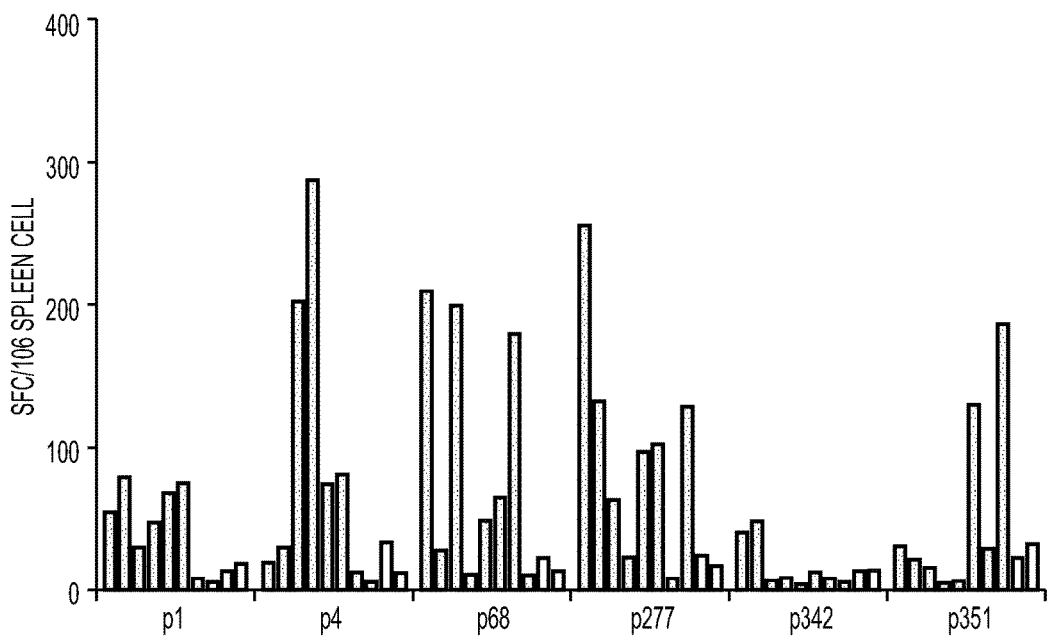
Figure 5B:
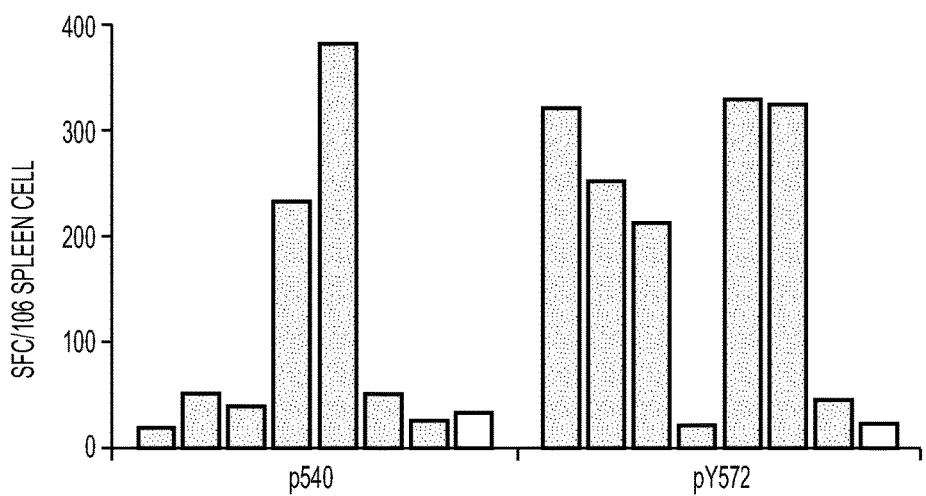

FIG. 5: Ex-vivo detection of hTERT-specific T-cell response after Lv-hTERT immunization. A) HLA-B7 transgenic mice were immunized with recombinant Trip-hTERT particles or control Trip-GFP (1500 ng). After 12 days, hTERT peptide-specific T cells producing IFNγ of each mouse were detected ex vivo by IFNγ-ELISPOT assay within freshly spleen cells. The number of IFNγ SFCs was calculated after subtracting negative control values. Results from three independent experiments are represented.

B) HHD mice were immunized with Trip-hTERT as described above. hTERT peptide-specific T cells producing IFNγ were detected ex vivo by ELISPOT as described above. Results from two independent experiments are represented.

Figure 6:
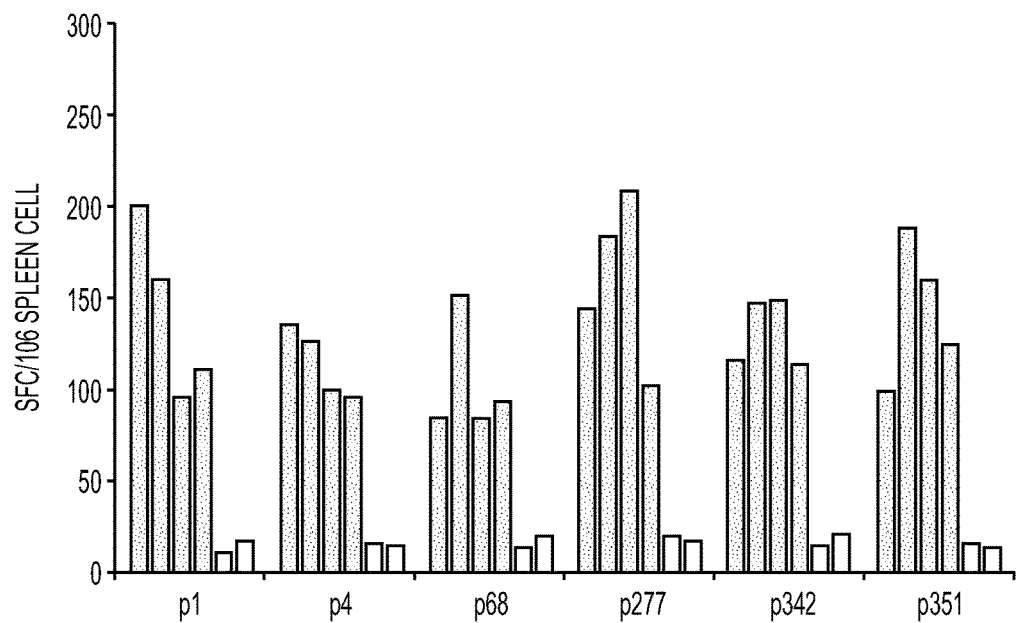

FIG. 6: Priming of specific CD8+ T cells responses in HLA-B*0702 transgenic mice following Trip-hTERT immunization. HLA-B*0702 transgenic mice were immunized either with Trip-hTERT (4 first shaded bars) or control (2 last unshaded bars). 12 days later, IFN-γ producing-single cells within splenocytes of each mouse were detected ex vivo by IFN-γ ELISPOT assay. Ficoll purified lymphocytes from freshly isolated splenocytes of individual immunized mice were directly cultured with or without 5 µg/ml of each HLA-B*0702-restricted hTERT-derived peptides for 24 h. The number of specific-IFN-γ SFCs was calculated after subtracting non-specific values obtained with control without peptide (<15 SFC), and the responses were considered positive for SFC>30.

FIG. 7: Schematic representation of the pTRIP-hTERT. This lentiviral-derived vector contains the psi sequence, the cPPT and CTS central cis-active sequences (Flap) of the HIV-1 genome and the CMV promoter which allows the expression of the gene of interest. Moreover, the U3 domain is deleted in the 3'LTR (ΔU3).

Figures 8A, 8B:
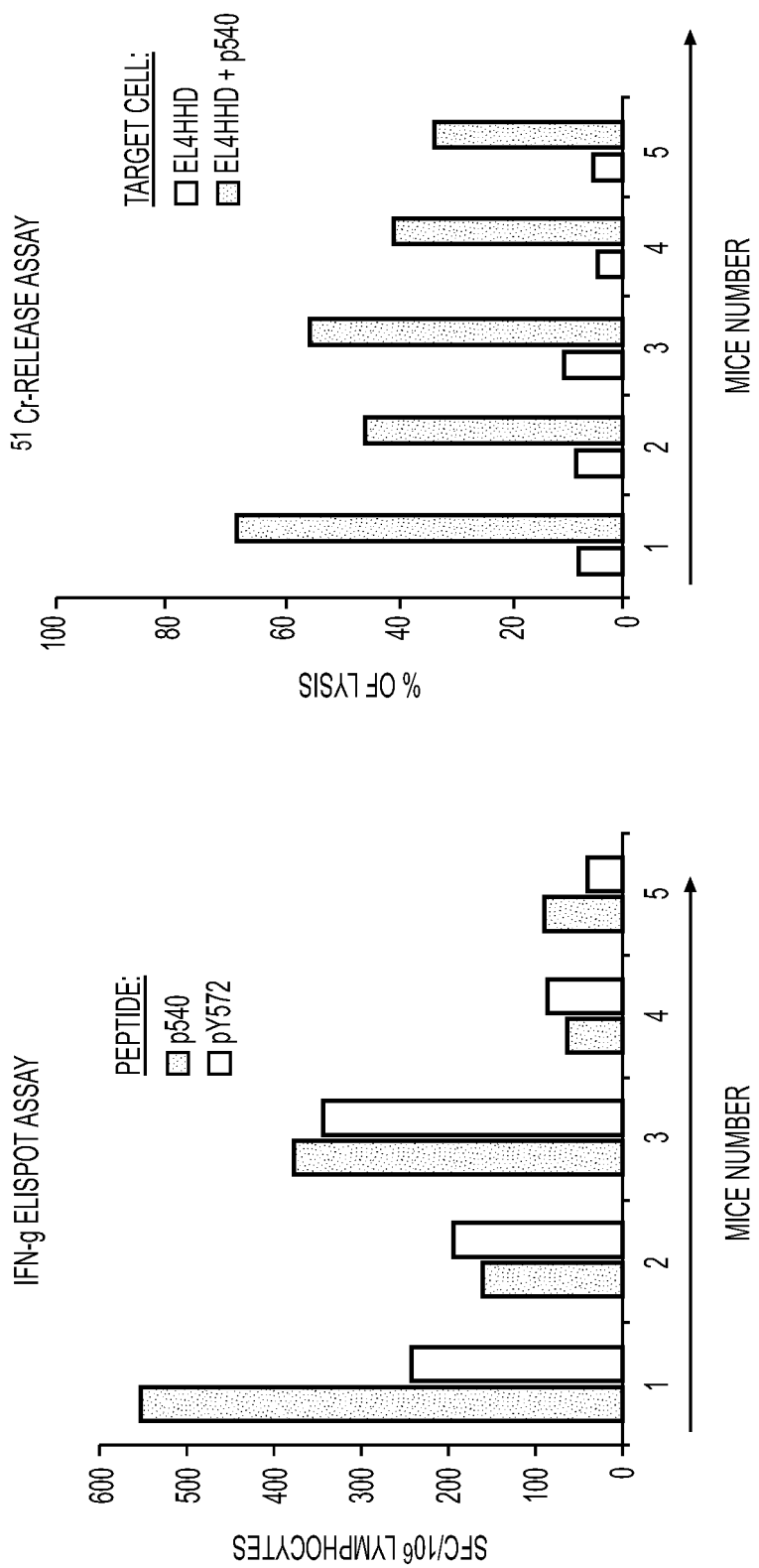

FIG. 8: A) DNA pTRIP-CMV-ΔhTERT immunization primed hTERT-specific CD8+ T cells responses in HHD mice. HHD mice (HLA-A2.1 Tg) were DNA immunized with a DNA encoding a non-functional form of HTERT (pTRIP-CMV-ΔhTERT). Ten days later, IFN-γ producing peptide-specific T cells were detected ex vivo by IFN-γ-ELISPOT assay. Ficoll purified lymphocytes from splenocytes of individual immunized mouse were directly cultured for 24 h, with or without 5 µg/ml of each H LA-A2.1-restricted hTERT-derived peptide. The number of specific-IFN-γ SFCs was calculated as described above. Responses were considered positive for SFC>30.

B) Induction of short CTL responses in HHD mice after pTRIP-CMV-ΔhTERT immunization. HHD mice were immunized with a DNA encoding a non-functional form of HTERT (pTRIP-CMV-ΔhTERT) for 10 days. Spleen cells from individual mice were restimulated in vitro with HLA-A2.1-restricted hTERT-derived p540 and pY572 peptides for 6 days. Effector cells were tested in a $^{51}$Cr-release assay against HHD-transfected EL4 cells loaded with either the relevant peptide or the irrelevant peptide.

FIGS. 9A to 9F: Sequence of a non-functional hTERT protein (deletion of amino acids 867 to 869). DNA sequence disclosed as SEQ ID NO: 38 and amino acid sequence disclosed as SEQ ID NO: 39. The coding sequence is located between the nucleotide 59 and 3348. Initiation and termination codons are underlined. First line is the nucleotide sequence; second line is the corresponding amino acid sequence. Third line is the numerotation of the hTERT coding sequence, starting from the initiation codon as the first amino acid.

FIGS. 10A to 10F: Sequence of a non-functional hTERT protein (deletion of amino acids 864 to 872). DNA sequence disclosed as SEQ ID NO: 40 and amino acid sequence disclosed as SEQ ID NO: 41. The coding sequence is located between the nucleotide 59 and 3430. Initiation and termination codons are underlined. First line is the nucleotide sequence; second line is the corresponding amino acid sequence. Third line is the numerotation of the hTERT coding sequence, starting from the initiation codon as the first amino acid.

EXAMPLES

Examples

I—Materials and Methods

Blood Donors

Peripheral bloods samples were obtained following written informed consent from adult healthy platelet donors (centre de transfusion sanguine de l'hôpital Mondor, Creteil, France). HLA typing of peripheral blood donors was performed in the HLA laboratory of the H. Mondor. Hospital Creteil (France). The study was approved by the French Blood Bank Institute.

Mice

HLA-*B0702 transgenic (Tg) mice, expressing an HLA-B0702 α1α2, H2-μd α3 chimeric construct, in combination with constitutive murine β2-m molecule (HLA-B7$^{mα3}$) and HHD transgenic mice expressing a chimeric HLA-A2.1/H2-Db molecule, were deleted of their H2-Db and H2-k$^b$ genes as previously described (Pascolo et al. J Exp Med 1997; 185:2043-51; Rohrlich et al. Int Immunol 2003; 15:765-72). These mice are on a C57BL/6 background and were bred and maintained under specific pathogen-free conditions in our animal facility.

Tumor Cells Lines

The T-B hybrid T1, EBV-transformed B cell JY, renal cancer cell line U293T and Burkitt lymphoma cell Raji were from American type Culture Collection (ATCC). Melanoma cell lines (SK23MEL, LB34, and KUL68) were kindly provided by P. Coulie (Bruxell, Belgium) and EBV-transformed B cell BBG.1 and BC3 were kindly provided by H. Collandre (R.A.H.P., Grenoble, France).

HLA-*B0702 transfected TAP deficient T2 cells (T2-B7) were kindly provided by P. Cresswell (Smith et al. J Immunol 1996; 156:3755-64). Murine lymphoma cell lines RMA, and EL4 were from ATCC; theses cells were also transfected with HLA-*B0702 gene and used as target cells.

Epitope Selection Peptide Synthesis

We used predictive algorithm "SYFPEITHI" (Lu and Celis E Cancer Res 2000; 60:5223-7) to analyse amino acid sequence of hTERT for the existence of 9-amino acid (nonamer) or 10-amino acid (decamer) peptides, predicted to bind to HLA-*80702. We selected candidate peptides that contain canonical HLA-B7-binding anchors, Pro at position 2 and hydrophobic aliphatic (Ala or Leu) at carboxyltermini, and according to their highest predictive score. Six peptides were retained and synthesized, three 9-amino acid peptides named p1, (MPRAPRCRA (SEQ ID NO: 6), residues 1-9), p277 (RPAEEATSL (SEQ ID NO: 9), residues 277-285) and p342 (RPSFLLSSL (SEQ ID NO: 10), residues 342-350), and three 10-amino acid peptides, p4 (APRCRAVRSL (SEQ ID NO: 7), residues 4-13) p68, (APSFRQVSCL (SEQ ID NO: 8, residues 68-77), and p351 (RPSLTGARRL (SEQ ID NO: 11), residues 351-360) (anchor positions are underlined).

Peptides derived from human cytomegalovirus pp65, RPHERNGFYV (SEQ ID NO: 33) (R1OTV), and human immunodeficiency virus type 1 IPRRIRQGL (SEQ ID NO: 34) were synthesized and were used as control peptides. Peptide derived from hepatitis B virus core 128-140 (TPPATRPPNAPIL (SEQ ID NO: 35)) was used as helper peptide for peptide immunization in mice. Peptides were purchased from PRIM to a minimum purity 80% and were reconstituted in distilled water or DMSO at a concentration of 2 mg/ml.

HLA-B0702 Binding/Stabilization Assay

The relative avidity of hTERT derived peptides for HLA-*B0702 was measured by using a MHC stabilization assay on HLAB0702 transfected T2 (T2-B7) cells in comparison with a reference peptide (R10TV) as described (Rohrlich et al. Int Immunol 2003; 15:765-72). Briefly, T2-B7 were incubated overnight at $2×10^5$ cells/well in 96-well plates in serum free medium AIM-V (Invitrogen Corp., Gibco), supplemented with 100 ng/ml of human β2-microglobulin, in the absence (negative control) or in the presence of either reference peptide R10V or hTERT peptides at various final concentrations (100, 10, 1 and 0.1 μM). T2-B7 cells were labelled with a saturating concentration of ME.1 an anti-HLA-B7 mAb, then washed twice and finally stained with FITC-conjugated F(ab')2 goat anti-mouse Ig before flow cytometry.

Results are expressed as values of relative avidity, that is the ratio of concentration of test peptide necessary to reach 20% of the maximal binding (obtained with the reference peptide) over the concentration of the reference peptide. Therefore, the lower the value, the stronger the binding.

Peptide Immunization of HLA-*B0702 Transgenic Mice for CTL Induction

Female HLA-*B0702 transgenic mice at 8-10 weeks of age were injected subcutaneously (s.c.) at the base of the tail with 50 μg of individual HLA-B0702 restricted hTERT peptides supplemented with 140 μg of helper peptide co-emulsified in incomplete Freund's adjuvant (Difco, Detroit, Mich.). Ten days later, spleen cells of individual mouse were reactivated in vitro with relevant peptide in six wells plate. Effector CTL cells were tested in a standard 4-5 h $^{51}$Cr-release assay, using relevant or negative control peptide-pulsed, HLA-*B0702 transfected RMA cells (RMA-B7). Mice were considered as responders, when specific lysis≥10% was observed.

DNA Immunization in HLA-*B0702 Transgenic Mice

The LvCMV-hTERT plasmid vector encoding the hTERT gene under the control of CMV promoter was purified on plasmid Giga kit columns under endotoxin-free conditions (Qiagen). Anesthetized HLA-*B0702 Transgenic mice were injected with said plasmid (50 μg each side) into regenerating tibialis anterior muscles. 14 days after, spleen cells of individual mouse were re-activated in vitro with peptide-pulsed (10 μg/ml), syngenic γ-irradiated (50 Gy) LPS-lymphoblast in complete medium, supplemented with 10% supernatant from Con A-activated rat spleens cells. Cytotoxicity assays were performed 6 days as described.

Lentiviral Vector Construct and Production

The pTRIP-deltaU3-CMV-hTERT (referred as TRIPLv-hTERT or Lv-hTERT or pTrip-hTERT) (FIG. 7) construct was created by first subcloning an EcoRI-SalI hTERT insert derived from the pBABE-hygro-hTERT plasmid (Counter et al. Proc Natl Acad Sci U.S.A. 1998; 95: 14723-8) into the pSP73 vector (Promega). A BglII-SalI fragment was then inserted into the pTRIP-CMV plasmid cut with BamH1 and XhoI. Pseudo typed recombinant retroviral particles were produced by transient (48 h) transfection of 293T cells as described (Zennou et al. Cell 2000; 14; 101:173; Firat et al. J Gene Med 2002; 4:38-45). The recombinant retroviral particles were concentrated by ultra-centrifugation and resuspended in PBS. The amount of vector particles was estimated from that of p24 protein in a commercially available ELISA assay (NEN, DUPONT, France Perkin Elmer).

The pTRIP-CMV-ΔhTERT vector, deposited at the CNCM (Institut Pasteur, Paris, France) under the number CNCM 1-3660 on Jul. 28, 2006, was carried out as described in the paragraph above. However, the hTERT protein was rendered non-functional by deletion of amino acids 867 to 869, corresponding to nucleotides 2654 to 2662 of FIG. 1 (wild-type). The catalytically dead hTERT RT mutant (ΔhTERT) was generated by creating a deletion of amino acid residues 867 to 869 using the QUICKCHANGE XL Site-Directed Mutagenesis Kit (Stratagene) and verified by sequencing.

Immunization in MHC Class I Transgenic Mice and CTL Detection

Immunization with TRIPLv-hTERT was performed as a single subcutaneously (at the base of the tail) injection of 1500 ng of TripLv-hTERT suspension or control vector.

Immunization was performed in HLA.A2 transgenic mice as a single intraperitoneal injection of recombinant lentiviral particles, pTRIP-CMV-ΔhTERT or Trip-GFP as a control, equivalent to 1500 ng of p24 antigen in 500 µl of PBS.

12 days later, hTERT peptide-specific T among splenocytes were detected by an ELISPOT assay (see below). Cytotoxicity assays were performed on the same immune splenocyte populations after in vitro stimulation with peptide-pulsed as described above.

Evaluation of T-Cell Response by Ex Vivo IFN-γ ELISPOT Assay

Peptide-specific T cells from immunized mice were detected by IFN-γ ELISPOT assay as previously described (Miyahira et al. J Immunol Methods 1995; 181:45-54). Anti-mouse IFN-γ mAb's (3 µg/ml; Pharmigen, Becton Dickinson biosciences) were coated onto 96-well nitrocellulose microplates (multi screen; Millipore corp, Molsheim, France). After red cell lysis, freshly isolate spleen lymphocytes of individual mouse ($5 \times 10^5$, $2.5 \times 10^5$ and $1.25 \times 10^5$ cells/well) were directly cultured with or without 5 µg of native hTERT peptide for 18 h at 37° C. After washings, the plates were incubated 2 hours with biotinylated anti-mouse IFN-γ (2 µg/ml; Pharmigen, Becton Dickinson biosciences). Finally, the plates were washed and incubated at 37° C. for 1 h with alkaline phosphatase-conjugate streptavidin (Roche molecular biochemicals, Mannheim, germany). Positive controls include cells stimulated with phorbol myristate acetate (100 ng/ml, Sigma)) and ionomycin (1 µg/ml). IFNγ spot-forming cells (SFCs) were developed by adding peroxidase substrates (BCIP/NBT, Promega Corp, Madison W; USA) and counted using automated image analysis system a BIOREADER 2000 (Biosys, Karben, germany). The number of specific SFCs was calculated after subtracting negative control values (<10 SFC). Responses were positive if the mean of SFCs in stimulated well was greater than the mean+2 S. D. of the SFCs in the negative control wells and greater than 50 SFC/$10^6$ cells.

Cytolytic Assay

Cytotoxicity assays were performed by using standard 4-5 h $^{51}$Cr release assay as previously described (Firat et al. J Gene Med 2002; 4:38-45). Specific lysis in % was calculated by subtracting non-specific lysis observed with the control peptide. Mice were considered as responders when specific lysis≥10% was observed.

Generation of hTERT Peptide-Specific CTL in Human

Human CTL from donors were obtained after in vitro reactivated PBMC for 4 weeks with hTERT peptide HLA-B0702 restricted as described previously (Hernandez et al. Proc Natl Acad Sci U.S.A. 2002; 99:12275-80). Briefly, Ficoll-purified human PBMCS were thawed and incubated ($4 \times 10^6$/well) in 24-well plates in RPMI 1640, 1 mM sodium pyruvate, 100 IU/ml penicillin, 100 µg/ml streptomycin, 10 mM HEPES, $5 \times 10$-5M 2-mercaptoethanol supplemented with heat inactivated 10% human serum (Institut Jacques Boy, Reims, France). They were stimulated with each hTERT peptide (10 µg/ml) and recombinant human IL-7 (20 ng/ml; R&D Systems) was added.

On day 7, lymphocytes were re-activated with peptide-pulsed γ-irradiated autologous PBMCs (50 Gy). The next day, 20 IU/ml human IL-2 (Roche, Mannheim, Germany) was added to the culture. CTL lines were re-activated weekly during four cycles. For some donors, CD8$^+$ T cells were purified after three round cycle, using CD8 microbeads (Miltenyi Biotec, Bergisch Gladbach, Germany) according to manufacturer's recommendations and activated once before functional test. Cytolytic assays were performed 6 days after the last re-activation against various $^{51}$Cr-labeled targets: T2-B7 pulsed with tested hTERT peptides or irrelevant peptide, or tumor cell lines.

In some experiments, tumors cells were incubated with an anti-HLA class I framework mAb, w6/32 (BD Pharmigen) or anti-HLA-*B0702 mAb, ME.1, or an anti-HLA-DR mAbB, G46.6 (BD Pharmigen) at an optimal concentration (10 µg/mL) for 30 minutes to determine whether cytotoxicity was restricted to HLA class I.

II—Results

1. Immunogenicity of HLA-*B-0702 Predicted Peptides Derived from hTERT.

Using a T-cell epitope prediction program, we analysed the hTERT protein sequence and retained six peptides (3 nonamers and 3 decamers) due to their high predictive score (Table I). We next tested their ability to bind HLA-B0702 molecule using antigen-transporter (TAP)-deficient T2 cells transfected with HLA-B0702 gene (T2-B7). Three peptides p1, p4 and p68 respectively show a high relative affinity (RA≤1) and the three others p277, p342 and p351 exhibited medium RA>1 (Table I). These data indicate that these six peptides are excellent binders to HLA-B0702. Therefore, one might expect such complexes, formed in the endoplasmic reticulum, to reach the surface of tumor cells and be available for CTL recognition.

To test if these peptides are immunogenic in vivo, we have immunized HLA-*B0702 transgenic mice. The six peptides tested were shown to be able to induce CTL responses, although differences were noticed (Table I). Two peptides p4 and p68, binding with a high affinity to the HLA-B7 molecules, induce strong CTL response in all mice tested. In contrast, peptides (p277 and p342), having lower affinity for the HLA-B7 molecules, enable the generation of moderate specific CTL, in only 50% of mice tested. CTL lines specific for hTERT epitopes, generated from transgenic mice, recognized human T2-B7 pulsed with their respective specific peptides (data not shown), demonstrating the high affinity of their TCR for the complex MHC/peptide. Thus, there is an overall correlation between the results of binding/stabilization of HLAB0702 and the in vivo CTL response in HLA-B7 transgenic mice.

TABLE 1

Immunogenicity of selected hTERT HLA-*80702 binding peptide *

| | | | | | Immunogenicity‡ |
|---|---|---|---|---|---|
| Peptide* | Sequence | SEQ ID NO | Relative Score§ | Avidity+ | Specific Lysis R/T** (%) |
| p1 | MPRAPRCRA | 6 | 23 | 0.4 | 4/6 30, 39, 35, 28 |
| P4 | APRCRAVRSL | 7 | 25 | 0.3 | 6/6 52, 53, 48, 51, 46, 49 |

TABLE 1-continued

Immunogenicity of selected hTERT HLA-*80702 binding peptide *

| Peptide* | Sequence | SEQ ID NO | Score§ | Relative Avidity+ | Immunogenicity‡ R/T** | Specific Lysis (%) |
|---|---|---|---|---|---|---|
| p68 | APSFRQVSCL | 8 | 25 | 0.4 | 6/6 | 63, 78, 75, 69, 70, 72 |
| p277 | RPAEEATSL | 9 | 23 | 4.7 | 3/6 | 29, 33, 29 |
| p342 | RPSFLLSSL | 10 | 23 | 2.5 | 3/6 | 26, 39, 32, |
| p351 | RPSLTGARRL | 11 | 23 | 1.5 | 4/6 | 47, 31, 37, 26 |

*The figure represents the first amino acid of the peptide. Therefore, "p4" indicates that the alanine residue is the fourth amino acid of the coding sequence.
§Algorithm score obtained by using SYFPEITHI predictive program
+The relative avidity of hTERT peptides for HLA-B*0702 was measured by using a MHC stabilization assay in comparison with a reference peptide as detailed in material and methods.
‡HLA-B'0702 transgenic mice were immunized with candidate peptides (six mice for each peptide) as detailed above. Ten days later, spleen cells of individual mice were restimulated in vitro with each hTERT peptide. Cytolytic activities were assayed by 4-5 h 51Cr release assay using peptide loaded RMA-87 target cells. The Specific lysis was calculated by subtracting non-specific lysis observed with the R10TV control peptide. Specific lysis at a 75: 1 effector/target ratio was showed.
**RIT: responder (specific lysis 10%) versus tested mice.

2. hTERT-Derived Peptides were Processed in HLA-B0702 Transgenic Mice.

To assess the presentation of endogenously synthesized hTERT peptides in the context of the HLA-B0702 molecule against these six hTERT epitopes identified, HLA-*B0702 transgenic mice were immunised with cDNA encoding hTERT, forty days after peptide-specific CTL responses within spleen cells of individual mice were evaluated. As shown in FIG. 2, hTERT peptide-specific CTLs were induced in most immunized mice (M), from 50 to 80% of mice for p4, p68, p1, p277 and p351. In contrast, p342-specific CTLs can be induced in about 15% tested mice. No significant hTERT-specific CTL responses were also induced from non-immunized naïve mice. Thus, these six hTERT epitopes are effectively intracellular^ processed. Moreover, natural peptides similar in term of amino acid sequence or structure to the synthetic ones, are presented by the corresponding HLA-*B0702 molecules on the cell surface.

Further, these data show that multiple CTL specificity can be induced simultaneously against several hTERT epitopes in a single mice and validate our HLA-Class I transgenic mouse model for their potential to test candidate vaccines.

3. Induction of Primary CTL Responses from Healthy Donors by hTERT Peptides.

We studied whether hTERT peptides would be effective in raising HLA-B7-restricted CTLs, using PBMCs of HLA-B0702 healthy donors in an in vitro immunization protocol. CTL responses were generated in eight out of ten individuals ($d_1$ to $d_8$), and peptide-specific CTL responses were obtained in at least 50% of donors, except for p342 (20%) (FIG. 3). hHTERT epitope recognition by in vitro generated CTLs varies among donors, depending upon their genetic background (FIG. 3). Therefore, by random testing of HLA-B0702 healthy donors, it was clearly established that these hTERT peptides are immunogenic in human, implying that specific CTL precursors for hTERT are not deleted in the peripheral adult repertoire. Therefore, we asked whether CTL lines generated from healthy donors would be able to kill HLA-matched hTERT+ tumor cells.

4. Specific hTERT CTL were Able to Lyse Tumors of Differents Origins hTERT-specific CTLs from donors were tested for their capacity to lyse human tumour cell lines of different origins. The results presented in Table 2 show that, CTL lines generated in vitro from healthy donors killed HLA-B0702+ tumour cells, whereas no cytotoxicity against HLA-B0702'tumors was detected. (See for example CTLp351 in $d_1$, $d_2$ and $d_3$ in KU L268 or 293-UT target (respectively 52, 25, 20 and 34, 41 and 19%) versus T1 or BBG1 target (respectively 9, 2, 6 and 0, 0, 2%). Differences were observed in tumor recognition according to the CTL specificity; this could be explained by differential presentation of hTERT peptides on the surface of the tumor cells. Importantly, p351-specific CTL lines generated from different donors recognize the majority of tumor cell lines tested (Table 2). In contrast, all p4-specific CTL lines do not lyse all the type of tested tumors. CTL lines, specific for p1 and p68 peptides, only recognize the T1-B7 targets. p342-specific CTL lines recognize only melanoma cells (LB 34 and KU 268 target). Finally, p277-specific CTL lines recognize renal cancer (293 UT) but neither melanoma nor lymphoid tumor cells. On the other hand, normal PBMCs and CD40 activated B cells were not lysed by these hTERT peptide-specific CTL lines, regardless of HLA type (two last lines of Table 2).

As shown in FIG. 4, the cytotoxic activity of CTLp351 line toward HLA-B7+ tumor cells is inhibited by an anti-class I mAb anti-HLA-B0702, but not by an anti-HLADR mAb (MHC class II). Similar data were obtained with other peptide-specific CTL lines (data not shown) and suggest that CTL lines exert cytotoxicity against hTERT+ tumor cells in an HLA-B0702-restricted manner. Collectively, these results show that these six hTERT derived peptides are not equally naturally expressed at the tumor cell surface and that hTERT peptide-specific CTLs can discriminate between tumor cells and normal cells, through the recognition of hTERT peptide in context of HLA-B0702 molecules.

5. Lentiviral Vector Encoding hTERT Vaccination Induces Efficient Peptide-Specific T Cell Responses in Mice.

We next tested candidate vaccines, comprising either a full-length hTERT gene or a non-functional hTERT gene, inserted in a HIV-derived flap vector (FIG. 7). Previous data have shown that lentiviral vectors of this type target dendritic cells in vitro and in vivo, and induce strong poly-specific anti tumor CTL responses in animals. Therefore, we immunized HLA-*B0702 transgenic mice with either recombinant Lv-hTERT or with pTRIP-CMV-ΔhTERT. Twelve days after, spleen cells of individual mice were evaluated by an ex vivo ELISPOT assay.

As shown in FIG. 5A, peptide-specific CD8$^+$ T cell responses were obtained against HLA-B0702 restricted hTERT epitopes, as compared with mice that received Lv-GFP control vector. Functional analysis of the induced peptide-specific CD8$^+$ cells in chromium release assay after in vitro stimulation confirmed ex vivo ELISPOT data (Table 3) and show that efficient specific CTL response is generated against these six peptides in about 50-70% of mice after a single injection of Lv-hTERT and in 100% of the mice after a boost with TRIPLv-hTERT (FIG. 6). This was also associated with strong CTL responses in all mice (Table 3). Additionally, as show in Table 3, immunization of HHD mice transgenic for HLA-A2.1 with the same vector induced potent CTL responses specific for two HLA-A2.1.1 restricted epitopes previously classified as dominant (p540) and cryptic (p572). Collectively, these results clearly show that administration of Lv-hTERT result in the induction of very efficient multi-specific T cell response in mice, supporting that hTERT could serve as polyepitope and polyallelic TAA for cancer immunotherapy.

As shown in FIG. 8, hTERT peptide-specific CD8$^+$ T cell responses were detected ex vivo in HLA-A2 transgenic (Tg) mice after a single injection of recombinant pTRIP-CMV-ΔhTERT. We showed that CD8$^+$ T cells specific for p540 and PY572 epitopes were induced at least in 50% of immunized mice (FIG. 8). These results clearly showed that the two epitopes were correctly endogenously processed and presented in HLA-A2 Tg mice after immunization with pTRIP-CMV-ΔhTERT.

Collectively, these results showed that a single injection of TRIP-hTERT resulted in the induction of a potent multi-specific anti-hTERT CD8$^+$ T-cells response in both HLA transgenic mice groups.

TABLE 2 anti-hTRT CTL from normal donors lyses tumor cells of various types

| | | | \multicolumn{18}{c}{Percent lysis*} |
| | | | CTL p1 | | | CTL p4 | | | CTL p68 | | | CTL p277 | | | CTL p342 | | | CTL p351 | | |
| Cell target | Cell type | HLA-B7 | d1 | d6 | d8 | d1 | d6 | d8 | d1 | d6 | d8 | d1 | d6 | d8 | d1 | d6 | d8 | d1 | d6 | d8 |
|---|---|---|---|---|---|---|---|---|---|---|---|---|---|---|---|---|---|---|---|---|---|
| T1 | T-B hybrid | = | 9 | 10 | 5 | 8 | 6 | nd | 0 | 7 | 6 | 3 | 5 | 9 | 3 | 6 | 4 | 9 | 2 | 6 |
| T1-B7 | T-B hybrid | + | 29 | 26 | 14 | 5 | 7 | nd | 19 | 30 | 4 | 56 | 30 | 12 | 2 | 17 | 5 | 38 | 24 | 31 |
| Sk23mel | Melanoma | − | 0 | 1 | 0 | 0 | 2 | 0 | 10 | 3 | 4 | 1 | 4 | 0 | 4 | 4 | 3 | 5 | 2 | 1 |
| LB34 | Melanoma | + | 5 | 4 | 0 | 0 | 4 | 2 | 13 | 7 | 11 | 0 | 0 | 2 | 28 | 22 | 11 | 52 | 25 | 20 |
| KUL68 | Melanoma | + | 9 | 4 | 7 | 6 | 3 | 0 | 0 | nd | 0 | 7 | 4 | nd | 26 | 14 | 9 | 34 | 41 | 19 |
| 293-UT | Renal cell | + | 2 | 8 | 4 | 1 | 6 | 7 | 3 | 0 | 0 | 36 | 17 | 22 | 9 | 17 | 4 | 28 | 22 | 25 |
| BBG1 | EBV-B cell | − | 0 | 4 | 3 | 0 | 0 | 2 | 2 | 0 | 1 | 0 | 0 | 5 | 1 | 1 | 0 | 0 | 0 | 2 |
| JY | EBV-B cell | + | 2 | 0 | 4 | 0 | 6 | nd | 0 | 0 | 9 | 3 | 0 | 1 | 8 | 10 | 6 | 27 | 18 | 15 |
| Raji | B lymphoma | − | 4 | 1 | nd | 5 | 0 | nd | 0 | 0 | nd | 6 | nd | 1 | 0 | nd | 0 | 4 | 0 | nd |
| Autologous PBMC | Normal cell | + | 0 | 0 | 0 | 4 | 0 | 1 | 0 | 0 | 0 | 0 | 0 | 1 | 0 | 2 | 0 | 0 | 0 | 1 |
| Autologous B cell CD40§ | Normal cell | + | 0 | 0 | 0 | 3 | 0 | 2 | 2 | 0 | 0 | 0 | 0 | 6 | 0 | 2 | 3 | 0 | 0 | 4 |

*hTERT peptide specific-CTL lines (CTLp1, CTLp4, CTLp68, CTLp277, CTLp342, CTLp351) were obtained from healthy donors that were responder after subsequent in vitro immunization as described in material and methods. Cytotoxicity was measured in a standard $^{51}$Cr = labeled release assay. Specific lysis; for a 30:1 effector:target ratio were shown
§Autologous B lymphpcytes from normal donors were activated for 48 h with a trimeric CD40 L (40 µg/ml).

TABLE 3

Induction of CTL responses following Lv-hTERT immunization
Flap+-Lv-hTRT immunization

| HLA-B7 Tg mice | | | HHD mice | | |
|---|---|---|---|---|---|
| Restimulating peptide | R/T | Specific lysis (%) | Restimulating peptide | R/T | Specific lysis (%) |
| P1 | 4/8 | 27, 30, 29, 32 | P540 | 2/6 | 21, 18 |
| p4 | 6/8 | 18, 25, 54, 33, 16 | pY572 | 5/6 | 22, 19, 14, 35, 24 |
| p68 | 4/8 | 15, 64, 24, 16, | | | |
| p277 | 5/8 | 21, 25, 23, 52, 33 | | | |
| p342 | 4/8 | 18, 24, 20, 37 | | | |
| p351 | 5/8 | 17, 20, 18, 36, 19 | | | |

III—Conclusion

New hTERT epitopes, which are in vivo immunogenic and processed in H-2-class I knockout HLA-B0702 transgenic mice have identified. Further, in vitro, hTERT peptide immunization using HLA-B702$^+$ PBL from healthy donors induce specific CTL responses recognizing hTERT$^+$ tumors from various origins, implying that there is no deletion in the human T cell repertoire for these epitopes. Moreover, it was shown that depending upon the tumor origins, peptides repertoire expressed on the cell surface could be qualitatively different, underlining, the utility to characterize hTERT as polyepitope tumor associated antigens for circumvent antigenic variability of cancer cells. Finally, a humanized HLA-*B0702 and HLA-A2 1 transgenic mice were used, to test a candidate vaccine consisting of a nonfunctional telomerase gene inserted in a new generation of lentiviral derived flap vector. A strong hTERT specific CD8$^+$ T cell responses were observed in all the HLA-transgenic mice. These data support the use for therapeutic vaccination in cancer patients and extend the potential applicability of hTERT as a therapeutic target to cover a large population of cancer patients.

BIBLIOGRAPHY

Schroers R, Huang X F, Hammer J, Zhang J, Chen S Y Identification of HLA DR7-restricted epitopes from human telomerase reverse transcriptase recognized by CD4+ T-helper cells. Cancer Res. 2002 May 1; 62(9): 2600-5.

Vonderheide R H, Domchek S M, Schultze J L, George D J, Hoar K M, Chen D Y, Stephans K F, Masutomi K, Loda M, Xia Z, Anderson K S, Hahn W C, Nadler L M. Vaccination of cancer patients against telomerase induces functional antitumor CD8+ T lymphocytes. Clin Cancer Res. 2004 Feb. 1; 10(3):828-39.

Gross D A, Graff-Dubois S, Opolon P, Cornet S, Alves P, Bennaceur-Griscelli A, Faure O, Guillaume P, Firat H, Chouaib S, Lemonnier F A, Davoust J, Miconnet I, Vonderheide R H, Kosmatopoulos K. High vaccination efficiency of low-affinity epitopes in antitumor immunotherapy. J Clin Invest. 2004 February; 113(3):425-33.

Scardino A, Gross D A, Alves P, Schultze J L, Graff-Dubois S, Faure O, Tourdot S, Chouaib S, Nadler L M, Lemonnier F A, Vonderheide R H, Cardoso A A, Kosmatopoulos K. HER-2/neu and hTERT cryptic epitopes as novel targets for broad spectrum tumor immunotherapy. J Immunol. 2002 Jun. 1; 168(11):5900-6.

Vonderheide R H, Schultze J L, Anderson K S, Maecker B, Butler M O, Xia Z, Kuroda M J, von Bergwelt-Baildon M S, Bedor M M, Hoar K M, Schnipper D R, Brooks M W, Letvin N L, Stephans K F, Wucherpfennig K W, Hahn W C, Nadler L M. Equivalent induction of telomerase-specific cytotoxic T lymphocytes from tumor-bearing patients and healthy individuals. Cancer Res. 2001 Dec. 1; 61(23):8366-70.

Vonderheide R H, Anderson K S, Hahn W C, Butler M O, Schultze J L, Nadler L M. Characterization of HLA-A3-restricted cytotoxic T lymphocytes reactive against the widely expressed tumor antigen telomerase. Clin Cancer Res. 2001 November; 7(11):3343-8.

Vonderheide R H, Hahn W C, Schultze J L, Nadler L M. The telomerase catalytic subunit is a widely expressed tumor-associated antigen recognized by cytotoxic T lymphocytes. Immunity. 1999 June; 10(6):673-9.

Minev B, Hipp J, Firat H, Schmidt J D, Langlade-Demoyen P, Zanetti M. Cytotoxic T cell immunity against telomerase reverse transcriptase in humans. Proc Natl Acad Sci USA. 2000 Apr. 25; 97(9):4796-801.

Hernandez J, Garcia-Pons F, Lone Y C, Firat H, Schmidt J D, Langlade-Demoyen P, Zanetti M. Identification of a human telomerase reverse transcriptase peptide of low affinity for HLA A2.1 that induces cytotoxic T lymphocytes and mediates lysis of tumor cells. Proc Natl Acad Sci USA. 2002 Sep. 17; 99(19): 12275-80. Epub 2002 Sep. 6.

Arai J, Yasukawa M, Ohminami H, Kakimoto M, Hasegawa A$_1$ Fujita S. Identification of human telomerase reverse transcriptase-derived peptides that induce HLA-A24-restricted antileukemia cytotoxic T lymphocytes. Blood. 2001 May 1; 97(9):2903-7.

Rohrlich P S, Cardinaud S, LuIe J, Montero-Julian F A, Prodhomme V, Firat H, Davignon J L, Perret E, Monseaux S, Necker A, Michelson S, Lemonnier F A, Chameau P$_1$ Davrinche C. Use of a lentiviral vector encoding a HCMV-chimeric IE1-pp65 protein for epitope identification in HLA-Transgenic mice and for ex vivo stimulation and expansion of CD8(+) cytotoxic T cells from human peripheral blood cells. Hum Immunol. 2004 May; 65(5): 514-22.

Firat H$_1$ Zennou V, Garcia-Pons F, Ginhoux F, Cochet M, Danos O, Lemonnier F A, Langlade-Demoyen P, Charneau P. Use of a lentiviral flap vector for induction of CTL immunity against melanoma. Perspectives for immunotherapy. J Gene Med. 2002 January-February; 4(1):38-45.

Ayyoub M, Migliaccio M, Guillaume P, Lienard D, Cerottini J C, Romero P, Levy F, Speiser D E, Valmori D. Lack of tumor recognition by hTERT peptide 540-548-specific CD8(+) T cells from melanoma patients reveals inefficient antigen processing. Eur J Immunol. 2001 September; 31 (9):2642-51.

Esslinger C$_1$ Chapatte L, Finke D, Miconnet I$_1$ Guillaume P, Levy F, MacDonald H R. In vivo administration of a lentiviral vaccine targets DCs and induces efficient CD8 (+) T cell responses. J Clin Invest. 2003 June; 111 (11):1673-81.

Esslinger C, Romero P$_1$ MacDonald H R. Efficient transduction of dendritic cells and induction of a T-cell response by third-generation lentivectors. Hum Gene Ther. 2002 Jun. 10; 13(9): 1091-100.

Parkhurst M R, Riley J P$_1$ Igarashi T, Li Y$_1$ Robbins P F, Rosenberg S A. Immunization of patients with the hTERT:540-548 peptide induces peptide-reactive T lymphocytes that do not recognize tumors endogenously expressing telomerase. Clin Cancer Res. 2004 Jul. 15; 10(14):4688-98.

Firat H$_1$ Garcia-Pons F$_1$ Tourdot S$_1$ Pascolo S$_1$ Scardino A, Garcia Z, Michel ML$_1$ Jack R W, Jung G, Kosmatopoulos K, Mateo L, Suhrbier A, Lemonnier FA$_1$ Langlade-Demoyen P. H-2 class I knockout, HLA-A2.1-transgenic mice: a versatile animal model for preclinical evaluation of antitumor immunotherapeutic strategies. Eur J Immunol. 1999 October; 29(10):3112-21.

Frolkis M, Fischer M B$_1$ Wang Z$_1$ Lebkowski J S$_1$ Chiu C P, Majumdar A S. Dendritic cells reconstituted with human telomerase gene induce potent cytotoxic T-cell response against different types of tumors. Cancer Gene Ther. 2003 March; 10(3):239-49.

Vonderheide R H. Telomerase as a universal tumor-associated antigen for cancer immunotherapy. Oncogene. 2002 Jan. 21; 21(4):674-9. Review.

Sun B1 Huang Q1 Liu S, Chen M1 Hawks C L, Wang L, Zhang C, Hornsby P J. Progressive loss of malignant behavior in telomerase-negative tumorigenic adrenocortical cells and restoration of tumorigenicity by human telomerase reverse transcriptase. Cancer Res. 2004 Sep. 1; 64(17):6144-51.

Tajima K, Ito Y, Demachi A, Nishida K, Akatsuka Y, Tsujimura K1 Hida T, Morishima Y, Kuwano H1 Mitsudomi T1 Takahashi T, Kuzushima K. Interferon-gamma differentially regulates susceptibility of lung cancer cells to telomerase-specific cytotoxic T lymphocytes, Int J Cancer. 2004 Jun. 20; 110(3):403-12.

Su Z, Vieweg J, Weizer A Z, Dahm P, Yancey D1 Turaga V, Higgins J1 Boczkowski D, Gilboa E, Dannull J. Enhanced induction of telomerase-specific CD4(+) T cells using dendritic cells transfected with RNA encoding a chimeric gene product. Cancer Res. 2002 Sep. 1; 62(17):5041-8.

Heiser A, Maurice M A, Yancey D R, Coleman D M, Dahm P, Vieweg J. Human dendritic cells transfected with renal tumor RNA stimulate polyclonal T-cell responses against antigens expressed by primary and metastatic tumors. Cancer Res. 2001 Apr. 15; 61(8):3388-93.

Breckpot K1 Dullaers M1 Bonehill A, van Meirvenne S, Heirman C, de Greef C, van der Bruggen P, Thielemans K. Lentivirally transduced dendritic cells as a tool for cancer immunotherapy. J Gene Med. 2003 August; 5(8): 654-67.

The invention claimed is:

1. A method of inducing an HLA-A2 and/or HLA-B7-restricted immune response against at least one hTERT epitope, comprising:
   A) administering to an animal a lentiviral vector comprising a polynucleotide sequence that encodes a modified hTERT protein comprising the amino acid sequence of SEQ ID NO: 39;
   B) expressing the modified hTERT protein; and
   C) inducing:
      1) an HLA-A2-restricted immune response against at least one hTERT epitope selected from:
         a) p540, and
         b) pY572; and/or
      2) inducing an HLA-B7-restricted immune response against at least one hTERT epitope selected from:
         a) MPRAPRCRA (SEQ ID NO:6) (p1),
         b) APRCRAVRSL (SEQ ID NO:7) (p4),
         c) APSFRQVSCL (SEQ ID NO:8) (p68),
         d) RPAEEATSL (SEQ ID NO:9) (p277),
         e) RPSFLLSSL (SEQ ID NO:10) (p342), and
         f) RPSLTGARRL (SEQ ID NO:11) (p351).

2. The method of claim 1, wherein the lentiviral vector comprising the polynucleotide sequence that encodes a modified hTERT protein is the pTRIP-CMV-ΔhTERT vector deposited at the CNCM under the number I-3660 on Jul. 28, 2006.

3. The method of claim 1, further comprising providing antigen presenting cells (APCs), transforming the APCs in vitro with the lentiviral vector comprising the polynucleotide sequence that encodes a modified hTERT protein, and administering the APCs to the animal.

4. The method of claim 3, wherein the APCs are dendritic cells.

5. The method of claim 1, wherein the animal is a human.

6. The method of claim 1, the method comprising inducing an HLA-A2-restricted immune response against the hTERT epitopes a) p540 and b) pY572.

7. The method of claim 6, wherein the lentiviral vector comprising the polynucleotide sequence that encodes a modified hTERT protein is the pTRIP-CMV-ΔhTERT vector deposited at the CNCM under the number I-3660 on Jul. 28, 2006.

8. The method of claim 6, further comprising providing antigen presenting cells (APCs), transforming the APCs in vitro with the lentiviral vector comprising the polynucleotide sequence that encodes a modified hTERT protein, and administering the APCs to the animal.

9. The method of claim 8, wherein the APCs are dendritic cells.

10. The method of claim 6, wherein the animal is a human.

11. The method of claim 1, the method comprising inducing an HLA-B7-restricted immune response against at least two hTERT epitopes selected from:
    a. MPRAPRCRA (SEQ ID NO:6) (p1),
    b. APRCRAVRSL (SEQ ID NO:7) (p4),
    c. APSFRQVSCL (SEQ ID NO:8) (p68),
    d. RPAEEATSL (SEQ ID NO:9) (p277),
    e. RPSFLLSSL (SEQ ID NO:10) (p342), and
    f. RPSLTGARRL (SEQ ID NO:11) (p351).

12. The method of claim 11, wherein the lentiviral vector comprising the polynucleotide sequence that encodes a modified hTERT protein is the pTRIP-CMV-ΔhTERT vector deposited at the CNCM under the number I-3660 on Jul. 28, 2006.

13. The method of claim 11, further comprising providing antigen presenting cells (APCs), transforming the APCs in vitro with the lentiviral vector comprising the polynucleotide sequence that encodes a modified hTERT protein, and administering the APCs to the animal.

14. The method of claim 13, wherein the APCs are dendritic cells.

15. The method of claim 11, wherein the animal is a human.

16. The method of claim 1, the method comprising inducing an HLA-B7-restricted immune response against each of hTERT epitopes:
    a. MPRAPRCRA (SEQ ID NO:6) (p1),
    b. APRCRAVRSL (SEQ ID NO:7) (p4),
    c. APSFRQVSCL (SEQ ID NO:8) (p68),
    d. RPAEEATSL (SEQ ID NO:9) (p277),
    e. RPSFLLSSL (SEQ ID NO:10) (p342), and
    f. RPSLTGARRL (SEQ ID NO:11) (p351).

17. The method of claim 16, wherein the lentiviral vector comprising the polynucleotide sequence that encodes a modified hTERT protein is the pTRIP-CMV-ΔhTERT vector deposited at the CNCM under the number I-3660 on Jul. 28, 2006.

18. The method of claim 16, further comprising providing antigen presenting cells (APCs), transforming the APCs in vitro with the lentiviral vector comprising the polynucleotide sequence that encodes a modified hTERT protein, and administering the APCs to the animal.

19. The method of claim 18, wherein the APCs are dendritic cells.

20. The method of claim 16, wherein the animal is a human.

* * * * *

SEQUENCE LISTING

```
<160> NUMBER OF SEQ ID NOS: 41

<210> SEQ ID NO 1
<211> LENGTH: 9
<212> TYPE: PRT
<213> ORGANISM: artificial
<220> FEATURE:
<223> OTHER INFORMATION: hTERT

<400> SEQUENCE: 1

Ile Leu Ala Lys Phe Leu His Trp Leu
1               5

<210> SEQ ID NO 2
<211> LENGTH: 9
<212> TYPE: PRT
<213> ORGANISM: artificial
<220> FEATURE:
<223> OTHER INFORMATION: hTERT

<400> SEQUENCE: 2

Ala Pro Arg Cys Arg Ala Val Arg Ser
1               5

<210> SEQ ID NO 3
<211> LENGTH: 9
<212> TYPE: PRT
<213> ORGANISM: artificial
<220> FEATURE:
<223> OTHER INFORMATION: hTERT

<400> SEQUENCE: 3

Lys Leu Phe Gly Val Leu Arg Leu Lys
1               5

<210> SEQ ID NO 4
<211> LENGTH: 9
<212> TYPE: PRT
<213> ORGANISM: artificial
<220> FEATURE:
<223> OTHER INFORMATION: hTERT

<400> SEQUENCE: 4

Val Tyr Ala Glu Thr Lys His Phe Leu
1               5

<210> SEQ ID NO 5
<211> LENGTH: 9
<212> TYPE: PRT
<213> ORGANISM: artificial
<220> FEATURE:
<223> OTHER INFORMATION: hTERT
```

<400> SEQUENCE: 5

Val Tyr Gly Phe Val Arg Ala Cys Leu
1               5

<210> SEQ ID NO 6
<211> LENGTH: 9
<212> TYPE: PRT
<213> ORGANISM: artificial
<220> FEATURE:
<223> OTHER INFORMATION: p1 polypeptide

<400> SEQUENCE: 6

Met Pro Arg Ala Pro Arg Cys Arg Ala
1               5

<210> SEQ ID NO 7
<211> LENGTH: 10
<212> TYPE: PRT
<213> ORGANISM: artificial
<220> FEATURE:
<223> OTHER INFORMATION: p4 polypeptide

<400> SEQUENCE: 7

Ala Pro Arg Cys Arg Ala Val Arg Ser Leu
1               5                   10

<210> SEQ ID NO 8
<211> LENGTH: 10
<212> TYPE: PRT
<213> ORGANISM: artificial
<220> FEATURE:
<223> OTHER INFORMATION: p68 polypeptide

<400> SEQUENCE: 8

Ala Pro Ser Phe Arg Gln Val Ser Cys Leu
1               5                   10

<210> SEQ ID NO 9
<211> LENGTH: 9
<212> TYPE: PRT
<213> ORGANISM: artificial
<220> FEATURE:
<223> OTHER INFORMATION: p277 polypeptide

<400> SEQUENCE: 9

Arg Pro Ala Glu Glu Ala Thr Ser Leu
1               5

<210> SEQ ID NO 10
<211> LENGTH: 9
<212> TYPE: PRT
<213> ORGANISM: artificial
<220> FEATURE:
<223> OTHER INFORMATION: p342 polypeptide

<400> SEQUENCE: 10

Arg Pro Ser Phe Leu Leu Ser Ser Leu
1               5

<210> SEQ ID NO 11
<211> LENGTH: 10
<212> TYPE: PRT
<213> ORGANISM: artificial
<220> FEATURE:
<223> OTHER INFORMATION: p351 polypeptide

```
<400> SEQUENCE: 11

Arg Pro Ser Leu Thr Gly Ala Arg Arg Leu
1               5                   10

<210> SEQ ID NO 12
<211> LENGTH: 9
<212> TYPE: PRT
<213> ORGANISM: artificial
<220> FEATURE:
<223> OTHER INFORMATION: p444 polypeptide

<400> SEQUENCE: 12

Asp Pro Arg Arg Leu Val Gln Leu Leu
1               5

<210> SEQ ID NO 13
<211> LENGTH: 9
<212> TYPE: PRT
<213> ORGANISM: artificial
<220> FEATURE:
<223> OTHER INFORMATION: p464 polypeptide

<400> SEQUENCE: 13

Phe Val Arg Ala Cys Leu Arg Arg Leu
1               5

<210> SEQ ID NO 14
<211> LENGTH: 9
<212> TYPE: PRT
<213> ORGANISM: artificial
<220> FEATURE:
<223> OTHER INFORMATION: p966 polypeptide

<400> SEQUENCE: 14

Ala Gly Arg Asn Met Arg Arg Lys Leu
1               5

<210> SEQ ID NO 15
<211> LENGTH: 9
<212> TYPE: PRT
<213> ORGANISM: artificial
<220> FEATURE:
<223> OTHER INFORMATION: p1107 polypeptide

<400> SEQUENCE: 15

Leu Pro Gly Thr Thr Leu Thr Ala Leu
1               5

<210> SEQ ID NO 16
<211> LENGTH: 9
<212> TYPE: PRT
<213> ORGANISM: artificial
<220> FEATURE:
<223> OTHER INFORMATION: p1123 polypeptide

<400> SEQUENCE: 16

Leu Pro Ser Pro Lys Phe Thr Ile Leu
1               5

<210> SEQ ID NO 17
<211> LENGTH: 9
<212> TYPE: PRT
<213> ORGANISM: Artificial
<220> FEATURE:
<223> OTHER INFORMATION: p444* peptide

<400> SEQUENCE: 17
```

```
Ala Pro Arg Arg Leu Val Gln Leu Leu
1               5

<210> SEQ ID NO 18
<211> LENGTH: 9
<212> TYPE: PRT
<213> ORGANISM: Artificial
<220> FEATURE:
<223> OTHER INFORMATION: hTERT
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (3)..(8)
<223> OTHER INFORMATION: Xaa= any amino acid
<220> FEATURE:
<221> NAME/KEY: MISC_FEATURE
<222> LOCATION: (9)..(9)
<223> OTHER INFORMATION: Xaa is selected from the group consisting of
      A,L,I,M,V,F,W and Y

<400> SEQUENCE: 18

Xaa Pro Xaa Xaa Xaa Xaa Xaa Xaa Xaa
1               5

<210> SEQ ID NO 19
<211> LENGTH: 10
<212> TYPE: PRT
<213> ORGANISM: Artificial
<220> FEATURE:
<223> OTHER INFORMATION: hTERT
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (3)..(9)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa is selected from the group consisting of
      A,L,I,M,V,F,W and  Y

<400> SEQUENCE: 19

Xaa Pro Xaa Xaa Xaa Xaa Xaa Xaa Xaa Xaa
1               5                   10

<210> SEQ ID NO 20
<211> LENGTH: 57
<212> TYPE: PRT
<213> ORGANISM: Artificial
<220> FEATURE:
<223> OTHER INFORMATION: hTERT

<400> SEQUENCE: 20

Met Pro Arg Ala Pro Arg Cys Arg Ala Ala Pro Arg Cys Arg Ala Val
1               5                   10                  15

Arg Ser Leu Ala Pro Ser Phe Arg Gln Val Ser Cys Leu Arg Pro Ala
            20                  25                  30

Glu Glu Ala Thr Ser Leu Arg Pro Ser Phe Leu Leu Ser Ser Leu Arg
        35                  40                  45

Pro Ser Leu Thr Gly Ala Arg Arg Leu
    50                  55
```

<210> SEQ ID NO 21
<211> LENGTH: 27
<212> TYPE: DNA
<213> ORGANISM: Artificial
<220> FEATURE:
<223> OTHER INFORMATION: n1 polynucleotide

<400> SEQUENCE: 21
atgccgcgcg ctccccgctg ccgagcc                                       27

<210> SEQ ID NO 22
<211> LENGTH: 30
<212> TYPE: DNA
<213> ORGANISM: Artificial
<220> FEATURE:
<223> OTHER INFORMATION: n4 polynucleotide

<400> SEQUENCE: 22
gctccccgct gccgagccgt gcgctccctg                                    30

<210> SEQ ID NO 23
<211> LENGTH: 30
<212> TYPE: DNA
<213> ORGANISM: Artificial
<220> FEATURE:
<223> OTHER INFORMATION: n68 polynucleotide

<400> SEQUENCE: 23 gcccctcct tccgccaggt gtcctgcctg                                     30

<210> SEQ ID NO 24
<211> LENGTH: 27
<212> TYPE: DNA
<213> ORGANISM: Artificial
<220> FEATURE:
<223> OTHER INFORMATION: n277 polynucleotide

<400> SEQUENCE: 24
agacccgccg aagaagccac ctctttg                                       27

<210> SEQ ID NO 25
<211> LENGTH: 27
<212> TYPE: DNA
<213> ORGANISM: Artificial
<220> FEATURE:
<223> OTHER INFORMATION: n342 polynucleotide

<400> SEQUENCE: 25 cggcccctcct tcctactcag ctctctg                                      27

<210> SEQ ID NO 26
<211> LENGTH: 30
<212> TYPE: DNA
<213> ORGANISM: Artificial
<220> FEATURE:
<223> OTHER INFORMATION: n351 polynucleotide

<400> SEQUENCE: 26
aggcccagcc tgactggcgc tcggaggctc                                    30

<210> SEQ ID NO 27
<211> LENGTH: 27
<212> TYPE: DNA
<213> ORGANISM: Artificial
<220> FEATURE:
<223> OTHER INFORMATION: n444 polynucleotide -continued

<400> SEQUENCE: 27
gacccccgtc gcctggtgca gctgctc                    27

<210> SEQ ID NO 28
<211> LENGTH: 27
<212> TYPE: DNA
<213> ORGANISM: Artificial
<220> FEATURE:
<223> OTHER INFORMATION: n464 polynucleotide

<400> SEQUENCE: 28
ttcgtgcggg cctgcctgcg ccggctg                    27

<210> SEQ ID NO 29
<211> LENGTH: 27
<212> TYPE: DNA
<213> ORGANISM: Artificial
<220> FEATURE:
<223> OTHER INFORMATION: n966 polynucleotide

<400> SEQUENCE: 29
gctgggagga acatgcgtcg caaactc                    27

<210> SEQ ID NO 30
<211> LENGTH: 27
<212> TYPE: DNA
<213> ORGANISM: Artificial
<220> FEATURE:
<223> OTHER INFORMATION: n1107 polynucleotide

<400> SEQUENCE: 30
ctcccgggga cgacgctgac tgccctg                    27

<210> SEQ ID NO 31
<211> LENGTH: 27
<212> TYPE: DNA
<213> ORGANISM: Artificial
<220> FEATURE:
<223> OTHER INFORMATION: n1123 polynucleotide

<400> SEQUENCE: 31
ctgccctcag acttcaagac catcctg                    27

<210> SEQ ID NO 32
<211> LENGTH: 27
<212> TYPE: DNA
<213> ORGANISM: Artificial
<220> FEATURE:
<223> OTHER INFORMATION: n444* polynucleotide

<400> SEQUENCE: 32
gccccccgtc gcctggtgca gctgctc                    27

<210> SEQ ID NO 33
<211> LENGTH: 10
<212> TYPE: PRT
<213> ORGANISM: Artificial
<220> FEATURE:
<223> OTHER INFORMATION: R10TV

<400> SEQUENCE: 33

Arg Pro His Glu Arg Asn Gly Phe Thr Val
1               5                   10

<210> SEQ ID NO 34

```
<211> LENGTH: 9
<212> TYPE: PRT
<213> ORGANISM: Artificial
<220> FEATURE:
<223> OTHER INFORMATION: human immunodeficiency virus type 1

<400> SEQUENCE: 34

Ile Pro Arg Arg Ile Arg Gln Gly Leu
1               5

<210> SEQ ID NO 35
<211> LENGTH: 13
<212> TYPE: PRT
<213> ORGANISM: Artificial
<220> FEATURE:
<223> OTHER INFORMATION: hepatitis B virus core 128-140

<400> SEQUENCE: 35

Thr Pro Pro Ala Thr Arg Pro Pro Asn Ala Pro Ile Leu
1               5                   10

<210> SEQ ID NO 36
<211> LENGTH: 4015
<212> TYPE: DNA
<213> ORGANISM: Homo sapiens
<220> FEATURE:
<221> NAME/KEY: misc_feature
<222> LOCATION: (1)..(4015)
<223> OTHER INFORMATION: gene encoding the hTERT protein and
      corresponding amino acid sequence
<220> FEATURE:
<221> NAME/KEY: CDS
<222> LOCATION: (56)..(3454)
<223> OTHER INFORMATION: coding sequence

<400> SEQUENCE: 36
gcagcgctgc gtcctgctgc gcacgtggga agccctggcc ccggccaccc ccgcg atg    58
                                                              Met
                                                              1 ccg cgc gct ccc cgc tgc cga gcc gtg cgc tcc ctg ctg cgc agc cac    106
Pro Arg Ala Pro Arg Cys Arg Ala Val Arg Ser Leu Leu Arg Ser His
        5                  10                  15 tac cgc gag gtg ctg ccg ctg gcc acg ttc gtg cgg cgc ctg ggg ccc    154
Tyr Arg Glu Val Leu Pro Leu Ala Thr Phe Val Arg Arg Leu Gly Pro
     20                  25                  30 cag ggc tgg cgg ctg gtg cag cgc ggg gac ccg gcg gct ttc cgc gcg    202
Gln Gly Trp Arg Leu Val Gln Arg Gly Asp Pro Ala Ala Phe Arg Ala
 35                  40                  45 ctg gtg gcc cag tgc ctg gtg tgc gtg ccc tgg gac gca cgg ccg ccc    250
Leu Val Ala Gln Cys Leu Val Cys Val Pro Trp Asp Ala Arg Pro Pro
50                  55                  60                  65 ccc gcc gcc ccc tcc ttc cgc cag gtg tcc tgc ctg aag gag ctg gtg    298
Pro Ala Ala Pro Ser Phe Arg Gln Val Ser Cys Leu Lys Glu Leu Val
                 70                  75                  80 gcc cga gtg ctg cag agg ctg tgc gag cgc ggc gcg aag aac gtg ctg    346
Ala Arg Val Leu Gln Arg Leu Cys Glu Arg Gly Ala Lys Asn Val Leu
             85                  90                  95 gcc ttc ggc ttc gcg ctg ctg gac ggg gcc cgc ggg ggc ccc ccc gag    394
Ala Phe Gly Phe Ala Leu Leu Asp Gly Ala Arg Gly Gly Pro Pro Glu
        100                 105                 110 gcc ttc acc acc agc gtg cgc agc tac ctg ccc aac acg gtg acc gac    442
Ala Phe Thr Thr Ser Val Arg Ser Tyr Leu Pro Asn Thr Val Thr Asp
    115                 120                 125 gca ctg cgg ggg agc ggg gcg tgg ggg ctg ctg ctg cgc cgc gtg ggc    490
Ala Leu Arg Gly Ser Gly Ala Trp Gly Leu Leu Leu Arg Arg Val Gly
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 130 |     |     |     |     | 135 |     |     |     |     | 140 |     |     |     |     | 145 |     |
| gac | gac | gtg | ctg | gtt | cac | ctg | ctg | gca | cgc | tgc | gcg | ctc | ttt | gtg | ctg | 538 |
| Asp | Asp | Val | Leu | Val | His | Leu | Leu | Ala | Arg | Cys | Ala | Leu | Phe | Val | Leu |     |
|     |     |     |     |     | 150 |     |     |     |     | 155 |     |     |     |     | 160 |     |
| gtg | gct | ccc | agc | tgc | gcc | tac | cag | gtg | tgc | ggg | ccg | ccg | ctg | tac | cag | 586 |
| Val | Ala | Pro | Ser | Cys | Ala | Tyr | Gln | Val | Cys | Gly | Pro | Pro | Leu | Tyr | Gln |     |
|     |     |     |     | 165 |     |     |     |     | 170 |     |     |     |     | 175 |     |     |
| ctc | ggc | gct | gcc | act | cag | gcc | cgg | ccc | ccg | cca | cac | gct | agt | gga | ccc | 634 |
| Leu | Gly | Ala | Ala | Thr | Gln | Ala | Arg | Pro | Pro | Pro | His | Ala | Ser | Gly | Pro |     |
|     |     |     | 180 |     |     |     |     | 185 |     |     |     |     | 190 |     |     |     |
| cga | agg | cgt | ctg | gga | tgc | gaa | cgg | gcc | tgg | aac | cat | agc | gtc | agg | gag | 682 |
| Arg | Arg | Arg | Leu | Gly | Cys | Glu | Arg | Ala | Trp | Asn | His | Ser | Val | Arg | Glu |     |
|     |     | 195 |     |     |     |     | 200 |     |     |     |     | 205 |     |     |     |     |
| gcc | ggg | gtc | ccc | ctg | ggc | ctg | cca | gcc | ccg | ggt | gcg | agg | agg | cgc | ggg | 730 |
| Ala | Gly | Val | Pro | Leu | Gly | Leu | Pro | Ala | Pro | Gly | Ala | Arg | Arg | Arg | Gly |     |
| 210 |     |     |     |     | 215 |     |     |     |     | 220 |     |     |     |     | 225 |     |
| ggc | agt | gcc | agc | cga | agt | ctg | ccg | ttg | ccc | aag | agg | ccc | agg | cgt | ggc | 778 |
| Gly | Ser | Ala | Ser | Arg | Ser | Leu | Pro | Leu | Pro | Lys | Arg | Pro | Arg | Arg | Gly |     |
|     |     |     |     | 230 |     |     |     |     | 235 |     |     |     |     | 240 |     |     |
| gct | gcc | cct | gag | ccg | gag | cgg | acg | ccc | gtt | ggg | cag | ggg | tcc | tgg | gcc | 826 |
| Ala | Ala | Pro | Glu | Pro | Glu | Arg | Thr | Pro | Val | Gly | Gln | Gly | Ser | Trp | Ala |     |
|     |     |     |     | 245 |     |     |     |     | 250 |     |     |     |     | 255 |     |     |
| cac | ccg | ggc | agg | acg | cgt | gga | ccg | agt | gac | cgt | ggt | ttc | tgt | gtg | gtg | 874 |
| His | Pro | Gly | Arg | Thr | Arg | Gly | Pro | Ser | Asp | Arg | Gly | Phe | Cys | Val | Val |     |
|     |     | 260 |     |     |     |     | 265 |     |     |     |     | 270 |     |     |     |     |
| tca | cct | gcc | aga | ccc | gcc | gaa | gaa | gcc | acc | tct | ttg | gag | ggt | gcg | ctc | 922 |
| Ser | Pro | Ala | Arg | Pro | Ala | Glu | Glu | Ala | Thr | Ser | Leu | Glu | Gly | Ala | Leu |     |
|     | 275 |     |     |     |     | 280 |     |     |     |     | 285 |     |     |     |     |     |
| tct | ggc | acg | cgc | cac | tcc | cac | cca | tcc | gtg | ggc | cgc | cag | cac | cac | gcg | 970 |
| Ser | Gly | Thr | Arg | His | Ser | His | Pro | Ser | Val | Gly | Arg | Gln | His | His | Ala |     |
| 290 |     |     |     |     | 295 |     |     |     |     | 300 |     |     |     |     | 305 |     |
| ggc | ccc | cca | tcc | aca | tcg | cgg | cca | cca | cgt | ccc | tgg | gac | acg | cct | tgt | 1018 |
| Gly | Pro | Pro | Ser | Thr | Ser | Arg | Pro | Pro | Arg | Pro | Trp | Asp | Thr | Pro | Cys |     |
|     |     |     |     | 310 |     |     |     |     | 315 |     |     |     |     | 320 |     |     |
| ccc | ccg | gtg | tac | gcc | gag | acc | aag | cac | ttc | ctc | tac | tcc | tca | ggc | gac | 1066 |
| Pro | Pro | Val | Tyr | Ala | Glu | Thr | Lys | His | Phe | Leu | Tyr | Ser | Ser | Gly | Asp |     |
|     |     |     | 325 |     |     |     |     | 330 |     |     |     |     | 335 |     |     |     |
| aag | gag | cag | ctg | cgg | ccc | tcc | ttc | cta | ctc | agc | tct | ctg | agg | ccc | agc | 1114 |
| Lys | Glu | Gln | Leu | Arg | Pro | Ser | Phe | Leu | Leu | Ser | Ser | Leu | Arg | Pro | Ser |     |
|     |     | 340 |     |     |     |     | 345 |     |     |     |     | 350 |     |     |     |     |
| ctg | act | ggc | gct | cgg | agg | ctc | gtg | gag | acc | atc | ttt | ctg | ggt | tcc | agg | 1162 |
| Leu | Thr | Gly | Ala | Arg | Arg | Leu | Val | Glu | Thr | Ile | Phe | Leu | Gly | Ser | Arg |     |
|     | 355 |     |     |     |     | 360 |     |     |     |     | 365 |     |     |     |     |     |
| ccc | tgg | atg | cca | ggg | act | ccc | cgc | agg | ttg | ccc | cgc | ctg | ccc | cag | cgc | 1210 |
| Pro | Trp | Met | Pro | Gly | Thr | Pro | Arg | Arg | Leu | Pro | Arg | Leu | Pro | Gln | Arg |     |
| 370 |     |     |     | 375 |     |     |     |     | 380 |     |     |     |     | 385 |     |     |
| tac | tgg | caa | atg | cgg | ccc | ctg | ttt | ctg | gag | ctg | ctt | ggg | aac | cac | gcg | 1258 |
| Tyr | Trp | Gln | Met | Arg | Pro | Leu | Phe | Leu | Glu | Leu | Leu | Gly | Asn | His | Ala |     |
|     |     |     |     | 390 |     |     |     |     | 395 |     |     |     |     | 400 |     |     |
| cag | tgc | ccc | tac | ggg | gtg | ctc | ctc | aag | acg | cac | tgc | ccg | ctg | cga | gct | 1306 |
| Gln | Cys | Pro | Tyr | Gly | Val | Leu | Leu | Lys | Thr | His | Cys | Pro | Leu | Arg | Ala |     |
|     |     |     | 405 |     |     |     |     | 410 |     |     |     |     | 415 |     |     |     |
| gcg | gtc | acc | cca | gca | gcc | ggt | gtc | tgt | gcc | cgg | gag | aag | ccc | cag | ggc | 1354 |
| Ala | Val | Thr | Pro | Ala | Ala | Gly | Val | Cys | Ala | Arg | Glu | Lys | Pro | Gln | Gly |     |
|     |     |     | 420 |     |     |     |     | 425 |     |     |     |     | 430 |     |     |     |
| tct | gtg | gcg | gcc | ccc | gag | gag | gag | gac | aca | gac | ccc | gtc | gcc | ctg | gtg | 1402 |
| Ser | Val | Ala | Ala | Pro | Glu | Glu | Glu | Asp | Thr | Asp | Pro | Arg | Arg | Leu | Val |     |
|     |     | 435 |     |     |     |     | 440 |     |     |     |     | 445 |     |     |     |     |
| cag | ctg | ctc | cgc | cag | cac | agc | agc | ccc | tgg | cag | gtg | tac | ggc | ttc | gtg | 1450 |

|   |   |
|---|---|
| Gln Leu Leu Arg Gln His Ser Ser Pro Trp Gln Val Tyr Gly Phe Val<br>450                       455                     460                   465 |   |
| cgg gcc tgc ctg cgc cgg ctg gtg ccc cca ggc ctc tgg ggc tcc agg<br>Arg Ala Cys Leu Arg Arg Leu Val Pro Pro Gly Leu Trp Gly Ser Arg<br>                    470                     475                   480 | 1498 |
| cac aac gaa cgc cgc ttc ctc agg aac acc aag aag ttc atc tcc ctg<br>His Asn Glu Arg Arg Phe Leu Arg Asn Thr Lys Lys Phe Ile Ser Leu<br>                 485                     490                   495 | 1546 |
| ggg aag cat gcc aag ctc tcg ctg cag gag ctg acg tgg aag atg agc<br>Gly Lys His Ala Lys Leu Ser Leu Gln Glu Leu Thr Trp Lys Met Ser<br>            500                     505                   510 | 1594 |
| gtg cgg gac tgc gct tgg ctg cgc agg agc cca ggg gtt ggc tgt gtt<br>Val Arg Asp Cys Ala Trp Leu Arg Arg Ser Pro Gly Val Gly Cys Val<br>     515                     520                     525 | 1642 |
| ccg gcc gca gag cac cgt ctg cgt gag gag atc ctg gcc aag ttc ctg<br>Pro Ala Ala Glu His Arg Leu Arg Glu Glu Ile Leu Ala Lys Phe Leu<br>530                     535                     540                   545 | 1690 |
| cac tgg ctg atg agt gtg tac gtc gtc gag ctg ctc agg tct ttc ttt<br>His Trp Leu Met Ser Val Tyr Val Val Glu Leu Leu Arg Ser Phe Phe<br>                 550                     555                   560 | 1738 |
| tat gtc acg gag acc acg ttt caa aag aac agg ctc ttt ttc tac cgg<br>Tyr Val Thr Glu Thr Thr Phe Gln Lys Asn Arg Leu Phe Phe Tyr Arg<br>            565                     570                   575 | 1786 |
| aag agt gtc tgg agc aag ttg caa agc att gga atc aga cag cac ttg<br>Lys Ser Val Trp Ser Lys Leu Gln Ser Ile Gly Ile Arg Gln His Leu<br>     580                     585                     590 | 1834 |
| aag agg gtg cag ctg cgg gag ctg tcg gaa gca gag gtc agg cag cat<br>Lys Arg Val Gln Leu Arg Glu Leu Ser Glu Ala Glu Val Arg Gln His<br>595                     600                     605 | 1882 |
| cgg gaa gcc agg ccc gcc ctg ctg acg tcc aga ctc cgc ttc atc ccc<br>Arg Glu Ala Arg Pro Ala Leu Leu Thr Ser Arg Leu Arg Phe Ile Pro<br>610                     615                     620                   625 | 1930 |
| aag cct gac ggg ctg cgg ccg att gtg aac atg gac tac gtc gtg gga<br>Lys Pro Asp Gly Leu Arg Pro Ile Val Asn Met Asp Tyr Val Val Gly<br>            630                     635                   640 | 1978 |
| gcc aga acg ttc cgc aga gaa aag agg gcc gag cgt ctc acc tcg agg<br>Ala Arg Thr Phe Arg Arg Glu Lys Arg Ala Glu Arg Leu Thr Ser Arg<br>                 645                     650                   655 | 2026 |
| gtg aag gca ctg ttc agc gtg ctc aac tac gag cgg gcg cgg cgc ccc<br>Val Lys Ala Leu Phe Ser Val Leu Asn Tyr Glu Arg Ala Arg Arg Pro<br>     660                     665                     670 | 2074 |
| ggc ctc ctg ggc gcc tct gtg ctg ggc ctg gac gat atc cac agg gcc<br>Gly Leu Leu Gly Ala Ser Val Leu Gly Leu Asp Asp Ile His Arg Ala<br>675                     680                     685 | 2122 |
| tgg cgc acc ttc gtg ctg cgt gtg cgg gcc cag gac ccg ccg cct gag<br>Trp Arg Thr Phe Val Leu Arg Val Arg Ala Gln Asp Pro Pro Pro Glu<br>690                     695                     700                   705 | 2170 |
| ctg tac ttt gtc aag gtg gat gtg acg ggc gcg tac gac acc atc ccc<br>Leu Tyr Phe Val Lys Val Asp Val Thr Gly Ala Tyr Asp Thr Ile Pro<br>                 710                     715                   720 | 2218 |
| cag gac agg ctc acg gag gtc atc gcc agc atc atc aaa ccc cag aac<br>Gln Asp Arg Leu Thr Glu Val Ile Ala Ser Ile Ile Lys Pro Gln Asn<br>            725                     730                   735 | 2266 |
| acg tac tgc gtg cgt cgg tat gcc gtg gtc cag aag gcc gcc cat ggg<br>Thr Tyr Cys Val Arg Arg Tyr Ala Val Val Gln Lys Ala Ala His Gly<br>     740                     745                     750 | 2314 |
| cac gtc cgc aag gcc ttc aag agc cac gtc tct acc ttg aca gac ctc<br>His Val Arg Lys Ala Phe Lys Ser His Val Ser Thr Leu Thr Asp Leu<br>755                     760                     765 | 2362 |

-continued

| | | |
|---|---|---|
| cag ccg tac atg cga cag ttc gtg gct cac ctg cag gag acc agc ccg<br>Gln Pro Tyr Met Arg Gln Phe Val Ala His Leu Gln Glu Thr Ser Pro<br>770                775                  780              785 | 2410 | |
| ctg agg gat gcc gtc gtc atc gag cag agc tcc tcc ctg aat gag gcc<br>Leu Arg Asp Ala Val Val Ile Glu Gln Ser Ser Ser Leu Asn Glu Ala<br>                  790                  795                800 | 2458 | |
| agc agt ggc ctc ttc gac gtc ttc cta cgc ttc atg tgc cac cac gcc<br>Ser Ser Gly Leu Phe Asp Val Phe Leu Arg Phe Met Cys His His Ala<br>              805                  810                815 | 2506 | |
| gtg cgc atc agg ggc aag tcc tac gtc cag tgc cag ggg atc ccg cag<br>Val Arg Ile Arg Gly Lys Ser Tyr Val Gln Cys Gln Gly Ile Pro Gln<br>820                825                  830 | 2554 | |
| ggc tcc atc ctc tcc acg ctc ctc tgc agc ctg tgc tac ggc gac atg<br>Gly Ser Ile Leu Ser Thr Leu Leu Cys Ser Leu Cys Tyr Gly Asp Met<br>              835                  840                845 | 2602 | |
| gag aac aag ctg ttt gcg ggg att cgg cgg gac ggg ctg ctc ctg cgt<br>Glu Asn Lys Leu Phe Ala Gly Ile Arg Arg Asp Gly Leu Leu Leu Arg<br>850                855                  860                865 | 2650 | |
| ttg gtg gat gat ttc ttg ttg gtg aca cct cac ctc acc cac gcg aaa<br>Leu Val Asp Asp Phe Leu Leu Val Thr Pro His Leu Thr His Ala Lys<br>                  870                  875                880 | 2698 | |
| acc ttc ctc agg acc ctg gtc cga ggt gtc cct gag tat ggc tgc gtg<br>Thr Phe Leu Arg Thr Leu Val Arg Gly Val Pro Glu Tyr Gly Cys Val<br>              885                  890                895 | 2746 | |
| gtg aac ttg cgg aag aca gtg gtg aac ttc cct gta gaa gac gag gcc<br>Val Asn Leu Arg Lys Thr Val Val Asn Phe Pro Val Glu Asp Glu Ala<br>900                905                  910 | 2794 | |
| ctg ggt ggc acg gct ttt gtt cag atg ccg gcc cac ggc cta ttc ccc<br>Leu Gly Gly Thr Ala Phe Val Gln Met Pro Ala His Gly Leu Phe Pro<br>              915                  920                925 | 2842 | |
| tgg tgc ggc ctg ctg ctg gat acc cgg acc ctg gag gtg cag agc gac<br>Trp Cys Gly Leu Leu Leu Asp Thr Arg Thr Leu Glu Val Gln Ser Asp<br>930                935                  940                945 | 2890 | |
| tac tcc agc tat gcc cgg acc tcc atc aga gcc agt ctc acc ttc aac<br>Tyr Ser Ser Tyr Ala Arg Thr Ser Ile Arg Ala Ser Leu Thr Phe Asn<br>              950                  955                960 | 2938 | |
| cgc ggc ttc aag gct ggg agg aac atg cgt cgc aaa ctc ttt ggg gtc<br>Arg Gly Phe Lys Ala Gly Arg Asn Met Arg Arg Lys Leu Phe Gly Val<br>              965                  970                975 | 2986 | |
| ttg cgg ctg aag tgt cac agc ctg ttt ctg gat ttg cag gtg aac agc<br>Leu Arg Leu Lys Cys His Ser Leu Phe Leu Asp Leu Gln Val Asn Ser<br>                  980                  985                990 | 3034 | |
| ctc cag acg gtg tgc acc aac  atc tac aag atc ctc  ctg ctg cag gcg<br>Leu Gln Thr Val Cys Thr Asn Ile Tyr Lys Ile Leu Leu Leu Gln Ala<br>              995                  1000              1005 | 3082 | |
| tac  agg ttt cac gca tgt  gtg ctg cag ctc cca  ttt cat cag caa<br>Tyr Arg Phe His Ala Cys Val Leu Gln Leu Pro Phe His Gln Gln<br>1010                1015                1020 | 3127 | |
| gtt  tgg aag aac ccc aca  ttt ttc ctg cgc gtc  atc tct gac acg<br>Val Trp Lys Asn Pro Thr Phe Phe Leu Arg Val Ile Ser Asp Thr<br>1025                1030                1035 | 3172 | |
| gcc  tcc ctc tgc tac tcc  atc ctg aaa gcc aag  aac gca ggg atg<br>Ala Ser Leu Cys Tyr Ser Ile Leu Lys Ala Lys Asn Ala Gly Met<br>1040                1045                1050 | 3217 | |
| tcg  ctg ggg gcc aag ggc  gcc gcc ggc cct ctg  ccc tcc gag gcc<br>Ser Leu Gly Ala Lys Gly Ala Ala Gly Pro Leu Pro Ser Glu Ala<br>1055                1060                1065 | 3262 | |
| gtg  cag tgg ctg tgc cac  caa gca ttc ctg ctc  aag ctg act cga<br>Val Gln Trp Leu Cys His Gln Ala Phe Leu Leu Lys Leu Thr Arg<br>1070                1075                1080 | 3307 | |

```
cac cgt gtc acc tac gtg cca ctc ctg ggg tca ctc agg aca gcc      3352
His Arg Val Thr Tyr Val Pro Leu Leu Gly Ser Leu Arg Thr Ala
1085                1090                1095 cag acg cag ctg agt cgg aag ctc ccg ggg acg acg ctg act gcc      3397
Gln Thr Gln Leu Ser Arg Lys Leu Pro Gly Thr Thr Leu Thr Ala
1100                1105                1110 ctg gag gcc gca gcc aac ccg gca ctg ccc tca gac ttc aag acc      3442
Leu Glu Ala Ala Ala Asn Pro Ala Leu Pro Ser Asp Phe Lys Thr
1115                1120                1125 atc ctg gac tga tggccacccg cccacagcca ggccgagagc agacaccagc      3494
Ile Leu Asp
1130 agccctgtca cgccgggctc tacgtcccag ggagggaggg gcggcccaca cccaggcccg   3554 caccgctggg agtctgaggc ctgagtgagt gtttggccga ggcctgcatg tccggctgaa   3614 ggctgagtgt ccggctgagg cctgagcgag tgtccagcca agggctgagt gtccagcaca   3674 cctgccgtct tcacttcccc acaggctggc gctcggctcc accccagggc cagcttttcc   3734 tcaccaggag cccggcttcc actccccaca taggaatagt ccatcccag attcgccatt    3794 gttcacccct cgccctgccc tcctttgcct tccacccca ccatccaggt ggagaccctg    3854 agaaggaccc tgggagctct gggaatttgg agtgaccaaa ggtgtgccct gtacacaggc   3914 gaggaccctg cacctggatg ggggtccctg tgggtcaaat tgggggagg tgctgtggga    3974 gtaaaatact gaatatatga gttttcagt tttgaaaaaa a                        4015
```

<210> SEQ ID NO 37
<211> LENGTH: 1132
<212> TYPE: PRT
<213> ORGANISM: Homo sapiens

<400> SEQUENCE: 37

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190
```

-continued

```
Pro Arg Arg Arg Leu Gly Cys Glu Arg Ala Trp Asn His Ser Val Arg
            195                 200                 205
Glu Ala Gly Val Pro Leu Gly Leu Pro Ala Pro Gly Ala Arg Arg Arg
210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
            245                 250                 255
Ala His Pro Gly Arg Thr Arg Gly Pro Ser Asp Arg Gly Phe Cys Val
            260                 265                 270
Val Ser Pro Ala Arg Pro Ala Glu Glu Ala Thr Ser Leu Glu Gly Ala
            275                 280                 285
Leu Ser Gly Thr Arg His Ser His Pro Ser Val Gly Arg Gln His His
            290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
            325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
            355                 360                 365
Arg Pro Trp Met Pro Gly Thr Pro Arg Arg Leu Pro Arg Leu Pro Gln
            370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
            405                 410                 415
Ala Ala Val Thr Pro Ala Ala Gly Val Cys Ala Arg Glu Lys Pro Gln
            420                 425                 430
Gly Ser Val Ala Ala Pro Glu Glu Glu Asp Thr Asp Pro Arg Arg Leu
            435                 440                 445
Val Gln Leu Leu Arg Gln His Ser Ser Pro Trp Gln Val Tyr Gly Phe
450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
            485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
            515                 520                 525
Val Pro Ala Ala Glu His Arg Leu Arg Glu Glu Ile Leu Ala Lys Phe
            530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
            565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
            595                 600                 605
His Arg Glu Ala Arg Pro Ala Leu Leu Thr Ser Arg Leu Arg Phe Ile
```

-continued

```
            610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                    645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro
        690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
        770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
        850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
        930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035
```

```
Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 38
<211> LENGTH: 4009
<212> TYPE: DNA
<213> ORGANISM: Artificial
<220> FEATURE:
<223> OTHER INFORMATION: Gene encoding a non-functional deleted form of
      HTERT (amino acid residues 867 to 869)
<220> FEATURE:
<221> NAME/KEY: CDS
<222> LOCATION: (59)..(3448)

<400> SEQUENCE: 38
caggcagcgc tgcgtcctgc tgcgcacgtg ggaagccctg gccccggcca ccccgcg          58 atg ccg cgc gct ccc cgc tgc cga gcc gtg cgc tcc ctg ctg cgc agc      106
Met Pro Arg Ala Pro Arg Cys Arg Ala Val Arg Ser Leu Leu Arg Ser
1               5                   10                  15 cac tac cgc gag gtg ctg ccg ctg gcc acg ttc gtg cgg cgc ctg ggg      154
His Tyr Arg Glu Val Leu Pro Leu Ala Thr Phe Val Arg Arg Leu Gly
            20                  25                  30 ccc cag ggc tgg cgg ctg gtg cag cgc ggg gac ccg gcg gct ttc cgc      202
Pro Gln Gly Trp Arg Leu Val Gln Arg Gly Asp Pro Ala Ala Phe Arg
        35                  40                  45 gcg ctg gtg gcc cag tgc ctg gtg tgc gtg ccc tgg gac gca cgg ccg      250
Ala Leu Val Ala Gln Cys Leu Val Cys Val Pro Trp Asp Ala Arg Pro
    50                  55                  60 ccc ccc gcc gcc ccc tcc ttc cgc cag gtg tcc tgc ctg aag gag ctg      298
Pro Pro Ala Ala Pro Ser Phe Arg Gln Val Ser Cys Leu Lys Glu Leu
65                  70                  75                  80 gtg gcc cga gtg ctg cag agg ctg tgc gag cgc ggc gcg aag aac gtg      346
Val Ala Arg Val Leu Gln Arg Leu Cys Glu Arg Gly Ala Lys Asn Val
                85                  90                  95 ctg gcc ttc ggc ttc gcg ctg ctg gac ggg gcc cgc ggg ggc ccc ccc      394
Leu Ala Phe Gly Phe Ala Leu Leu Asp Gly Ala Arg Gly Gly Pro Pro
            100                 105                 110 gag gcc ttc acc acc agc gtg cgc agc tac ctg ccc aac acg gtg acc      442
Glu Ala Phe Thr Thr Ser Val Arg Ser Tyr Leu Pro Asn Thr Val Thr
        115                 120                 125 gac gca ctg cgg ggg agc ggg gcg tgg ggg ctg ctg cgc cgc gtg            490
Asp Ala Leu Arg Gly Ser Gly Ala Trp Gly Leu Leu Arg Arg Val
    130                 135                 140 ggc gac gac gtg ctg gtt cac ctg ctg gca cgc tgc gcg ctc ttt gtg      538
Gly Asp Asp Val Leu Val His Leu Leu Ala Arg Cys Ala Leu Phe Val
145                 150                 155                 160 ctg gtg gct ccc agc tgc gcc tac cag gtg tgc ggg ccg ccg ctg tac      586
```

```
                                                                    -continued Leu Val Ala Pro Ser Cys Ala Tyr Gln Val Cys Gly Pro Pro Leu Tyr
            165                 170                 175 cag ctc ggc gct gcc act cag gcc cgg ccc ccg cca cac gct agt gga       634
Gln Leu Gly Ala Ala Thr Gln Ala Arg Pro Pro Pro His Ala Ser Gly
            180                 185                 190 ccc cga agg cgt ctg gga tgc gaa cgg gcc tgg aac cat agc gtc agg       682
Pro Arg Arg Arg Leu Gly Cys Glu Arg Ala Trp Asn His Ser Val Arg
            195                 200                 205 gag gcc ggg gtc ccc ctg ggc ctg cca gcc ccg ggt gcg agg agg cgc       730
Glu Ala Gly Val Pro Leu Gly Leu Pro Ala Pro Gly Ala Arg Arg Arg
    210                 215                 220 ggg ggc agt gcc agc cga agt ctg ccg ttg ccc aag agg ccc agg cgt       778
Gly Gly Ser Ala Ser Arg Ser Leu Pro Leu Pro Lys Arg Pro Arg Arg
225                 230                 235                 240 ggc gct gcc cct gag ccg gag cgg acg ccc gtt ggg cag ggg tcc tgg       826
Gly Ala Ala Pro Glu Pro Glu Arg Thr Pro Val Gly Gln Gly Ser Trp
                245                 250                 255 gcc cac ccg ggc agg acg cgt gga ccg agt gac cgt ggt ttc tgt gtg       874
Ala His Pro Gly Arg Thr Arg Gly Pro Ser Asp Arg Gly Phe Cys Val
            260                 265                 270 gtg tca cct gcc aga ccc gcc gaa gaa gcc acc tct ttg gag ggt gcg       922
Val Ser Pro Ala Arg Pro Ala Glu Glu Ala Thr Ser Leu Glu Gly Ala
        275                 280                 285 ctc tct ggc acg cgc cac tcc cac cca tcc gtg ggc cgc cag cac cac       970
Leu Ser Gly Thr Arg His Ser His Pro Ser Val Gly Arg Gln His His
    290                 295                 300 gcg ggc ccc cca tcc aca tcg cgg cca cca cgt ccc tgg gac acg cct      1018
Ala Gly Pro Pro Ser Thr Ser Arg Pro Pro Arg Pro Trp Asp Thr Pro
305                 310                 315                 320 tgt ccc ccg gtg tac gcc gag acc aag cac ttc ctc tac tcc tca ggc      1066
Cys Pro Pro Val Tyr Ala Glu Thr Lys His Phe Leu Tyr Ser Ser Gly
                325                 330                 335 gac aag gag cag ctg cgg ccc tcc ttc cta ctc agc tct ctg agg ccc      1114
Asp Lys Glu Gln Leu Arg Pro Ser Phe Leu Leu Ser Ser Leu Arg Pro
            340                 345                 350 agc ctg act ggc gct cgg agg ctc gtg gag acc atc ttt ctg ggt tcc      1162
Ser Leu Thr Gly Ala Arg Arg Leu Val Glu Thr Ile Phe Leu Gly Ser
        355                 360                 365 agg ccc tgg atg cca ggg act ccc cgc agg ttg ccc cgc ctg ccc cag      1210
Arg Pro Trp Met Pro Gly Thr Pro Arg Arg Leu Pro Arg Leu Pro Gln
    370                 375                 380 cgc tac tgg caa atg cgg ccc ctg ttt ctg gag ctg ctt ggg aac cac      1258
Arg Tyr Trp Gln Met Arg Pro Leu Phe Leu Glu Leu Leu Gly Asn His
385                 390                 395                 400 gcg cag tgc ccc tac ggg gtg ctc ctc aag acg cac tgc ccg ctg cga      1306
Ala Gln Cys Pro Tyr Gly Val Leu Leu Lys Thr His Cys Pro Leu Arg
                405                 410                 415 gct gcg gtc acc cca gca gcc ggt gtc tgt gcc cgg gag aag ccc cag      1354
Ala Ala Val Thr Pro Ala Ala Gly Val Cys Ala Arg Glu Lys Pro Gln
            420                 425                 430 ggc tct gtg gcg gcc ccc gag gag gag gac aca gac ccc gtc gcc ctg      1402
Gly Ser Val Ala Ala Pro Glu Glu Glu Asp Thr Asp Pro Arg Arg Leu
        435                 440                 445 gtg cag ctg ctc cgc cag cac agc agc ccc tgg cag gtg tac ggc ttc      1450
Val Gln Leu Leu Arg Gln His Ser Ser Pro Trp Gln Val Tyr Gly Phe
    450                 455                 460 gtg cgg gcc tgc ctg cgc cgg ctg gtg ccc cca ggc ctc tgg ggc tcc      1498
Val Arg Ala Cys Leu Arg Arg Leu Val Pro Pro Gly Leu Trp Gly Ser
465                 470                 475                 480
```

```
agg cac aac gaa cgc cgc ttc ctc agg aac acc aag aag ttc atc tcc     1546
Arg His Asn Glu Arg Arg Phe Leu Arg Asn Thr Lys Lys Phe Ile Ser
                485                 490                 495 ctg ggg aag cat gcc aag ctc tcg ctg cag gag ctg acg tgg aag atg     1594
Leu Gly Lys His Ala Lys Leu Ser Leu Gln Glu Leu Thr Trp Lys Met
            500                 505                 510 agc gtg cgg gac tgc gct tgg ctg cgc agg agc cca ggg gtt ggc tgt     1642
Ser Val Arg Asp Cys Ala Trp Leu Arg Arg Ser Pro Gly Val Gly Cys
        515                 520                 525 gtt ccg gcc gca gag cac cgt ctc cgt gag gag atc ctg gcc aag ttc     1690
Val Pro Ala Ala Glu His Arg Leu Arg Glu Glu Ile Leu Ala Lys Phe
    530                 535                 540 ctg cac tgg ctg atg agt gtg tac gtc gtc gag ctg ctc agg tct ttc     1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac     1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac     1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag     1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc     1930
His Arg Glu Ala Arg Pro Ala Leu Leu Thr Ser Arg Leu Arg Phe Ile
    610                 615                 620 ccc aag cct gac ggg ctg cgg ccg att gtg aac atg gac tac gtc gtg     1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg     2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc     2074
Arg Val Lys Ala Leu Phe Ser Val Leu Asn Tyr Glu Arg Ala Arg Arg
            660                 665                 670 ccc ggc ctc ctg ggc gcc tct gtg ctg ggc ctg gac gat atc cac agg     2122
Pro Gly Leu Leu Gly Ala Ser Val Leu Gly Leu Asp Asp Ile His Arg
        675                 680                 685 gcc tgg cgc acc ttc gtg ctg cgt gtg cgg gcc cag gac ccg ccg cct     2170
Ala Trp Arg Thr Phe Val Leu Arg Val Arg Ala Gln Asp Pro Pro Pro
    690                 695                 700 gag ctg tac ttt gtc aag gtg gat gtg acg ggc gcg tac gac acc atc     2218
Glu Leu Tyr Phe Val Lys Val Asp Val Thr Gly Ala Tyr Asp Thr Ile
705                 710                 715                 720 ccc cag gac agg ctc acg gag gtc atc gcc agc atc atc aaa ccc cag     2266
Pro Gln Asp Arg Leu Thr Glu Val Ile Ala Ser Ile Ile Lys Pro Gln
                725                 730                 735 aac acg tac tgc gtg cgt cgg tat gcc gtg gtc cag aag gcc gcc cat     2314
Asn Thr Tyr Cys Val Arg Arg Tyr Ala Val Val Gln Lys Ala Ala His
            740                 745                 750 ggg cac gtc cgc aag gcc ttc aag agc cac gtc tct acc ttg aca gac     2362
Gly His Val Arg Lys Ala Phe Lys Ser His Val Ser Thr Leu Thr Asp
        755                 760                 765 ctc cag ccg tac atg cga cag ttc gtg gct cac ctg cag gag acc agc     2410
Leu Gln Pro Tyr Met Arg Gln Phe Val Ala His Leu Gln Glu Thr Ser
    770                 775                 780 ccg ctg agg gat gcc gtc gtc atc gag cag agc tcc tcc ctg aat gag     2458
Pro Leu Arg Asp Ala Val Val Ile Glu Gln Ser Ser Ser Leu Asn Glu
785                 790                 795                 800
```

```
gcc agc agt ggc ctc ttc gac gtc ttc cta cgc ttc atg tgc cac cac        2506
Ala Ser Ser Gly Leu Phe Asp Val Phe Leu Arg Phe Met Cys His His
                805             810             815 gcc gtg cgc atc agg ggc aag tcc tac gtc cag tgc cag ggg atc ccg        2554
Ala Val Arg Ile Arg Gly Lys Ser Tyr Val Gln Cys Gln Gly Ile Pro
            820             825             830 cag ggc tcc atc ctc tcc acg ctg ctc tgc agc ctg tgc tac ggc gac        2602
Gln Gly Ser Ile Leu Ser Thr Leu Leu Cys Ser Leu Cys Tyr Gly Asp
        835             840             845 atg gag aac aag ctg ttt gcg ggg att cgg cgg gac ggg ctg ctc ctg        2650
Met Glu Asn Lys Leu Phe Ala Gly Ile Arg Arg Asp Gly Leu Leu Leu
    850             855             860 cgt ttg ttc ttg ttg gtg aca cct cac ctc acc cac gcg aaa acc ttc        2698
Arg Leu Phe Leu Leu Val Thr Pro His Leu Thr His Ala Lys Thr Phe
865             870             875             880 ctc agg acc ctg gtc cga ggt gtc cct gag tat ggc tgc gtg gtg aac        2746
Leu Arg Thr Leu Val Arg Gly Val Pro Glu Tyr Gly Cys Val Val Asn
                885             890             895 ttg cgg aag aca gtg gtg aac ttc cct gta gaa gac gag gcc ctg ggt        2794
Leu Arg Lys Thr Val Val Asn Phe Pro Val Glu Asp Glu Ala Leu Gly
            900             905             910 ggc acg gct ttt gtt cag atg ccg gcc cac ggc cta ttc ccc tgg tgc        2842
Gly Thr Ala Phe Val Gln Met Pro Ala His Gly Leu Phe Pro Trp Cys
        915             920             925 ggc ctg ctg ctg gat acc cgg acc ctg gag gtg cag agc gac tac tcc        2890
Gly Leu Leu Leu Asp Thr Arg Thr Leu Glu Val Gln Ser Asp Tyr Ser
    930             935             940 agc tat gcc cgg acc tcc atc aga gcc agt ctc acc ttc aac cgc ggc        2938
Ser Tyr Ala Arg Thr Ser Ile Arg Ala Ser Leu Thr Phe Asn Arg Gly
945             950             955             960 ttc aag gct ggg agg aac atg cgt cgc aaa ctc ttt ggg gtc ttg cgg        2986
Phe Lys Ala Gly Arg Asn Met Arg Arg Lys Leu Phe Gly Val Leu Arg
                965             970             975 ctg aag tgt cac agc ctg ttt ctg gat ttg cag gtg aac agc ctc cag        3034
Leu Lys Cys His Ser Leu Phe Leu Asp Leu Gln Val Asn Ser Leu Gln
            980             985             990 acg gtg tgc acc aac atc tac aag  atc ctc ctg ctg cag  gcg tac agg      3082
Thr Val Cys Thr Asn Ile Tyr Lys  Ile Leu Leu Leu Gln  Ala Tyr Arg
        995             1000            1005 ttt cac  gca tgt gtg ctg cag  ctc cca ttt cat cag  caa gtt tgg         3127
Phe His  Ala Cys Val Leu Gln  Leu Pro Phe His Gln  Gln Val Trp
1010             1015            1020 aag aac ccc aca ttt ttc ctg  cgc gtc atc tct gac  acg gcc tcc          3172
Lys Asn Pro Thr Phe Phe Leu  Arg Val Ile Ser Asp  Thr Ala Ser
1025             1030            1035 ctc tgc tac tcc atc ctg aaa  gcc aag aac gca ggg  atg tcg ctg          3217
Leu Cys Tyr Ser Ile Leu Lys  Ala Lys Asn Ala Gly  Met Ser Leu
1040             1045            1050 ggg gcc aag ggc gcc gcc ggc  cct ctg ccc tcc gag  gcc gtg cag          3262
Gly Ala Lys Gly Ala Ala Gly  Pro Leu Pro Ser Glu  Ala Val Gln
1055             1060            1065 tgg ctg tgc cac caa gca ttc  ctg ctc aag ctg act  cga cac cgt          3307
Trp Leu Cys His Gln Ala Phe  Leu Leu Lys Leu Thr  Arg His Arg
1070             1075            1080 gtc acc tac gtg cca ctc ctg  ggg tca ctc agg aca  gcc cag acg          3352
Val Thr Tyr Val Pro Leu Leu  Gly Ser Leu Arg Thr  Ala Gln Thr
1085             1090            1095 cag ctg agt cgg aag ctc ccg  ggg acg acg ctg act  gcc ctg gag          3397
Gln Leu Ser Arg Lys Leu Pro  Gly Thr Thr Leu Thr  Ala Leu Glu
```

-continued

```
                  1100               1105               1110
gcc gca gcc aac ccg gca ctg ccc tca gac ttc aag acc atc ctg      3442
Ala Ala Ala Asn Pro Ala Leu Pro Ser Asp Phe Lys Thr Ile Leu
    1115               1120               1125 gac tga tggccacccg cccacagcca ggccgagagc agacaccagc agccctgtca   3498
Asp cgccgggctc tacgtcccag ggagggaggg gcggcccaca cccaggcccg caccgctggg 3558 agtctgaggc ctgagtgagt gtttggccga ggcctgcatg tccggctgaa ggctgagtgt 3618 ccggctgagg cctgagcgag tgtccagcca agggctgagt gtccagcaca cctgccgtct 3678 tcacttcccc acaggctggc gctcggctcc accccagggc cagcttttcc tcaccaggag 3738 cccggcttcc actccccaca taggaatagt ccatcccag attcgccatt gttcacccct   3798
cgccctgccc tcctttgcct tccaccccca ccatccaggt ggagaccctg agaaggaccc 3858 tgggagctct gggaatttgg agtgaccaaa ggtgtgccct gtacacaggc gaggaccctg 3918 cacctggatg gggtccctg tgggtcaaat tggggggagg tgctgtggga gtaaaatact 3978 gaatatatga gtttttcagt tttgaaaaaa a                              4009
```

<210> SEQ ID NO 39
<211> LENGTH: 1129
<212> TYPE: PRT
<213> ORGANISM: Artificial
<220> FEATURE:
<223> OTHER INFORMATION: Synthetic Construct

<400> SEQUENCE: 39

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220
```

```
Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
            245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
```

```
            645                 650                 655
Arg Val Lys Ala Leu Phe Ser Val Leu Asn Tyr Glu Arg Ala Arg Arg
            660                 665                 670
Pro Gly Leu Leu Gly Ala Ser Val Gly Leu Asp Asp Ile His Arg
            675                 680                 685
Ala Trp Arg Thr Phe Val Leu Arg Val Arg Ala Gln Asp Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
            725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
            755                 760                 765
Leu Gln Pro Tyr Met Arg Gln Phe Val Ala His Leu Gln Glu Thr Ser
    770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
            805                 810                 815
Ala Val Arg Ile Arg Gly Lys Ser Tyr Val Gln Cys Gln Gly Ile Pro
            820                 825                 830
Gln Gly Ser Ile Leu Ser Thr Leu Leu Cys Ser Leu Cys Tyr Gly Asp
            835                 840                 845
Met Glu Asn Lys Leu Phe Ala Gly Ile Arg Arg Asp Gly Leu Leu Leu
850                 855                 860
Arg Leu Phe Leu Leu Val Thr Pro His Leu Thr His Ala Lys Thr Phe
865                 870                 875                 880
Leu Arg Thr Leu Val Arg Gly Val Pro Glu Tyr Gly Cys Val Val Asn
            885                 890                 895
Leu Arg Lys Thr Val Val Asn Phe Pro Val Glu Asp Glu Ala Leu Gly
            900                 905                 910
Gly Thr Ala Phe Val Gln Met Pro Ala His Gly Leu Phe Pro Trp Cys
            915                 920                 925
Gly Leu Leu Leu Asp Thr Arg Thr Leu Glu Val Gln Ser Asp Tyr Ser
    930                 935                 940
Ser Tyr Ala Arg Thr Ser Ile Arg Ala Ser Leu Thr Phe Asn Arg Gly
945                 950                 955                 960
Phe Lys Ala Gly Arg Asn Met Arg Arg Lys Leu Phe Gly Val Leu Arg
            965                 970                 975
Leu Lys Cys His Ser Leu Phe Leu Asp Leu Gln Val Asn Ser Leu Gln
            980                 985                 990
Thr Val Cys Thr Asn Ile Tyr Lys Ile Leu Leu Leu Gln Ala Tyr Arg
    995                 1000                1005
Phe His Ala Cys Val Leu Gln Leu Pro Phe His Gln Gln Val Trp
    1010                1015                1020
Lys Asn Pro Thr Phe Phe Leu Arg Val Ile Ser Asp Thr Ala Ser
    1025                1030                1035
Leu Cys Tyr Ser Ile Leu Lys Ala Lys Asn Ala Gly Met Ser Leu
    1040                1045                1050
Gly Ala Lys Gly Ala Ala Gly Pro Leu Pro Ser Glu Ala Val Gln
    1055                1060                1065
```

```
Trp Leu Cys His Gln Ala Phe Leu Leu Lys Leu Thr Arg His Arg
    1070            1075                1080

Val Thr Tyr Val Pro Leu Leu Gly Ser Leu Arg Thr Ala Gln Thr
    1085            1090                1095

Gln Leu Ser Arg Lys Leu Pro Gly Thr Thr Leu Thr Ala Leu Glu
    1100            1105                1110

Ala Ala Ala Asn Pro Ala Leu Pro Ser Asp Phe Lys Thr Ile Leu
    1115            1120                1125

Asp

<210> SEQ ID NO 40
<211> LENGTH: 3991
<212> TYPE: DNA
<213> ORGANISM: Artificial
<220> FEATURE:
<223> OTHER INFORMATION: Gene encoding a non-functional deleted form of
      HTERT (amino acid residues 864 to 872)
<220> FEATURE:
<221> NAME/KEY: CDS
<222> LOCATION: (59)..(3430)

<400> SEQUENCE: 40
caggcagcgc tgcgtcctgc tgcgcacgtg ggaagccctg gccccggcca ccccgcg        58 atg ccg cgc gct ccc cgc tgc cga gcc gtg cgc tcc ctg ctg cgc agc     106
Met Pro Arg Ala Pro Arg Cys Arg Ala Val Arg Ser Leu Leu Arg Ser
1               5                   10                  15 cac tac cgc gag gtg ctg ccg ctg gcc acg ttc gtg cgg cgc ctg ggg     154
His Tyr Arg Glu Val Leu Pro Leu Ala Thr Phe Val Arg Arg Leu Gly
                20                  25                  30 ccc cag ggc tgg cgg ctg gtg cag cgc ggg gac ccg gcg gct ttc cgc     202
Pro Gln Gly Trp Arg Leu Val Gln Arg Gly Asp Pro Ala Ala Phe Arg
            35                  40                  45 gcg ctg gtg gcc cag tgc ctg gtg tgc gtg ccc tgg gac gca cgg ccg     250
Ala Leu Val Ala Gln Cys Leu Val Cys Val Pro Trp Asp Ala Arg Pro
        50                  55                  60 ccc ccc gcc gcc ccc tcc ttc cgc cag gtg tcc tgc ctg aag gag ctg     298
Pro Pro Ala Ala Pro Ser Phe Arg Gln Val Ser Cys Leu Lys Glu Leu
65                  70                  75                  80 gtg gcc cga gtg ctg cag agg ctg tgc gag cgc ggc gcg aag aac gtg     346
Val Ala Arg Val Leu Gln Arg Leu Cys Glu Arg Gly Ala Lys Asn Val
                85                  90                  95 ctg gcc ttc ggc ttc gcg ctg ctg gac ggg gcc cgc ggg ggc ccc ccc     394
Leu Ala Phe Gly Phe Ala Leu Leu Asp Gly Ala Arg Gly Gly Pro Pro
                100                 105                 110 gag gcc ttc acc acc agc gtg cgc agc tac ctg ccc aac acg gtg acc     442
Glu Ala Phe Thr Thr Ser Val Arg Ser Tyr Leu Pro Asn Thr Val Thr
            115                 120                 125 gac gca ctg cgg ggg agc ggg gcg tgg ggg ctg ctg ctg cgc cgc gtg     490
Asp Ala Leu Arg Gly Ser Gly Ala Trp Gly Leu Leu Leu Arg Arg Val
        130                 135                 140 ggc gac gac gtg ctg gtt cac ctg ctg gca cgc tgc gcg ctc ttt gtg     538
Gly Asp Asp Val Leu Val His Leu Leu Ala Arg Cys Ala Leu Phe Val
145                 150                 155                 160 ctg gtg gct ccc agc tgc gcc tac cag gtg tgc ggg ccg ccg ctg tac     586
Leu Val Ala Pro Ser Cys Ala Tyr Gln Val Cys Gly Pro Pro Leu Tyr
                165                 170                 175 cag ctc ggc gct gcc act cag gcc cgg ccc ccg cca cac gct agt gga     634
Gln Leu Gly Ala Ala Thr Gln Ala Arg Pro Pro His Ala Ser Gly
                180                 185                 190
```

| | | |
|---|---|---|
| ccc cga agg cgt ctg gga tgc gaa cgg gcc tgg aac cat agc gtc agg<br>Pro Arg Arg Arg Leu Gly Cys Glu Arg Ala Trp Asn His Ser Val Arg<br>195 200 205 | | 682 |
| gag gcc ggg gtc ccc ctg ggc ctg cca gcc ccg ggt gcg agg agg cgc<br>Glu Ala Gly Val Pro Leu Gly Leu Pro Ala Pro Gly Ala Arg Arg Arg<br>210 215 220 | | 730 |
| ggg ggc agt gcc agc cga agt ctg ccg ttg ccc aag agg ccc agg cgt<br>Gly Gly Ser Ala Ser Arg Ser Leu Pro Leu Pro Lys Arg Pro Arg Arg<br>225 230 235 240 | | 778 |
| ggc gct gcc cct gag ccg gag cgg acg ccc gtt ggg cag ggg tcc tgg<br>Gly Ala Ala Pro Glu Pro Glu Arg Thr Pro Val Gly Gln Gly Ser Trp<br>245 250 255 | | 826 |
| gcc cac ccg ggc agg acg cgt gga ccg agt gac cgt ggt ttc tgt gtg<br>Ala His Pro Gly Arg Thr Arg Gly Pro Ser Asp Arg Gly Phe Cys Val<br>260 265 270 | | 874 |
| gtg tca cct gcc aga ccc gcc gaa gaa gcc acc tct ttg gag ggt gcg<br>Val Ser Pro Ala Arg Pro Ala Glu Glu Ala Thr Ser Leu Glu Gly Ala<br>275 280 285 | | 922 |
| ctc tct ggc acg cgc cac tcc cac cca tcc gtg ggc cgc cag cac cac<br>Leu Ser Gly Thr Arg His Ser His Pro Ser Val Gly Arg Gln His His<br>290 295 300 | | 970 |
| gcg ggc ccc cca tcc aca tcg cgg cca cca cgt ccc tgg gac acg cct<br>Ala Gly Pro Pro Ser Thr Ser Arg Pro Pro Arg Pro Trp Asp Thr Pro<br>305 310 315 320 | | 1018 |
| tgt ccc ccg gtg tac gcc gag acc aag cac ttc ctc tac tcc tca ggc<br>Cys Pro Pro Val Tyr Ala Glu Thr Lys His Phe Leu Tyr Ser Ser Gly<br>325 330 335 | | 1066 |
| gac aag gag cag ctg cgg ccc tcc ttc cta ctc agc tct ctg agg ccc<br>Asp Lys Glu Gln Leu Arg Pro Ser Phe Leu Leu Ser Ser Leu Arg Pro<br>340 345 350 | | 1114 |
| agc ctg act ggc gct cgg agg ctc gtg gag acc atc ttt ctg ggt tcc<br>Ser Leu Thr Gly Ala Arg Arg Leu Val Glu Thr Ile Phe Leu Gly Ser<br>355 360 365 | | 1162 |
| agg ccc tgg atg cca ggg act ccc cgc agg ttg ccc cgc ctg ccc cag<br>Arg Pro Trp Met Pro Gly Thr Pro Arg Arg Leu Pro Arg Leu Pro Gln<br>370 375 380 | | 1210 |
| cgc tac tgg caa atg cgg ccc ctg ttt ctg gag ctg ctt ggg aac cac<br>Arg Tyr Trp Gln Met Arg Pro Leu Phe Leu Glu Leu Leu Gly Asn His<br>385 390 395 400 | | 1258 |
| gcg cag tgc ccc tac ggg gtg ctc ctc aag acg cac tgc ccg ctg cga<br>Ala Gln Cys Pro Tyr Gly Val Leu Leu Lys Thr His Cys Pro Leu Arg<br>405 410 415 | | 1306 |
| gct gcg gtc acc cca gca gcc ggt gtc tgt gcc cgg gag aag ccc cag<br>Ala Ala Val Thr Pro Ala Ala Gly Val Cys Ala Arg Glu Lys Pro Gln<br>420 425 430 | | 1354 |
| ggc tct gtg gcg gcc ccc gag gag gag gac aca gac ccc cgt cgc ctg<br>Gly Ser Val Ala Ala Pro Glu Glu Glu Asp Thr Asp Pro Arg Arg Leu<br>435 440 445 | | 1402 |
| gtg cag ctg ctc cgc cag cac agc agc ccc tgg cag gtg tac ggc ttc<br>Val Gln Leu Leu Arg Gln His Ser Ser Pro Trp Gln Val Tyr Gly Phe<br>450 455 460 | | 1450 |
| gtg cgg gcc tgc ctg cgc cgg ctg gtg ccc cca ggc ctc tgg ggc tcc<br>Val Arg Ala Cys Leu Arg Arg Leu Val Pro Pro Gly Leu Trp Gly Ser<br>465 470 475 480 | | 1498 |
| agg cac aac gaa cgc cgc ttc ctc agg aac acc aag aag ttc atc tcc<br>Arg His Asn Glu Arg Arg Phe Leu Arg Asn Thr Lys Lys Phe Ile Ser<br>485 490 495 | | 1546 |
| ctg ggg aag cat gcc aag ctc tcg ctg cag gag ctg acg tgg aag atg<br>Leu Gly Lys His Ala Lys Leu Ser Leu Gln Glu Leu Thr Trp Lys Met<br>500 505 510 | | 1594 |

-continued

| | |
|---|---|
| agc gtg cgg gac tgc gct tgg ctg cgc agg agc cca ggg gtt ggc tgt<br>Ser Val Arg Asp Cys Ala Trp Leu Arg Arg Ser Pro Gly Val Gly Cys<br>      515                   520                  525 | 1642 |
| gtt ccg gcc gca gag cac cgt ctg cgt gag gag atc ctg gcc aag ttc<br>Val Pro Ala Ala Glu His Arg Leu Arg Glu Glu Ile Leu Ala Lys Phe<br>530                     535                   540 | 1690 |
| ctg cac tgg ctg atg agt gtg tac gtc gtc gag ctc ctc agg tct ttc<br>Leu His Trp Leu Met Ser Val Tyr Val Val Glu Leu Leu Arg Ser Phe<br>545                     550                   555                  560 | 1738 |
| ttt tat gtc acg gag acc acg ttt caa aag aac agg ctc ttt ttc tac<br>Phe Tyr Val Thr Glu Thr Thr Phe Gln Lys Asn Arg Leu Phe Phe Tyr<br>                   565                   570                  575 | 1786 |
| cgg aag agt gtc tgg agc aag ttg caa agc att gga atc aga cag cac<br>Arg Lys Ser Val Trp Ser Lys Leu Gln Ser Ile Gly Ile Arg Gln His<br>                   580                   585                  590 | 1834 |
| ttg aag agg gtg cag ctg cgg gag ctg tcg gaa gca gag gtc agg cag<br>Leu Lys Arg Val Gln Leu Arg Glu Leu Ser Glu Ala Glu Val Arg Gln<br>               595                   600                  605 | 1882 |
| cat cgg gaa gcc agg ccc gcc ctg ctg acg tcc aga ctc cgc ttc atc<br>His Arg Glu Ala Arg Pro Ala Leu Leu Thr Ser Arg Leu Arg Phe Ile<br>610                     615                   620 | 1930 |
| ccc aag cct gac ggg ctg cgg ccg att gtg aac atg gac tac gtc gtg<br>Pro Lys Pro Asp Gly Leu Arg Pro Ile Val Asn Met Asp Tyr Val Val<br>625                     630                   635                  640 | 1978 |
| gga gcc aga acg ttc cgc aga gaa aag agg gcc gag cgt ctc acc tcg<br>Gly Ala Arg Thr Phe Arg Arg Glu Lys Arg Ala Glu Arg Leu Thr Ser<br>                   645                   650                  655 | 2026 |
| agg gtg aag gca ctg ttc agc gtg ctc aac tac gag cgg gcg cgg cgc<br>Arg Val Lys Ala Leu Phe Ser Val Leu Asn Tyr Glu Arg Ala Arg Arg<br>660                     665                   670 | 2074 |
| ccc ggc ctc ctg ggc gcc tct gtg ctg ggc ctg gac gat atc cac agg<br>Pro Gly Leu Leu Gly Ala Ser Val Leu Gly Leu Asp Asp Ile His Arg<br>               675                   680                  685 | 2122 |
| gcc tgg cgc acc ttc gtg ctg cgt gtg cgg gcc cag gac ccg ccg cct<br>Ala Trp Arg Thr Phe Val Leu Arg Val Arg Ala Gln Asp Pro Pro Pro<br>690                     695                   700 | 2170 |
| gag ctg tac ttt gtc aag gtg gat gtg acg ggc gcg tac gac acc atc<br>Glu Leu Tyr Phe Val Lys Val Asp Val Thr Gly Ala Tyr Asp Thr Ile<br>705                     710                   715                  720 | 2218 |
| ccc cag gac agg ctc acg gag gtc atc gcc agc atc atc aaa ccc cag<br>Pro Gln Asp Arg Leu Thr Glu Val Ile Ala Ser Ile Ile Lys Pro Gln<br>                   725                   730                  735 | 2266 |
| aac acg tac tgc gtg cgt cgg tat gcc gtg gtc cag aag gcc gcc cat<br>Asn Thr Tyr Cys Val Arg Arg Tyr Ala Val Val Gln Lys Ala Ala His<br>740                     745                   750 | 2314 |
| ggg cac gtc cgc aag gcc ttc aag agc cac gtc tct acc ttg aca gac<br>Gly His Val Arg Lys Ala Phe Lys Ser His Val Ser Thr Leu Thr Asp<br>               755                   760                  765 | 2362 |
| ctc cag ccg tac atg cga cag ttc gtg gct cac ctg cag gag acc agc<br>Leu Gln Pro Tyr Met Arg Gln Phe Val Ala His Leu Gln Glu Thr Ser<br>770                     775                   780 | 2410 |
| ccg ctg agg gat gcc gtc gtc atc gag cag agc tcc tcc ctg aat gag<br>Pro Leu Arg Asp Ala Val Val Ile Glu Gln Ser Ser Ser Leu Asn Glu<br>785                     790                   795                  800 | 2458 |
| gcc agc agt ggc ctc ttc gac gtc ttc cta cgc ttc atg tgc cac cac<br>Ala Ser Ser Gly Leu Phe Asp Val Phe Leu Arg Phe Met Cys His His<br>                   805                   810                  815 | 2506 |
| gcc gtg cgc atc agg ggc aag tcc tac gtc cag tgc cag ggg atc ccg<br>Ala Val Arg Ile Arg Gly Lys Ser Tyr Val Gln Cys Gln Gly Ile Pro | 2554 |

```
                820              825              830
cag ggc tcc atc ctc tcc acg ctg ctc tgc agc ctg tgc tac ggc gac    2602
Gln Gly Ser Ile Leu Ser Thr Leu Leu Cys Ser Leu Cys Tyr Gly Asp
            835              840              845 atg gag aac aag ctg ttt gcg ggg att cgg cgg gac ggg ctg ctc gtg    2650
Met Glu Asn Lys Leu Phe Ala Gly Ile Arg Arg Asp Gly Leu Leu Val
850              855              860 aca cct cac ctc acc cac gcg aaa acc ttc ctc agg acc ctg gtc cga    2698
Thr Pro His Leu Thr His Ala Lys Thr Phe Leu Arg Thr Leu Val Arg
865              870              875              880 ggt gtc cct gag tat ggc tgc gtg gtg aac ttg cgg aag aca gtg gtg    2746
Gly Val Pro Glu Tyr Gly Cys Val Val Asn Leu Arg Lys Thr Val Val
                885              890              895 aac ttc cct gta gaa gac gag gcc ctg ggt ggc acg gct ttt gtt cag    2794
Asn Phe Pro Val Glu Asp Glu Ala Leu Gly Gly Thr Ala Phe Val Gln
            900              905              910 atg ccg gcc cac ggc cta ttc ccc tgg tgc ggc ctg ctg gat acc        2842
Met Pro Ala His Gly Leu Phe Pro Trp Cys Gly Leu Leu Leu Asp Thr
            915              920              925 cgg acc ctg gag gtg cag agc gac tac tcc agc tat gcc cgg acc tcc    2890
Arg Thr Leu Glu Val Gln Ser Asp Tyr Ser Ser Tyr Ala Arg Thr Ser
930              935              940 atc aga gcc agt ctc acc ttc aac cgc ggc ttc aag gct ggg agg aac    2938
Ile Arg Ala Ser Leu Thr Phe Asn Arg Gly Phe Lys Ala Gly Arg Asn
945              950              955              960 atg cgt cgc aaa ctc ttt ggg gtc ttg cgg ctg aag tgt cac agc ctg    2986
Met Arg Arg Lys Leu Phe Gly Val Leu Arg Leu Lys Cys His Ser Leu
                965              970              975 ttt ctg gat ttg cag gtg aac agc ctc cag acg gtg tgc acc aac atc    3034
Phe Leu Asp Leu Gln Val Asn Ser Leu Gln Thr Val Cys Thr Asn Ile
            980              985              990 tac aag atc ctc ctg ctg cag gcg tac agg ttt cac gca tgt gtg ctg    3082
Tyr Lys Ile Leu Leu Leu Gln Ala Tyr Arg Phe His Ala Cys Val Leu
            995              1000             1005 cag ctc cca ttt cat cag caa gtt tgg aag aac ccc aca ttt ttc        3127
Gln Leu Pro Phe His Gln Gln Val Trp Lys Asn Pro Thr Phe Phe
        1010             1015             1020 ctg cgc gtc atc tct gac acg gcc tcc ctc tgc tac tcc atc ctg        3172
Leu Arg Val Ile Ser Asp Thr Ala Ser Leu Cys Tyr Ser Ile Leu
        1025             1030             1035 aaa gcc aag aac gca ggg atg tcg ctg ggg gcc aag ggc gcc gcc        3217
Lys Ala Lys Asn Ala Gly Met Ser Leu Gly Ala Lys Gly Ala Ala
        1040             1045             1050 ggc cct ctg ccc tcc gag gcc gtg cag tgg ctg tgc cac caa gca        3262
Gly Pro Leu Pro Ser Glu Ala Val Gln Trp Leu Cys His Gln Ala
        1055             1060             1065 ttc ctg ctc aag ctg act cga cac cgt gtc acc tac gtg cca ctc        3307
Phe Leu Leu Lys Leu Thr Arg His Arg Val Thr Tyr Val Pro Leu
        1070             1075             1080 ctg ggg tca ctc agg aca gcc cag acg cag ctg agt cgg aag ctc        3352
Leu Gly Ser Leu Arg Thr Ala Gln Thr Gln Leu Ser Arg Lys Leu
        1085             1090             1095 ccg ggg acg acg ctg act gcc ctg gag gcc gca gcc aac ccg gca        3397
Pro Gly Thr Thr Leu Thr Ala Leu Glu Ala Ala Ala Asn Pro Ala
        1100             1105             1110 ctg ccc tca gac ttc aag acc atc ctg gac tga tggccacccg             3440
Leu Pro Ser Asp Phe Lys Thr Ile Leu Asp
        1115             1120 cccacagcca ggccgagagc agacaccagc agccctgtca cgccgggctc tacgtcccag  3500
```

-continued

```
ggagggaggg gcggcccaca cccaggcccg caccgctggg agtctgaggc ctgagtgagt    3560
gtttggccga ggcctgcatg tccggctgaa ggctgagtgt ccggctgagg cctgagcgag    3620
tgtccagcca agggctgagt gtccagcaca cctgccgtct tcacttcccc acaggctggc    3680
gctcggctcc accccagggc cagcttttcc tcaccaggag cccggcttcc actccccaca    3740
taggaatagt ccatcccag attcgccatt gttcacccct cgccctgccc tcctttgcct    3800
tccaccccca ccatccaggt ggagaccctg agaaggaccc tgggagctct ggaatttgg     3860 agtgaccaaa ggtgtgccct gtacacaggc gaggaccctg cacctggatg ggggtccctg    3920
tgggtcaaat tggggggagg tgctgtggga gtaaaatact gaatatatga gttttttcagt  3980 tttgaaaaaa a                                                         3991
```

<210> SEQ ID NO 41
<211> LENGTH: 1123
<212> TYPE: PRT
<213> ORGANISM: Artificial
<220> FEATURE:
<223> OTHER INFORMATION: Synthetic Construct

<400> SEQUENCE: 41

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270
```

```
Val Ser Pro Ala Arg Pro Ala Glu Glu Ala Thr Ser Leu Glu Gly Ala
    275                 280                 285

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
        675                 680                 685
```

-continued

Ala Trp Arg Thr Phe Val Leu Arg Val Arg Ala Gln Asp Pro Pro
690                     695                     700

Glu Leu Tyr Phe Val Lys Val Asp Val Thr Gly Ala Tyr Asp Thr Ile
705                     710                     715                 720

Pro Gln Asp Arg Leu Thr Glu Val Ile Ala Ser Ile Ile Lys Pro Gln
                    725                     730                     735

Asn Thr Tyr Cys Val Arg Arg Tyr Ala Val Val Gln Lys Ala Ala His
                740                     745                     750

Gly His Val Arg Lys Ala Phe Lys Ser His Val Ser Thr Leu Thr Asp
            755                     760                     765

Leu Gln Pro Tyr Met Arg Gln Phe Val Ala His Leu Gln Glu Thr Ser
770                     775                     780

Pro Leu Arg Asp Ala Val Val Ile Glu Gln Ser Ser Ser Leu Asn Glu
785                     790                     795                 800

Ala Ser Ser Gly Leu Phe Asp Val Phe Leu Arg Phe Met Cys His His
                805                     810                     815

Ala Val Arg Ile Arg Gly Lys Ser Tyr Val Gln Cys Gln Gly Ile Pro
            820                     825                     830

Gln Gly Ser Ile Leu Ser Thr Leu Leu Cys Ser Leu Cys Tyr Gly Asp
        835                     840                     845

Met Glu Asn Lys Leu Phe Ala Gly Ile Arg Arg Asp Gly Leu Leu Val
850                     855                     860

Thr Pro His Leu Thr His Ala Lys Thr Phe Leu Arg Thr Leu Val Arg
865                     870                     875                 880

Gly Val Pro Glu Tyr Gly Cys Val Val Asn Leu Arg Lys Thr Val Val
                885                     890                     895

Asn Phe Pro Val Glu Asp Glu Ala Leu Gly Gly Thr Ala Phe Val Gln
            900                     905                     910

Met Pro Ala His Gly Leu Phe Pro Trp Cys Gly Leu Leu Leu Asp Thr
        915                     920                     925

Arg Thr Leu Glu Val Gln Ser Asp Tyr Ser Ser Tyr Ala Arg Thr Ser
930                     935                     940

Ile Arg Ala Ser Leu Thr Phe Asn Arg Gly Phe Lys Ala Gly Arg Asn
945                     950                     955                 960

Met Arg Arg Lys Leu Phe Gly Val Leu Arg Leu Lys Cys His Ser Leu
                965                     970                     975

Phe Leu Asp Leu Gln Val Asn Ser Leu Gln Thr Val Cys Thr Asn Ile
            980                     985                     990

Tyr Lys Ile Leu Leu Leu Gln Ala  Tyr Arg Phe His Ala  Cys Val Leu
        995                     1000                    1005

Gln Leu  Pro Phe His Gln Gln  Val Trp Lys Asn Pro  Thr Phe Phe
    1010                    1015                    1020

Leu Arg  Val Ile Ser Asp Thr  Ala Ser Leu Cys Tyr  Ser Ile Leu
    1025                    1030                    1035

Lys Ala  Lys Asn Ala Gly Met  Ser Leu Gly Ala Lys  Gly Ala Ala
    1040                    1045                    1050

Gly Pro  Leu Pro Ser Glu Ala  Val Gln Trp Leu Cys  His Gln Ala
    1055                    1060                    1065

Phe Leu  Leu Lys Leu Thr Arg  His Arg Val Thr Tyr  Val Pro Leu
    1070                    1075                    1080

-continued

```
Leu Gly Ser Leu Arg Thr Ala Gln Thr Gln Leu Ser Arg Lys Leu
    1085                1090                1095

Pro Gly Thr Thr Leu Thr Ala Leu Glu Ala Ala Ala Asn Pro Ala
    1100                1105                1110

Leu Pro Ser Asp Phe Lys Thr Ile Leu Asp
    1115                1120
```

UNITED STATES PATENT AND TRADEMARK OFFICE
CERTIFICATE OF CORRECTION

PATENT NO. : 9,624,479 B2  
APPLICATION NO. : 13/975404  
DATED : April 18, 2017  
INVENTOR(S) : Pierre Langlade-Demoyen et al.

Page 1 of 1

It is certified that error appears in the above-identified patent and that said Letters Patent is hereby corrected as shown below:

On the Title Page

At item (30), delete "(FR)" and add --(EP)--

Signed and Sealed this
Eighteenth Day of August, 2020

Andrei Iancu
*Director of the United States Patent and Trademark Office*